(12) United States Patent
Kim et al.

(10) Patent No.: US 10,849,990 B2
(45) Date of Patent: Dec. 1, 2020

(54) METHODS FOR TREATING PARKINSON'S DISEASE

(71) Applicant: KOREA ADVANCED INSTITUTE OF SCIENCE AND TECHNOLOGY, Daejeon (KR)

(72) Inventors: Daesoo Kim, Daejeon (KR); Jeongjin Kim, Daejeon (KR); Youngsoo Kim, Daejeon (KR); Minju Jeong, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 34 days.

(21) Appl. No.: 15/962,894

(22) Filed: Apr. 25, 2018

(65) Prior Publication Data

US 2019/0328905 A1    Oct. 31, 2019

(51) Int. Cl.

| | |
|---|---|
| *A61K 48/00* | (2006.01) |
| *C12N 15/79* | (2006.01) |
| *C07H 21/04* | (2006.01) |
| *C12N 15/86* | (2006.01) |
| *C12N 5/0793* | (2010.01) |
| *A61N 5/06* | (2006.01) |
| *C12N 15/113* | (2010.01) |
| *A61P 25/16* | (2006.01) |
| *C12N 15/867* | (2006.01) |
| *C12N 15/861* | (2006.01) |
| *C12N 15/864* | (2006.01) |

(52) U.S. Cl.
CPC ............ *A61K 48/005* (2013.01); *A61N 5/062* (2013.01); *A61P 25/16* (2018.01); *C12N 5/0619* (2013.01); *C12N 15/113* (2013.01); *C12N 15/86* (2013.01); *A61N 2005/0663* (2013.01); *C07H 21/04* (2013.01); *C12N 15/861* (2013.01); *C12N 15/867* (2013.01); *C12N 15/8645* (2013.01)

(58) Field of Classification Search
CPC .... A61K 48/005; C12N 15/86; C12N 15/861; C12N 15/8645; C12N 15/867; C07H 21/04
USPC ..................... 514/44 R; 435/320.1; 536/23.5
See application file for complete search history.

(56) References Cited

PUBLICATIONS

Kaur et al., 2009, Current Gene Therapy, vol. 9. p. 434-458.*
Shim et al., 2017, Current Gene Therapy, vol. 17, No. 5, p. 1-18.*
Lenzi et al., 2014, NCBI Bookshelf, A Service of the National Library of Medicine, National Institute of Health, Oversight and Review of Clinical Gene Transfer Protocols: Assessing the Role of the Recombinant DNA Advisory Committee. Washington (DC): National Academies Press (US), pp. 1-16.*
Dunbar et al., 2018, Science, vol. 359, eaan4672, p. 1-10.*
Pettit and Augustine "Distribution of Functional Glutamate and GABA Receptors on Hippocampal Pyramidal Cells and Interneurons" *The American Physiological Society* 28-38 (2000).
Kim et al. "Lack of the Burst Firing of Thalamocortical Relay Neurons and Resistance to Absence Seizures in Mice Lacking $\alpha_{1G}$ T-Type $Ca^{2+}$ Channels" *Neuron* 31:35-45 (2001).
Brown et al. "Dopamine Dependency of Oscillations between Subthalamic Nucleus and Pallidum in Parkinson's Disease" *The Journal of Neuroscience* 21(3):1033-1038 (2001).
Yang et al. "A Murine Model for Human Sepiapterin-Reductase Deficiency" *The American Journal of Human Genetics* 78:575-587 (2006).
Ittner et al. "Parkinsonism and impaired axonal transport in a mouse model of frontotemporal dementia" *PNAS* 105(41):15997-16002 (2008).
Kraus et al. "In Vitro Characterization of T-Type Calcium Channel Antagonist TTA-A2 and In Vivo Effects on Arousal in Mice" *The Journal of Pharmacology and Experimental Therapeutics* 335(2):409-417 (2010).
Park et al. "Cav3.1 is a tremor rhythm pacemaker in the inferior olive" *PNAS* 107(23):10731-10736 (2010).
Kim et al. "Thalamic T-Type $Ca^{2+}$ Channels Mediate Frontal Lobe Dysfunctions Caused by a Hypoxia-Like Damage in the Prefrontal Cortex" *The Journal of Neuroscience* 31(11):4063-4073 (2011).

* cited by examiner

*Primary Examiner* — Shin Lin Chen

(74) *Attorney, Agent, or Firm* — Klarquist Sparkman, LLP

(57) ABSTRACT

The present invention relates to a method for treating Parkinson's disease. According to this method, a halorhodopsin protein, a polynucleotide encoding the halorhodopsin protein or a vector containing the polynucleotide above is introduced into ventrolateral thalamus (VL) or medial globus pallidus (GPm) neurons of a subject having Parkinson's disease. The VL neurons are then illuminated with green light or exposed to a T type $Ca^{2+}$ channel blocker to inhibit rebound firing of VL neurons. By inhibiting rebound firing of VL neurons, Parkinson's disease can be treated or prevented.

6 Claims, 23 Drawing Sheets
(23 of 23 Drawing Sheet(s) Filed in Color)
Specification includes a Sequence Listing.

FIG. 5
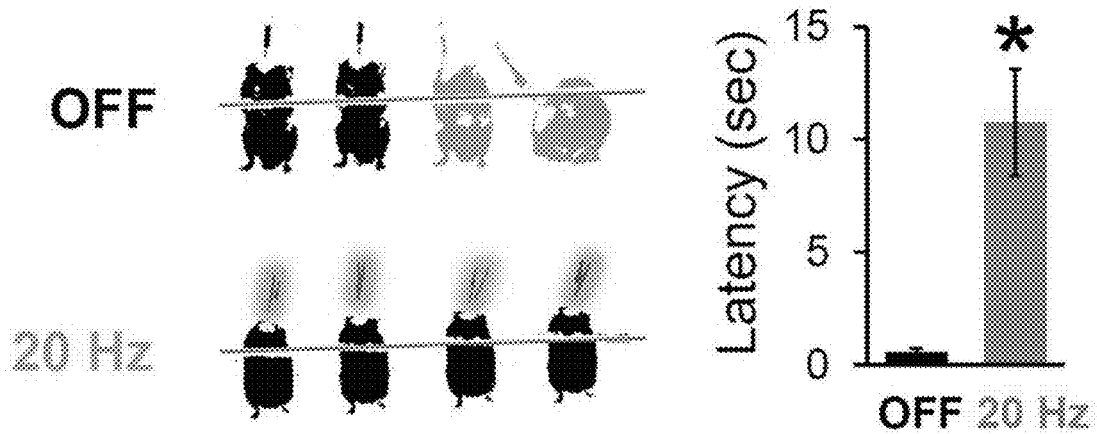
FIG. 6(A)          FIG. 6(B)
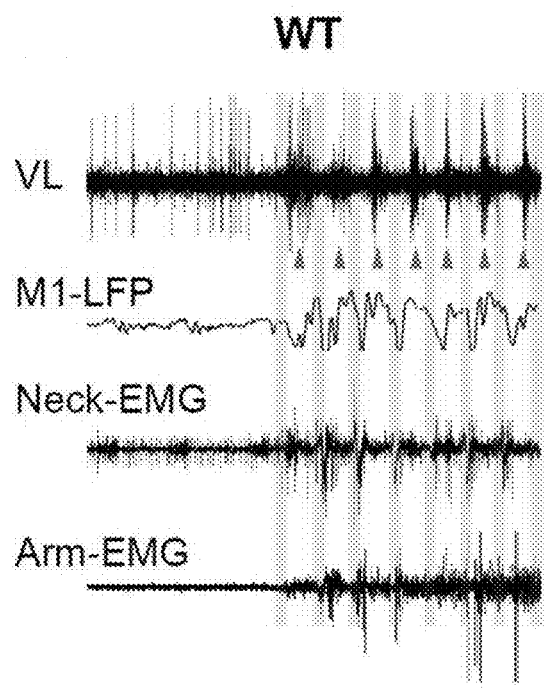
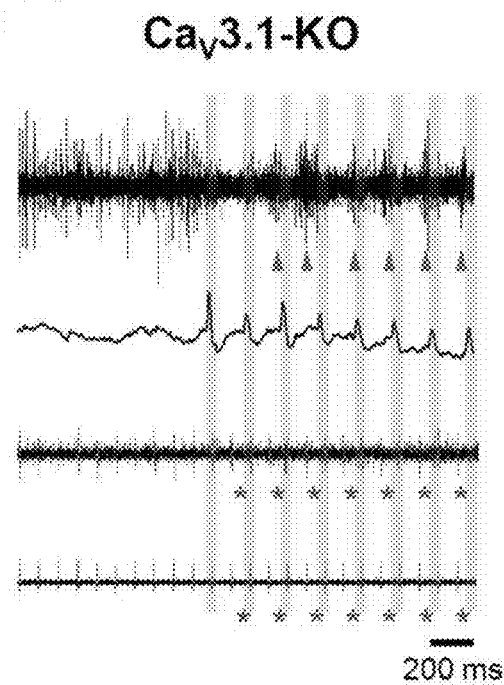

FIG. 7
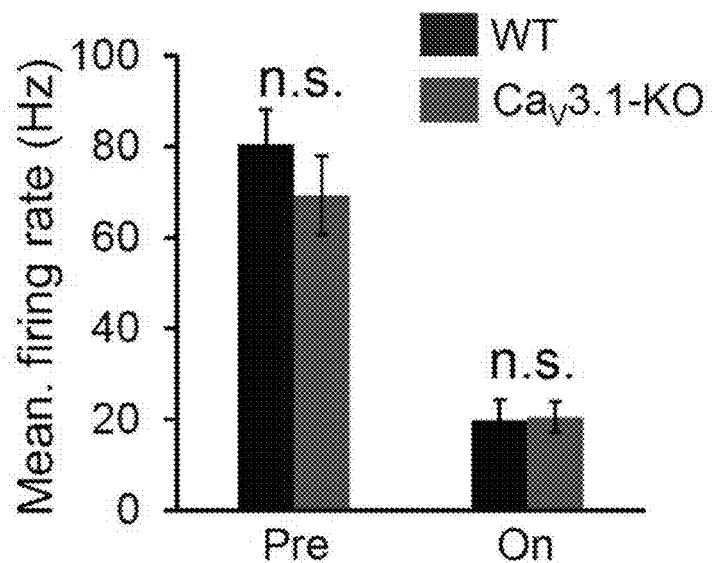
FIG. 8(A)     FIG. 8(B)     FIG. 8(C)
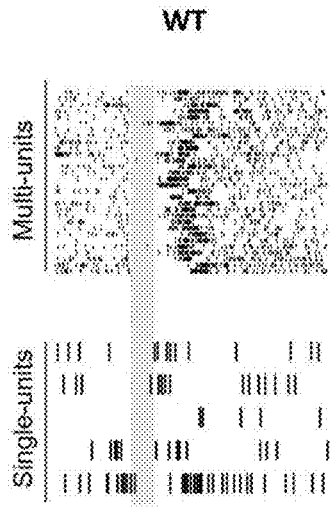 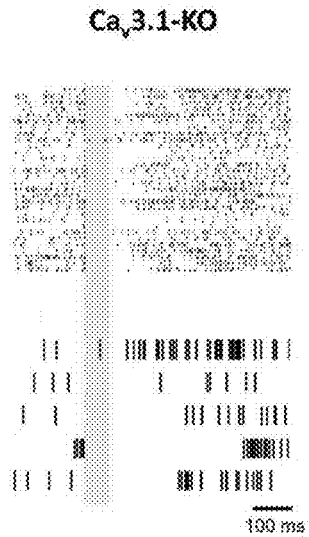 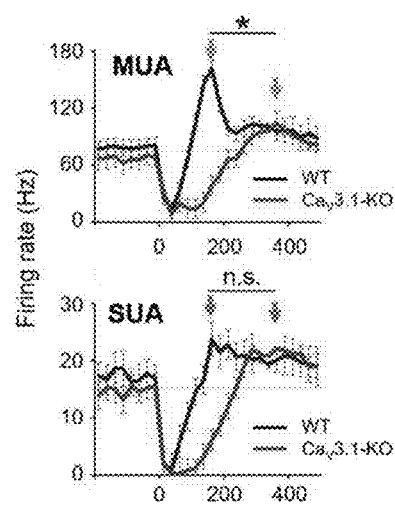
FIG. 8(D)     FIG. 8(E)     FIG. 8(F)

FIG. 11(A)  FIG. 11(B)  FIG. 11(C)
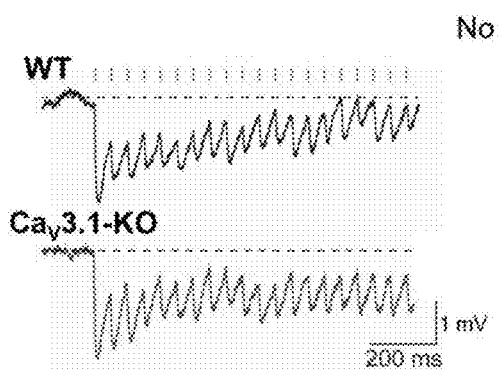
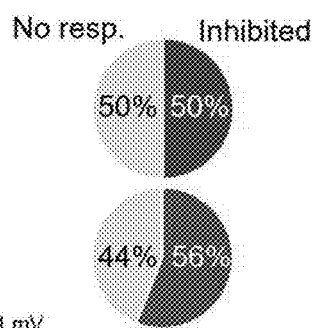
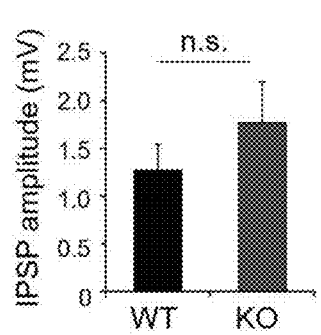
FIG. 12(A)  FIG. 12(C)
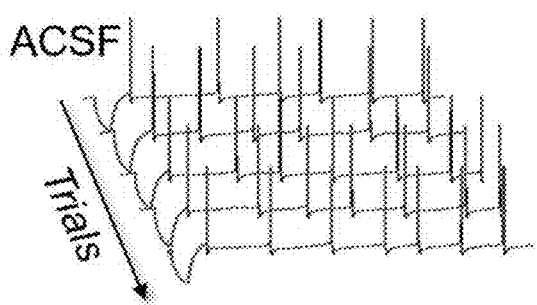
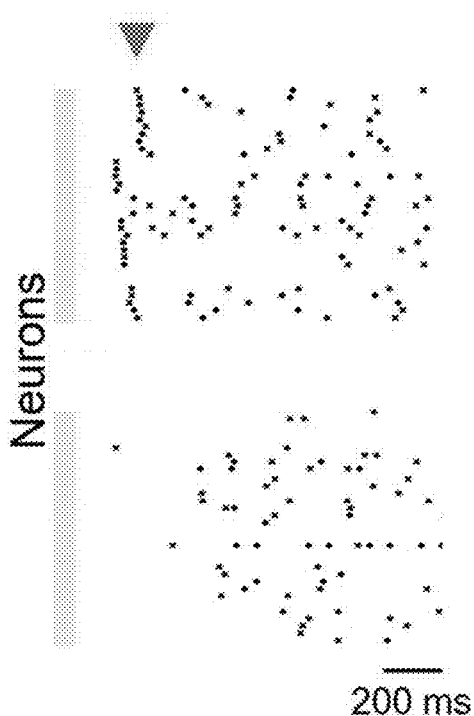
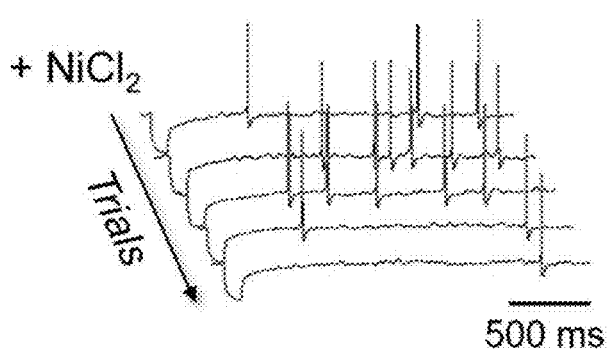
FIG. 12(B)  FIG. 12(D)

FIG. 15(A)
FIG. 15(B)
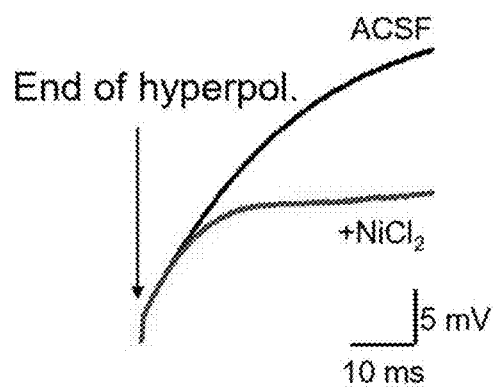
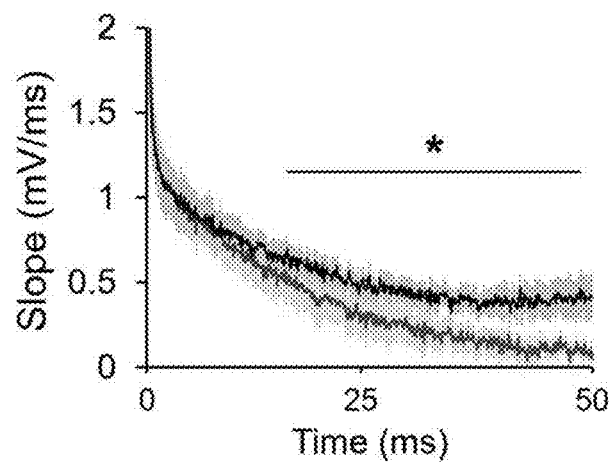
FIG. 16(A)
FIG. 16(B)
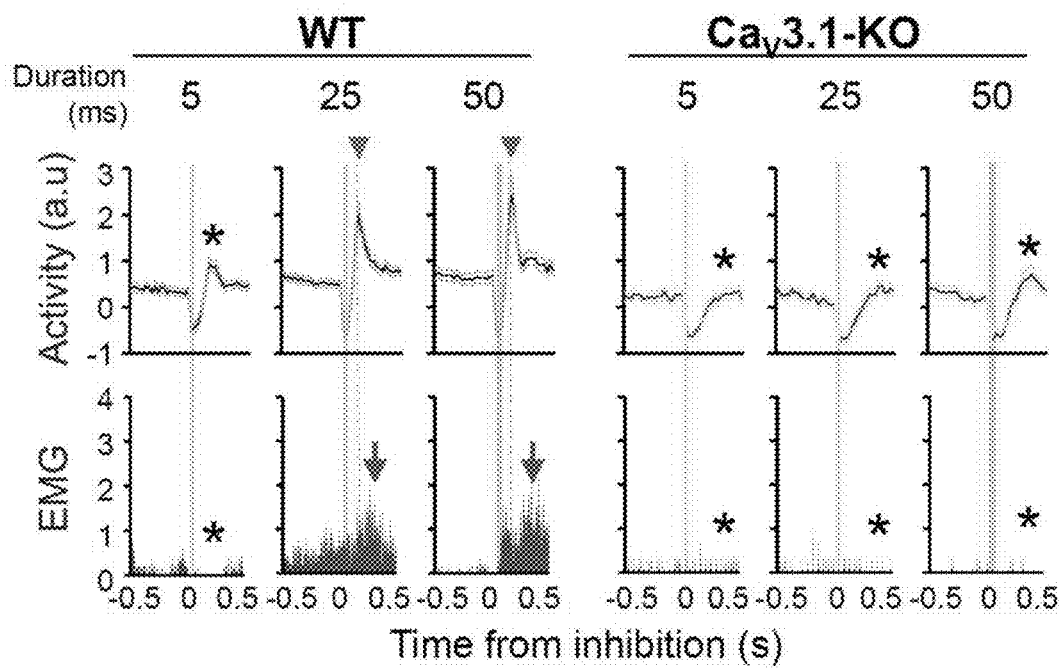

FIG. 17(A)
FIG. 17(B)
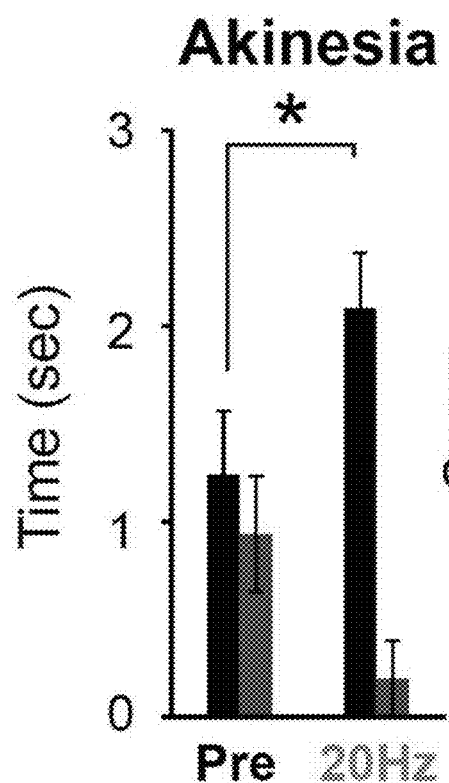
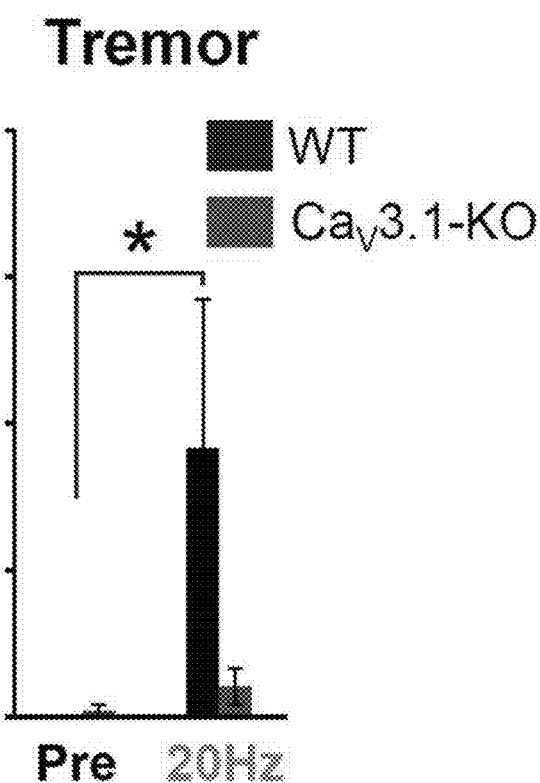

FIG. 19
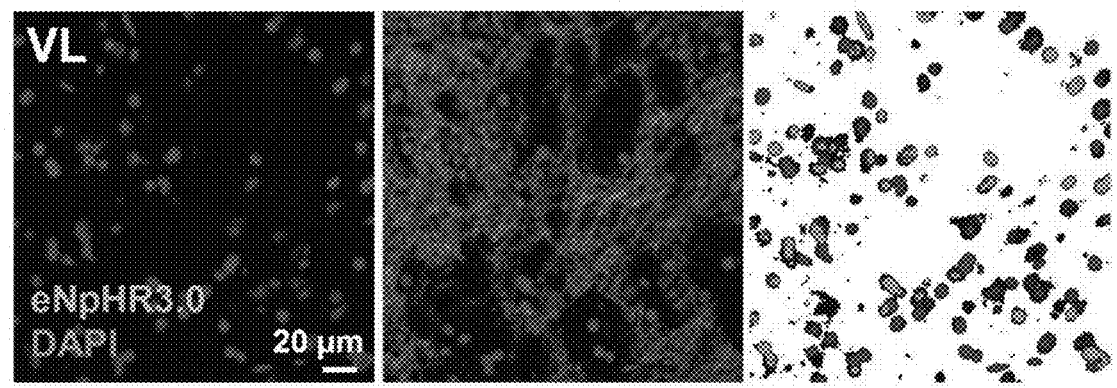
FIG. 20(A)
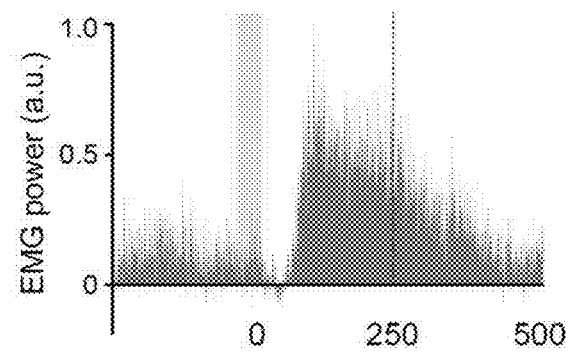
FIG. 20(B)
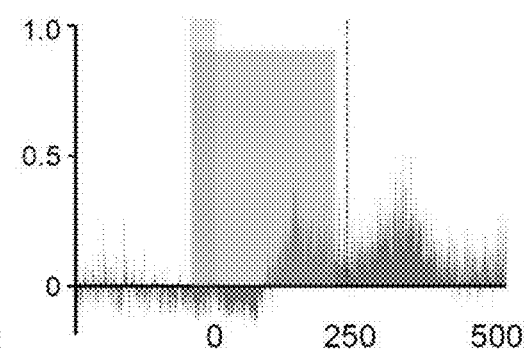
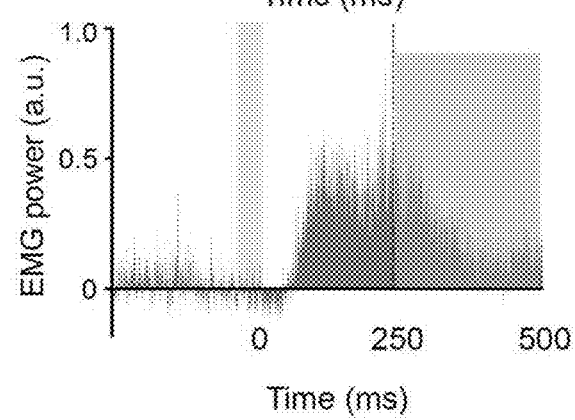
FIG. 20(C)

FIG. 27(A)
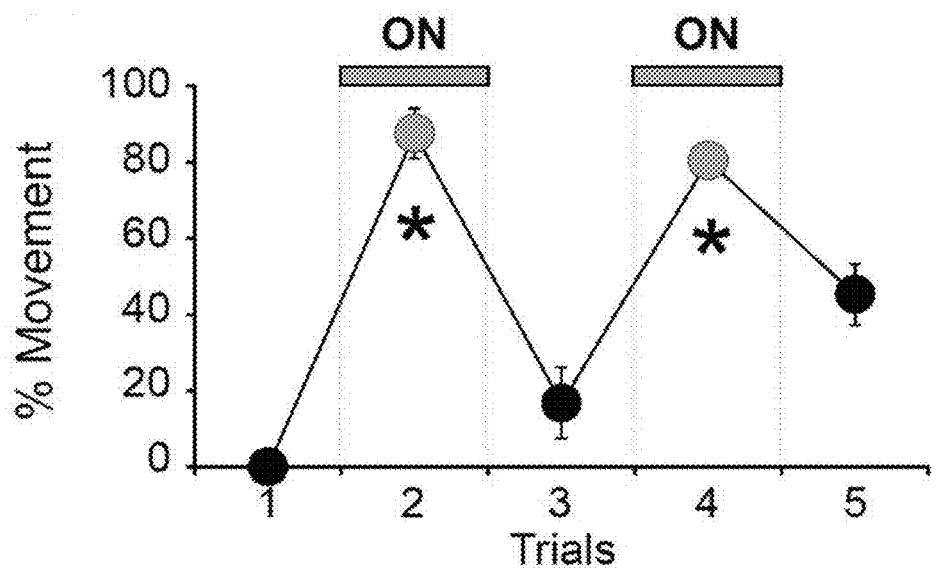
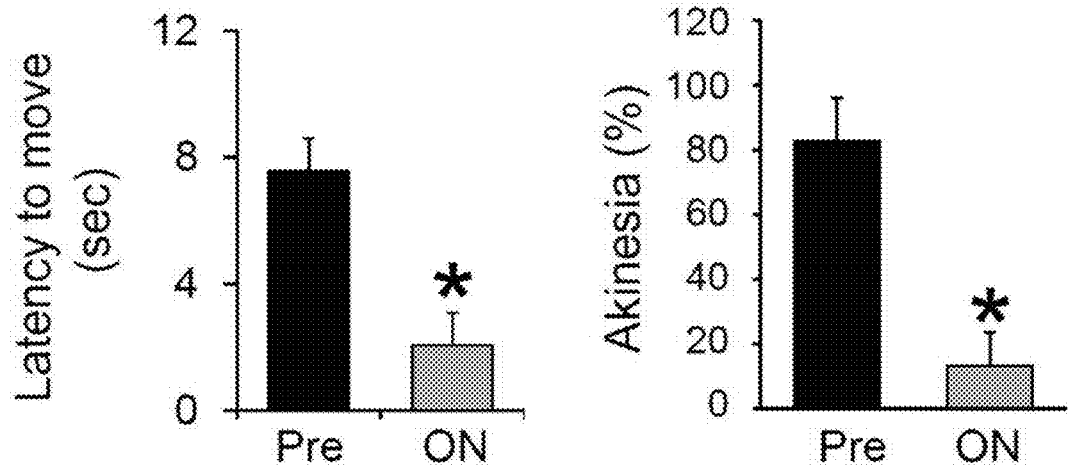
FIG. 27(B)  FIG. 27(C)

FIG. 29(A)
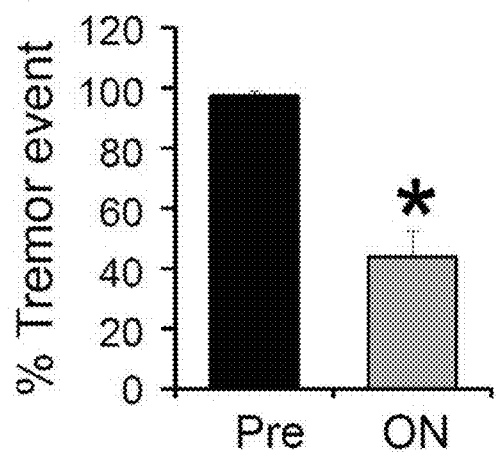
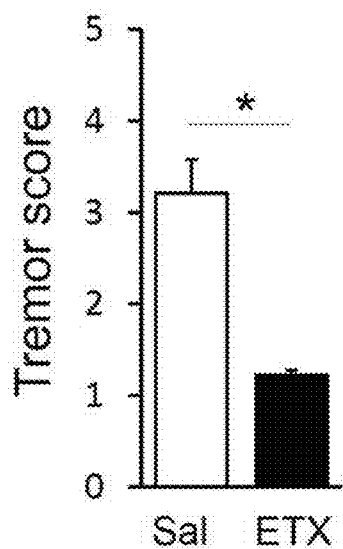
FIG. 29(B)
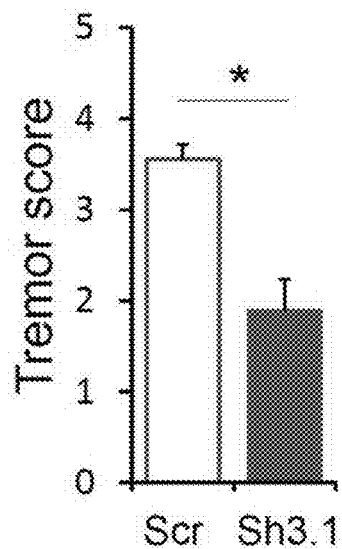
FIG. 29(C)

METHODS FOR TREATING PARKINSON'S DISEASE

1. FIELD OF THE INVENTION

The present invention relates to a method for treating Parkinson's disease comprising the step of inhibiting rebound firing of ventrolateral thalamus (VL) neurons.

2. DESCRIPTION OF THE RELATED ART

Parkinson's disease is a progressive disease taking the second highest incidence among neurodegenerative diseases. The incidence rate of this disease is continuously increasing with the increase of the aged population, so that it is a socially and economically problematic intractable disease. It is known that approximately 4 million people worldwide are suffering this disease. In USA, about 50,000 new patients have been reported every year. The incidence rate of this disease is one in 1000 people, and the higher the age, the higher the incidence.

The exact cause of Parkinson's disease has not been disclosed yet, but it is believed that the disorder in the neurons gathered tightly in pars compacta of substantia nigra of basal ganglia is the reason. These neurons produce dopamine, a neurotransmitter. Dopamine is functioning as an inhibitor of nerve stimulation in the brain so that it is involved in suppressing unintentional movement. It is also involved in regulating signal output of globus pallidus through caudate nucleus and putamen. In the case of Parkinson's disease, as dopamine neurons in the substantia nigra die, their signaling is reduced and inhibitory signaling through the D1 receptor of the striatum is also reduced. In general, when the globus pallidus suppresses the thalamus excessively, the motor neurons that descend from the thalamus to the cerebral cortex are suppressed to cause Parkinson's disease specific symptoms such as bradykinesia.

The drugs currently used or under development for the treatment of Parkinson's disease are as follows. The most widely used drugs are dopamine precursors and dopamine receptor fenofibrates such as Levodopa. In addition, COMT inhibitors and MAO-B inhibitors functioning to maintain the level of dopamine in the brain by suppressing dopamine metabolism have been used. Antimuscarinics and NMDA antagonists have been developed and used as drugs for improving neurotransmitters other than dopamine. The attempts to develop or use brain cell protective agents, antioxidants, brain cell death inhibitors, and brain function agonists as therapeutic agents have been made. To treat the terminal patients who cannot be efficiently treated by pharmacotherapy, a surgical operation such as deep brain stimulation is tried. However, since the cause of Parkinson's disease is not known exactly, the treatment methods of these days are only to improve the symptoms instead of fundamentally treating the disease.

Optogenetics is a technology that combines optics and genetics, which is a biological technique to regulate cells of living tissues with light. The most representative example in this field is that neurons are genetically manipulated in order to express ion channels that respond to light. By using optogenetics, the activity of each individual neuron in living tissues or even in free-moving animals can be regulated and observed and also the effect of the regulation of neuronal activity can be observed in real time. To regulate the neuronal activity, light-responsive proteins such as channelrhodopsin, halorhodopsin, and archaerhodopsin can be used. To record the neuronal activity optically, optogenetic sensors such as GCaMP sensing the changes of calcium concentration, synaptopHluorin sensing the secretion of neurons, and Arclightning (ASAP1) sensing the cell membrane potential are used. As the regulation of neuronal activity is realized by taking advantage of optogenetics, it can be applied to understand the mechanism of neurological disease or to develop a new treatment method for neurological disease.

The intracellular calcium influx through voltage-gated calcium channel is known to mediate a wide range of cellular and physiological responses including hormone secretion and gene expression. The voltage-gated calcium channel is deeply involved in the secretion and transmission of neurotransmitters and is mainly found in the central and peripheral nervous system and neuroendocrine cells. The voltage-gated calcium channel is classified into L type, T type, N type, P/Q type, and R type in mammalian cells. The T-type calcium channel has three subtypes called α1G ($Ca_V3.1$), α1H($Ca_V3.2$), and α1I($Ca_V3.3$). According to the previous reports, T-type calcium channels are involved in pathologies related to neurological diseases and disorders including epilepsy, essential hypertension, pain, neuropathic pain, schizophrenia, Parkinson's disease, depression, anxiety, sleep disorder, dyspnoea, psychosis, and schizophrenia (references: J Neuroscience, 14, 5485 (1994); Drugs Future 30(6), 573-580(2005); EMBO J, 24, 315-324 (2005); Drug Discovery Today, 11, 5/6, 245-253(2006)).

The attempt to treat Parkinson's disease using optogenetics or T-type calcium channel was tried but this was only based on the technique to alleviate the inhibitory signals of the basal ganglia that suppress motor neurons. The present inventors confirmed that the inhibitory input from the medial globus pallidus (GPm) produced excitatory motor signals excessively after the suppression via T-type calcium channels in the ventrolateral thalamus (VL) and such excitatory motor signals accelerated abnormal movements similar to Parkinson's disease. Thereafter, the present inventors confirmed that when either inhibitory inputs from the GPm or postsynaptic VL neurons were photoinhibited or the T-type calcium channel involved in inducing rebound firing in the ventrolateral thalamus was blocked or knocked-down, the excitatory motor signal of the thalamus was inhibited and the movement abnormalities similar to Parkinson's disease was alleviated in Parkinson's disease animal model, leading to the completion of the present invention.

SUMMARY OF THE INVENTION

It is an object of the present invention to provide a method for treating Parkinson's disease.

To achieve the above object, the present invention provides a method for treating Parkinson's disease comprising the step of inhibiting rebound firing of ventrolateral thalamus (VL) neurons.

Advantageous Effect

In the method for treating Parkinson's disease of the present invention, a halorhodopsin protein, a polynucleotide encoding the halorhodopsin protein or a vector containing the polynucleotide above is treated to ventrolateral thalamus (VL) or medial globus pallidus (GPm) neurons of a subject having Parkinson's disease, followed by illumination with green light, or a $Ca_V3.1$ gene expression inhibitor is treated to VL neurons of a subject having Parkinson's disease to inhibit rebound firing of VL neurons. By inhibiting rebound firing of VL neurons, Parkinson's disease can be treated or prevented.

BRIEF DESCRIPTION OF THE DRAWINGS

The patent or application file contains at least one drawing executed in color. Copies of this patent or patent application publication with color drawing(s) will be provided by the office upon request and payment of the necessary fee.

The application of the preferred embodiments of the present invention is best understood with reference to the accompanying drawings, wherein:

FIG. 5 illustrates the time-series images of WT mice during the horizontal bar test (left) and the average latency to release with no photostimulation (OFF) and 20 Hz photostimulation (right).

FIG. 6(A) illustrates the multi-unit activity of VL neurons (VL), the local field potentials in primary motor cortex (M1-LFP), and the EMG recordings from muscles (neck and arm EMG) after photostimulation (5 Hz, 50 ms pulse width) in WT mice; and FIG. 6(B) illustrates the same data in CaV3.1-KO mice (Asterisks: absence of muscle responses; Red arrows: activated MUA signals; Blue bars: time for light-On).

FIG. 7 illustrates the comparison of the average firing of multi-unit activity (MUA) or VL neurons before and during 473 nm light (1 Hz, 50-ms pulse width) between WT and $Ca_v3.1$-KO mice.

FIG. 8(A), FIG. 8(B), FIG. 8(D) and FIG. 8(E) illustrate the raster plots of multi-unit activity (MUA) and single-unit activity (SUA) of VL neurons before and after photostimulation with 473 nm light (1 Hz, 50-ms pulse width) in WT (FIG. 8(A) and FIG. 8(D)) and CaV3.1-KO (FIG. 8(B) and FIG. 8(E)) neurons (Each horizontal row shows an individual trial in the VL area.).

FIG. 8(C) illustrates the earlier onset and higher rebound firing rate in WT than KO neurons.

FIG. 8(F) illustrates the no significant differences in peak firing rates between genotypes (Red arrows: time of peak firing; Gray dotted line: baseline firing rate).

FIG. 11(A) illustrates the IPSPs evoked by 488 nm photostimulation of GPm inputs recorded in patch-clamped VL neurons, and FIG. 11(B) and FIG. 11(C) illustrate the similar probability of IPSP response FIG. 11(B) and the similar mean IPSP amplitudes FIG. 11(C) in WT and CaV3.1-KO mice following photostimulation.

FIG. 12(A) and FIG. 12(B) illustrate the rebound firing in VL neurons of WT mice before and after $Ni^{2+}$ treatment, and FIG. 12(C) and FIG. 12(D) illustrate the raster plots of action potentials after hyperpolarization by injection in thalamic slices from WT mice before and after $Ni^{2+}$ treatment (Red arrows: First spike after hyperpolarization).

FIG. 15(A) illustrates the representative rebound slope, and FIG. 15(B) illustrates the differences in membrane potential before and after $Ni^{2+}$ treatment in brain slices (WT: black; KO: red).

FIG. 16(A) illustrates the induction of rebound firing dependent on the pulse width (5, 25 or 50 ms) of photostimulation in WT; and FIG. 16(B) illustrates the same results in CaV3.1-KO (Arrows: induction of rebound firing (red) and muscle responses (blue); Asterisks: absence of rebound firing and muscle responses).

FIG. 17(A) illustrates the photostimulation-induced akinesia-like motor abnormalities and tremor-like motor abnormalities in behaving WT; FIG. 17(B) illustrates the same data in CaV3.1-KO mice.

FIG. 19 illustrates the sparse expression of green light-responsive eNpHR3.0 in VL somata (Green: eNpHR3.0; Blue: DAPI).

FIGS. 20(A), 20(B) and 20(C) illustrate the representative EMG responses to photoinhibition of VL somata with photoactivation of GPm-VL synapses. FIG. 20(A): Photoactivation of GPm-VL synapses with no photoinhibition of VL somata (None); FIG. 20(B): Photoinhibition of VL somata within 200 ms GPm-VL pathway photoactivation (Early); and FIG. 20(C): Photoinhibition of VL somata during 250-500 ms after GPm-VL pathway photoactivation (Late).

FIG. 27(A) illustrates the percentage of time spent moving during light-ON (10 s) and light-OFF (10 s) periods in SPR-KO mice, and FIG. 27(B) and FIG. 27(C) illustrate the photoinhibition of GPm-VL synapses in SPR-KO mice suppresses movement initiation delay FIG. 27(B) and akinesia FIG. 27(C).

FIG. 29(A) illustrates the reduction of tremor activity during photoinhibition, FIG. 29(B) illustrates the comparison of the tremor score between ethosuximide treated (ETX) and saline treated (Sal) control mice, and FIG. 29(C) illustrates the comparison of the tremor score between the mice with VL-specific CaV3.1 knockdown (Sh3.1) and the control mice with scramble virus (Scr).

DESCRIPTION OF THE PREFERRED EMBODIMENTS

Figure 1A:
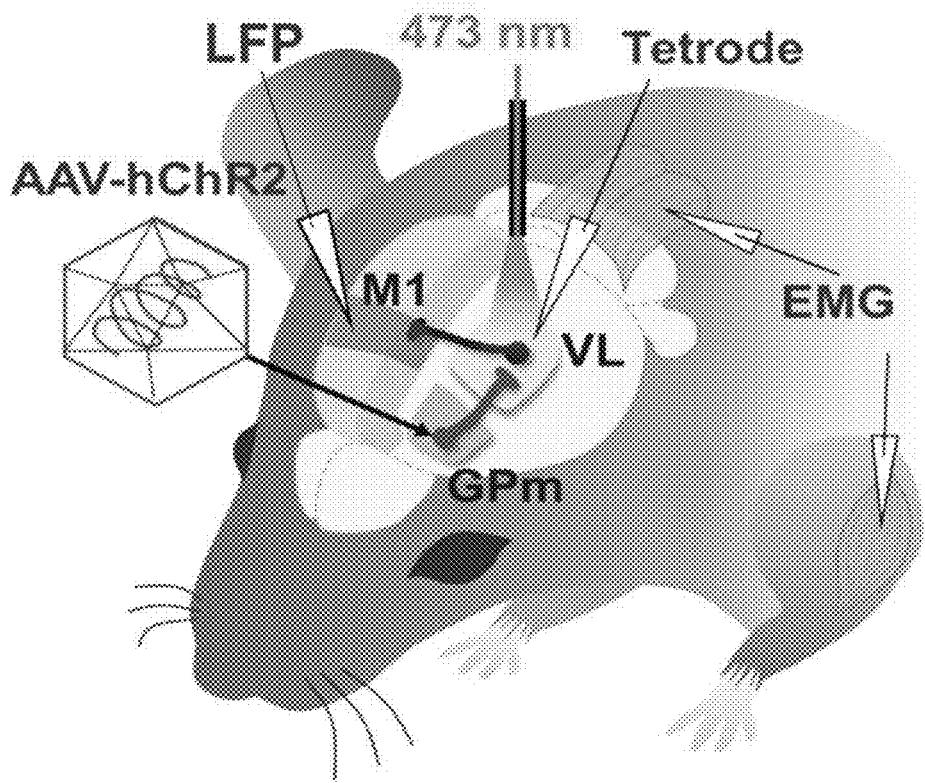
FIG. 1(A) illustrates the experimental scheme for photostimulation of GPm-VL synapses and recording activities from VL neurons and body muscles.

Hereinafter, the present invention is described in detail.

The present invention provides a method for treating Parkinson's disease comprising the step of inhibiting rebound firing of ventrolateral thalamus (VL) neurons.

The rebound firing of VL neurons above is induced by the inhibitory input transmitted from the medial globus pallidus (GPm), and the rebound firing can be inhibited by photoinhibition of VL or GPm neurons.

To inhibit the rebound firing of VL neurons, a polynucleotide encoding a halorhodopsin protein or a vector containing the polynucleotide above can be introduced in ventrolateral thalamus (VL) or medial globus pallidus (GPm) neurons of a subject having Parkinson's disease.

The said halorhodopsin protein responses to light to flow chloride into cells to cause hyperpolarization, indicating it plays a role as an ion pump. The halorhodopsin protein is composed of the amino acid sequence represented by SEQ ID NO: 1.

The said halorhodopsin protein preferably responses to light to flow chloride ions (Cl$^-$) into cells to cause hyperpolarization therein and accordingly inhibits the rebound firing of VL neurons. Any protein that can inhibit the rebound firing of VL neurons by responding to light can be used herein without limit. Particularly, the protein can be iC$^{++}$ or ArchT, but not always limited thereto.

The said halorhodopsin protein can include not only a wild type protein having an activity of a chloride ion pump but also a functional homologue displaying an activity of a chloride ion pump with at least 90% amino acid homology.

In this invention, the term "homology" indicates the level of similarity to the amino acid sequence of a wild type protein. The halorhodopsin protein of the present invention comprises an amino acid sequence having at least 70% homology, preferably at least 90% homology, and more preferably at least 95% homology with the wild type amino acid sequence represented by SEQ ID NO: 1. The comparison of homology can be performed by observing with the naked eye or by using a comparison program that is easy to purchase. The commercially available computer program can calculate homology between two or more sequences as %, and homology (%) can be calculated for adjacent sequences.

The said halorhodopsin protein can include an amino acid sequence variant thereof as long as it retains the activity of a chloride ion pump. The variant herein indicates the protein having a different sequence from the natural amino acid sequence due to deletion, insertion, non-conservative or conservative substitution of one or more amino acid residues, or a combination thereof.

Such a variant includes a functional homologue having an equivalent activity to the wild type or a modified protein having modifications that increase or decrease physicochemical properties. Preferably, the protein herein is a variant in which the physicochemical properties are modified. For example, the variant herein has the increased structural stability against the external environment including physical factors such as temperature, moisture, pH, electrolyte, reducing sugar, pressurization, drying, freezing, interfacial tension, light, repetition of freezing and thawing and high concentration, and chemical factors such as acid, alkali, neutral salt, organic solvent, metal ion, oxidation-reduction agent, and protease. It can also be a variant with the increased activity due to the modification in the amino acid sequence.

The said halorhodopsin protein can be directly isolated from living organisms, chemically synthesized, or obtained by using genetic recombination techniques. In the case of isolating the halorhodopsin protein directly from living organisms, the isolation and purification of the halorhodopsin protein contained in cells can be performed by various generally known methods. In the case of synthesizing the protein chemically, a polypeptide synthesis method well known to those in the art can be used. The Polypeptide can be prepared by using the conventional stepwise liquid or solid phase synthesis, fractional condensation, F-MOC or T-BOC chemical method. In the case of using genetic recombination techniques, the polynucleotide (nucleic acid) encoding the halorhodopsin protein is inserted in a proper expression vector, which is introduced in a host cell for transfection, and then the host cell is cultured to express the halorhodopsin protein, followed by collecting the protein from the host cell. The protein is expressed in selected host cells and then purified by the conventional biochemical separation techniques such as treatment with a protein precipitant (salting-out), centrifugation, ultrasonic disruption, ultrafiltration, dialysis, molecular sieve chromatography (gel filtration), adsorption chromatography, ion exchange chromatography, and affinity chromatography. To separate the protein with high purity, those methods are used in combination.

The polynucleotide encoding the halorhodopsin protein can be composed of the nucleotide sequence represented by SEQ ID NO: 2, or can be a polynucleotide in which one or more nucleotide sequences capable of encoding the active halorhodopsin protein are substituted, deleted, or inserted. The polynucleotide in which one or more nucleotide sequences are substituted, deleted, or inserted can have at least 70% homology, preferably at least 80% homology, and more preferably at least 90% homology with the polynucleotide represented by SEQ ID NO: 2.

The vector containing the polynucleotide above can contain a cloning origin, a promoter, a marker gene, and a translation regulatory element. The said vector can be a gene construct comprising an essential regulatory element operably linked thereto in order to express the gene insert so that a target protein can be expressed in proper host cells.

The vector containing the polynucleotide above can be selected from the group consisting of a linear DNA vector, a plasmid DNA vector, and a recombinant viral vector. The recombinant viral vector can be selected from the group consisting of retrovirus, adenovirus, adeno-associated virus, and lentivirus. In a preferred embodiment of the present invention, the vector containing the polynucleotide is preferably adeno-associated virus, but not always limited thereto.

The vector containing the polynucleotide can be introduced in ventrolateral thalamus (VL) or medial globus pallidus (GPm) neurons via one of the methods selected from the group consisting of transfection, electroporation, transduction, microinjection, and ballistic introduction. According to an embodiment of the present invention, transfection is most preferably used but not always limited thereto.

The method of the present invention can additionally include a step of irradiating green light to a subject introduced with the halorhodopsin protein, the polynucleotide encoding the halorhodopsin protein, or the vector containing the polynucleotide above.

The green light above has a wavelength of 480 to 550 nm, and preferably 500 to 550 nm. According to an embodiment of the present invention, the green light can have a wavelength of 532 nm.

The step of irradiating green light is to irradiate postsynaptic VL neurons.

In a preferred embodiment of the present invention, medial globus pallidus (GPm) neurons were infected with the adeno-associated virus (AAV) vector containing channelrhodopsin-2 (hChR2) gene and photostimulated to investigate the effect of inhibitory input of the basal ganglia (BG) on the thalamus. As a result, it was confirmed that the GPm-VL circuit plays an important role in the suppression of mouse locomotion (see FIGS. 1 and 2).

To examine whether the GPm-VL circuit affects the generation of motor signals, electromyography was performed. As a result, it was confirmed that the medial globus pallidus (GPm) inhibitory input to the VL alone is sufficient to trigger signals for muscle contraction, potentially leading to various motor responses, including suppressed locomotor activity, tremor, and rigidity, and the magnitude of this activity varied with the frequency of photostimulation (see FIGS. 3~5).

The present inventors also observed the activity of neurons in VL and motor cortex (M1), as well as the muscle activity during photostimulation of the GPm-VL input. As a result, it was confirmed that the activation of GPm-VL inhibitory synapses induces rebound firing of VL neurons, which stimulates the motor cortex (M1) (see FIG. 6).

Figure 9:
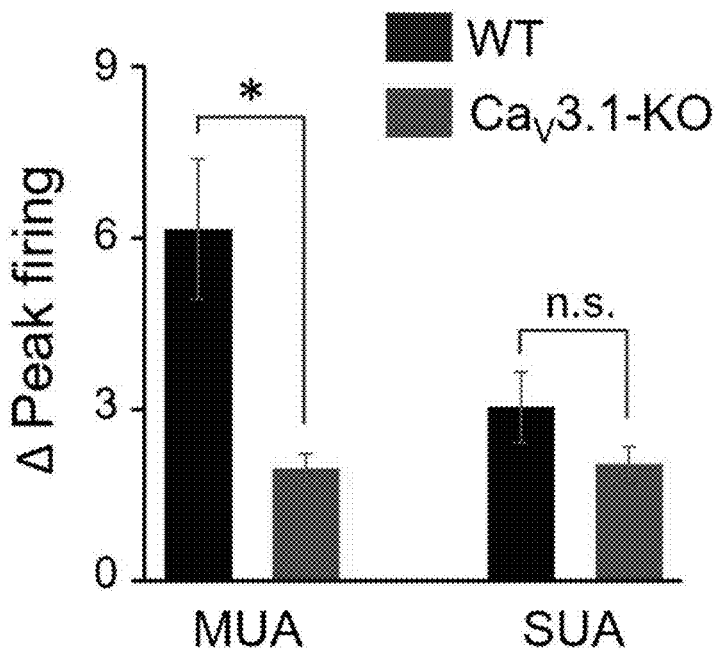
FIG. 9 illustrates the fold changes in peak firing rate after inhibition measured using SUA and MUA.

The present inventors also investigated the time course of action potential firing in VL neurons in response to photostimulation of GPm-VL inputs. As a result, VL neurons evoked a surge of rebound firing within 200 ms of the post-inhibitory period and the early-onset surge of rebound firing seems to depend on the number VL neurons (see FIGS. 8-10).

The present inventors designed an optogenetic experiment and performed in which halorhodopsin (eNpHR3.0) was expressed in the VL to facilitate photoinhibition of VL neurons while channelrhodopsin-2 (hChR2) was expressed in the medial globus pallidus (GPm) to allow photostimulation of GPm inhibitory inputs to the VL. As a result, it was confirmed that the photoactivation of GPm-VL inputs robustly induced muscular contractions, and this motor response was abolished by postsynaptic photoinhibition during the early (<200 ms) post-inhibitory period (see FIGS. 18-21). It was also confirmed that the number of neurons that evoke rebound firing during the early post-inhibitory period controls the amount of excitatory output from the VL.

The present inventors also confirmed that hypokinesia caused by photostimulation of GPm-VL inputs was efficiently restored by photoinhibition of VL neurons after the photostimulation of GPm-VL inputs (see FIG. 22).

Figure 23A:
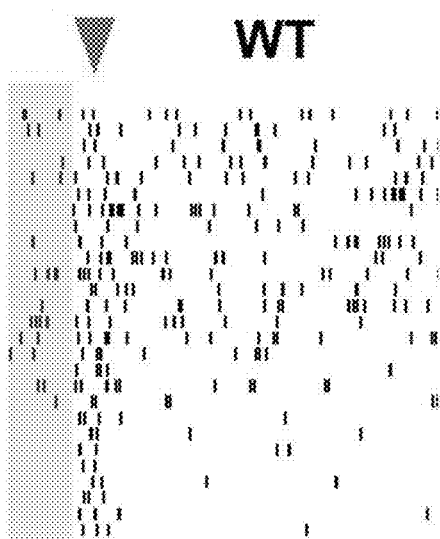
FIG. 23(A) illustrates the raster plots depicting increased spiking activity of VL neurons in WT and FIG. 23(B) illustrates the same data in SPR-KO mice following spontaneous inhibitory events (Pink box: the 50 ms epoch preceding the spontaneous inhibitory event; Red arrows: rebound firing after the spontaneous inhibitory event).
Figure 23B:
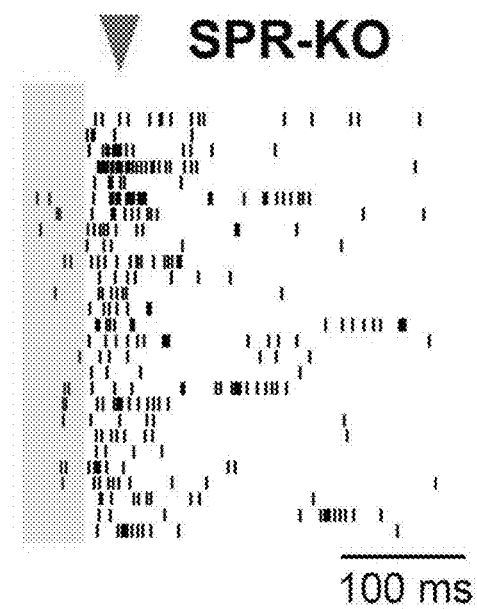

The present inventors constructed a mouse model of dopamine deficiency (SPR-KO) exhibit Parkinson's disease like motor abnormalities, followed by investigation of spontaneous rebound firing. As a result, it was confirmed that the dopamine-deficiency induced inhibition appears to evoke rebound firing in a PD-like mouse model (see FIGS. 23 and 24).

The present inventors induced the expression of halorhodopsin in the medial globus pallidus (GPm) of a mouse model of dopamine deficiency (SPR-KO), followed by photoinhibition of GPm inputs to VL. As a result, it was confirmed that such photoinhibition reduced rebound firing (see FIGS. 25 and 26).

The present inventors induced the expression of halorhodopsin in the medial globus pallidus (GPm) of a mouse model of dopamine deficiency (SPR-KO), followed by photoinhibition of GPm inputs to VL. As a result, the locomotion latency and akinesia were recovered and the muscular rigidity and tremor were reduced (see FIGS. 27-29). Therefore, it was confirmed that the GPm inputs could regulate rebound firing of VL neurons in a mouse model of dopamine deficiency (SPR-KO).

Figure 30:
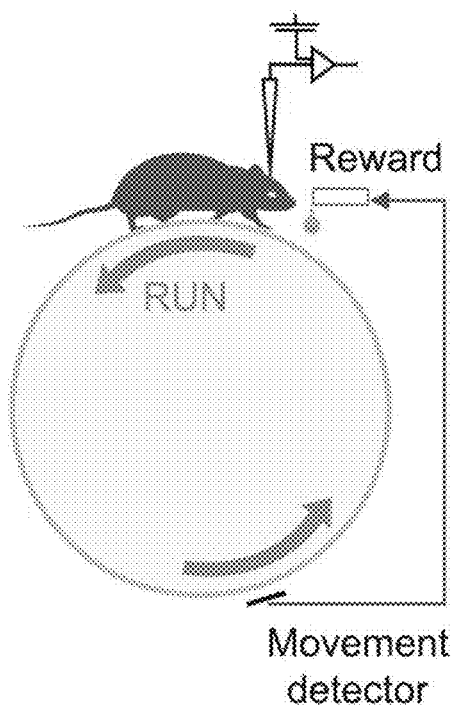
FIG. 30 illustrates the schematic depiction of the experimental setup for recording VL thalamic activity during natural resting-running (Nogo-Go or Go-Nogo) transitions.

The present inventors further confirmed that the spontaneous rebound firing in WT mice involved in a reduction in motor activity and the post-inhibitory excitation stabilized 'standstill' by inducing sufficient muscle tension. In the meantime, the inventors also confirmed that the excessive rebound firing in a mouse model of dopamine deficiency (SPR-KO) could cause pathological conditions that interfere with voluntary motor control, such as akinesia, rigidity, and tremor (see FIGS. 30-32).

Therefore, rebound firing of VL neurons can be inhibited by irradiating green light after the introduction of a halorhodopsin protein, a polynucleotide encoding the halorhodopsin protein or a vector containing the polynucleotide above into VL or GPm neurons, by which Parkinson's disease can be treated or prevented.

To inhibit rebound firing of VL neurons, a T-type $Ca^{2+}$ channel blocker can be treated to the ventrolateral thalamus (VL) of a subject having Parkinson's disease. The rebound firing of VL neurons is mediated by the activation of a T-type $Ca^{2+}$ channel. Thus, the rebound firing can be inhibited by inhibiting the T-type $Ca^{2+}$ channel.

In this invention, the "T-type $Ca^{2+}$ channel blocker" indicates a substance that can selectively inhibit the function of a T-type calcium ion channel, which is exemplified by a peptide, a protein, a nucleic acid, a non-peptide compound, a synthetic compound, a fermentation product, a cell extract, a plant extract, an animal tissue extract or plasma. These compounds can be novel compounds or well-known compounds. These substances can also include salts.

The salts of the candidate substances herein include salts of physiologically acceptable acids (e.g., inorganic acid) or bases (e.g., organic acid), among which physiologically acceptable acid addition salts are preferred. For example, salts of inorganic acids (e.g., hydrochloric acid, phosphoric acid, hydrobromic acid, or sulfuric acid) or organic acids (for example, acetic acid, formic acid, propionic acid, fumaric acid, maleic acid, succinic acid, tartaric acid, citric acid, malic acid, oxalic acid, benzoic acid, methanesulfonic acid, or benzenesulfonic acid) can be used.

The said T-type $Ca^{2+}$ channel blocker can be selected from the group consisting of mibefradil, tetramethrin, ethosuximide, SUN-N8075 (Daiichi Suntory Biomedical Research Co Ltd, Japan), efonidipine, $Ni^{2+}$ (divalent ion of nickel), $Y^{3+}$ (trivalent ion of yttrium), $La^{3+}$ (trivalent ion of lanthanum), $Ce^{3+}$ (trivalent ion of cerium), $Nd^{3+}$ (trivalent ion of neodymium), $Gd^{3+}$ (trivalent ion of gadolinium), $Ho^{3+}$ (trivalent ion of holmium), $Er^{3+}$ (trivalent ion of erbium), $Yb^{3+}$ (trivalent ion of ytterbium), U-92032 (7-[[4-[bis(4-fluorophenyl)methyl]-1-piperazinyl]methyl]-2-[(2-hydroxyethyl)amino]4-(1-methylethyl)-2,4,6-cycloheptatrien-1-one, Xu and Lee, J. Pharmacol. Exp. Ther., 1994, 268: 1135-1142), penfluridol, fluspirilene, and valproate, but not always limited thereto. In this invention, ethosuximide is preferably used as the T-type $Ca^{2+}$ channel blocker.

The T-type $Ca^{2+}$ channel blocker can inhibit the expression of a subtype gene that constitutes the T-type $Ca^{2+}$ channel. Particularly, the T-type $Ca^{2+}$ channel blocker above can be an expression inhibitor of one of those genes selected from the group consisting of $\alpha1G(Ca_V3.1)$, $\alpha1H(Ca_V3.2)$, and $\alpha1I(Ca_V3.3)$. Herein, the blocker is preferably an expression inhibitor of $Ca_V3.1$.

The said $Ca_V3.1$ gene can be composed of the nucleotide sequence represented by SEQ ID NO: 3.

The $Ca_V3.1$ gene expression inhibitor can be any substance capable of inhibiting the expression or activity of CaV3.1 gene, and can be selected from the group consisting of siRNA, shRNA, and miRNA complementarily binding to mRNA of CaV3.1 gene, but not always limited thereto. Preferably, the said shRNA can be composed of the nucleotide sequence represented by SEQ ID NO: 4.

Variants of the nucleotide sequence are included in the scope of the present invention. Particularly, a nucleotide sequence having the homology of at least 70% with the said nucleotide sequence, preferably at least 80% of homology, more preferably at least 90% of homology, and most preferably at least 95% of homology with the said nucleotide sequence can be included herein. The "% of sequence homology" with the polynucleotide is ascertained by comparing the comparison region with two optimally aligned sequences. Some of the polynucleotide sequences in the comparison region can include additions or deletions (i.e., gaps) relative to the reference sequence (without addition or deletion) for the optimal alignment of the two sequences.

The said siRNA, shRNA, or miRNA can be inserted in a vector. The vector herein can be selected from the group consisting of a linear DNA vector, a plasmid DNA vector, and a recombinant viral vector. The recombinant viral vector can be selected from the group consisting of retrovirus, adenovirus, adeno-associated virus, and lentivirus. In a preferred embodiment of the present invention, the vector containing siRNA, shRNA, or miRNA is preferably lentivirus, but not always limited thereto.

The vector containing siRNA, shRNA, or miRNA can be introduced in VL neurons by one of those methods selected from the group consisting of transfection, electroporation, transduction, microinjection, and ballistic introduction. According to an embodiment of the present invention, transfection is most preferably used, but not always limited thereto.

In a preferred embodiment of the present invention, GPm inputs were photostimulated by using the mice lacking the $Ca_V3.1$ gene ($Ca_V3.1$-KO) that encodes the α1 subunit of T-type $Ca^{2+}$ channels. As a result, VL neurons showed robust inhibition but significantly diminished rebound firing, compared with WT neurons, and showed lower correlations with both motor cortex (M1) and muscular activity (see FIGS. 6 and 7). Therefore, it was confirmed that GPm-VL inhibitory synapses induced excitatory motor signals via activating T-type $Ca^{2+}$ channels The present inventors also investigated the time course of action potential firing in VL neurons in response to photostimulation of GPm-VL inputs. As a result, VL neurons evoked a surge of rebound firing within 200 ms of the post-inhibitory period. In contrast, $Ca_V3.1$-KO neurons lacked this early-onset rebound firing. Therefore, it was confirmed that the early-onset surge of rebound firing depended on the number VL neurons (see FIGS. 8-10).

Figure 14:
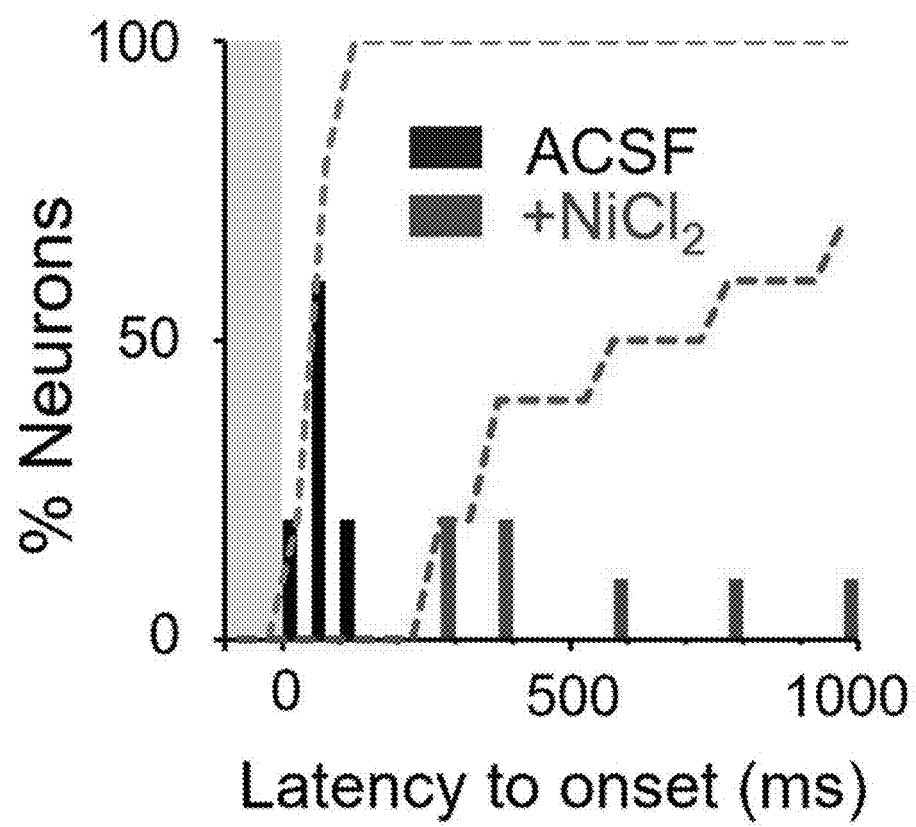
FIG. 14 illustrates the distribution of neurons classified by latency to first-spike onset after photostimulation (Black and red dotted lines show cumulative response probability by latency to first-spike onset).

The present inventors also confirmed that WT neurons reproducibly exhibited single spikes soon after the end of hyperpolarization, while the early-onset spikes were delayed by blocking T-type $Ca^{2+}$ channels with $Ni^{2+}$ (see FIGS. 12 and 14). Therefore, it was confirmed that rapid recovery of membrane potential in VL neurons after inhibition was dependent on $Ca^{2+}$ influx through the $Ca_V3.1$ channel. It was also confirmed that this rapid recovery facilitated induction of rebound firing from many VL neurons within a narrow time window (<200 ms), thus yielding a higher excitatory output from the thalamus.

The present inventors also confirmed that significant rebound firing of VL neurons, decreased locomotor activity and tremor-like behaviors were observed in WT mice after photostimulation. In the meantime, rebound firing of VL neurons and muscular responses were not observed in $Ca_V3.1$-KO mice after photostimulation. It was also confirmed that $Ca_V3.1$-KO mice were resistant to the generation of multiple motor abnormalities (see FIGS. 16 and 17). These results strongly suggest that the early-onset rebound firing within 200 ms after inhibition was mediated by $Ca_V3.1$ and acted as the thalamic motor signal.

The present inventors measured the spontaneous rebound firing in dopamine-deficient SPR-KO mice showing Parkinson's disease like motor impairment. As a result, it was confirmed that the dopamine-deficiency induced inhibition caused to evoke rebound firing (see FIGS. 23 and 24).

In a preferred embodiment of the present invention, dopamine-deficient SPR-KO mice were treated with ethosuximide. As a result, spontaneous rebound firing of VL neurons was reduced. This result indicated that GPm inhibitory input mediated rebound firing in the VL via T-type $Ca^{2+}$ channels in a dopamine-deficient state (see FIGS. 26(B) and (C)).

The present inventors treated dopamine-deficient SPR-KO mice with ethosuximide. As a result, rebound firing of VL neurons was reduced (see FIG. 26(C)) and the abnormal motor functions were alleviated (see FIG. 29(B)).

In a preferred embodiment of the present invention, the CaV3.1 gene was knocked-down with shRNA targeted to the dopamine-deficient mouse model (SPR-KO). As a result, rebound firing of VL neurons was reduced and the abnormal motor functions were alleviated (see FIG. 29(C)). Therefore, it was confirmed that GPm-inputs in the dopamine-deficient mouse model (SPR-KO) mediated rebound firing of VL neurons.

So, rebound firing of VL neurons can be inhibited by treating a T-type $Ca^{2+}$ channel blocker to VL neurons of a subject with Parkinson's disease and the inhibition of rebound firing of VL neurons can be efficient in treating or preventing Parkinson's disease.

The halorhodopsin protein, the polynucleotide encoding the halorhodopsin protein, the vector containing the polynucleotide, or the T-type $Ca^{2+}$ channel blocker of the present invention can additionally include any generally used carriers, diluents, excipients, or a combination of at least two of those. The pharmaceutically acceptable carrier can be any carrier that is able to deliver the active ingredient in human body without limitation, which is exemplified by the compounds described in Merck Index, $13^{th}$ ed., Merck & Co. Inc., such as saline, sterilized water, Ringer's solution, buffered saline, dextrose solution, maltodextrin solution, glycerol, ethanol, and a mixture comprising one or more of those components. If necessary, a general additive such as antioxidant, buffer, and bacteriostatic agent can be additionally added. The compound of the present invention can be formulated in different forms including aqueous solutions, suspensions and emulsions for injection, pills, capsules, granules or tablets by mixing with diluents, dispersing agents, surfactants, binders and lubricants. The compound can further be prepared in suitable forms according to ingredients by following the method represented in Remington's Pharmaceutical Science (Mack Publishing Company, Easton Pa., 18th, 1990).

The halorhodopsin protein, the polynucleotide encoding the halorhodopsin protein, the vector containing the polynucleotide, or the T-type $Ca^{2+}$ channel blocker of the present invention can contain one or more active ingredients having the same or similar functions to the above.

The halorhodopsin protein, the polynucleotide encoding the halorhodopsin protein, the vector containing the polynucleotide, or the T-type $Ca^{2+}$ channel blocker of the present invention can be administered orally or parenterally. The parenteral administration includes intracranial injection, intravenous injection, subcutaneous injection, intramuscular injection, intraperitoneal injection, and transdermal administration, etc.

The effective dose of the halorhodopsin protein, the polynucleotide encoding the halorhodopsin protein, the vector containing the polynucleotide, or the T-type $Ca^{2+}$ channel blocker of the present invention can be determined according to formulation method, administration method, age, body weight, gender, pathological condition, diet, administration time, administration pathway, bioavailability of active ingredients, inactivity rate, concomitant drug, excretion rate, and responsiveness. Particularly, the effective dose of the halorhodopsin protein, the polynucleotide encoding the halorhodopsin protein, the vector containing the polynucleotide, or the T-type $Ca^{2+}$ channel blocker of the present invention is 0.0001 ng/kg (body weight) to 200 mg/kg (body weight) per day.

The halorhodopsin protein, the polynucleotide encoding the halorhodopsin protein, the vector containing the polynucleotide, or the T-type $Ca^{2+}$ channel blocker of the present invention can be formulated by the method that can be performed by those in the art by using a pharmaceutically acceptable carrier and/or excipient in the form of unit dose or in multi-dose container. The formulation can be in the form of solution, suspension or emulsion in oil or water-soluble medium, extract, powder, granule, tablet or capsule. At this time, a dispersing agent or a stabilizer can be additionally included.

Practical and presently preferred embodiments of the present invention are illustrative as shown in the following Examples.

However, it will be appreciated that those skilled in the art, on consideration of this disclosure, may make modifications and improvements within the spirit and scope of the present invention.

The terms and abbreviations used herein have the following meanings. Where the abbreviation is not defined, it can be interpreted as a meaning commonly understood by those in the art.

Figure 1B:
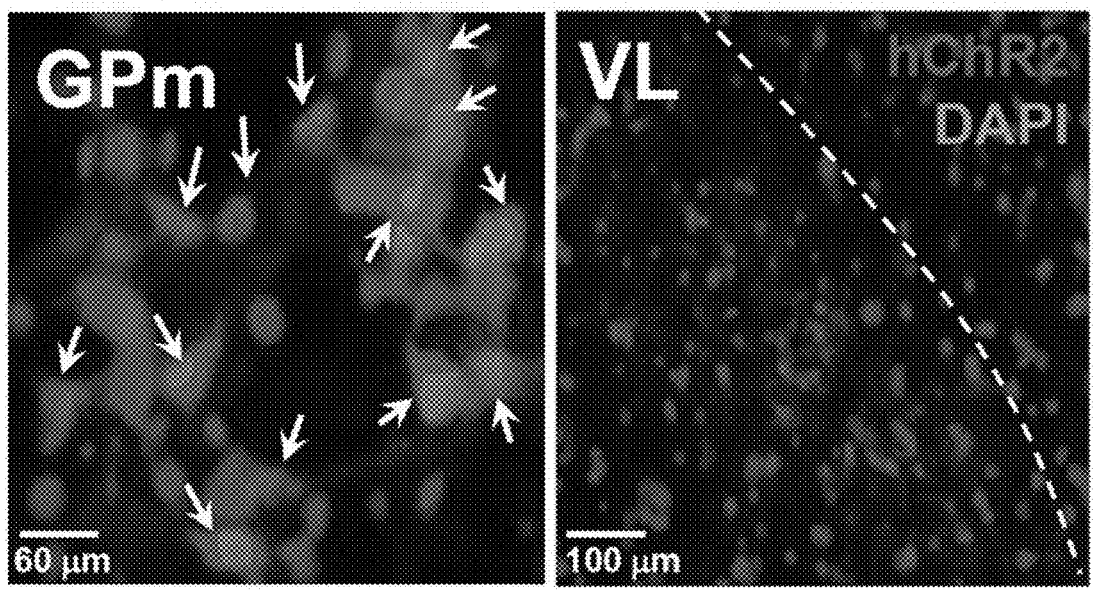
FIG. 1(B) illustrates the expression of the cation channel, ChR2, in GPm neurons (white arrows) and GPm axon terminals in the VL thalamus (Scale bars: 60 μm (GPm) and 100 μm (VL)).

5HTT-Cre: serotonergic transporter-Cre
AAV: adeno-associated virus
BG: basal ganglia
BH4: tetrahydrobiopterin
EF1α: elongation factor 1α
EMG: electromyography
ERP: event-related potentials
ETX: ethosuximide
GPm: medial globus pallidus
hChR2: channelrhodopsin-2
IPSP: inhibitory postsynaptic potentials
KO: knockout
LFP: local field potentials
LGN: lateral geniculate nucleus
M1: motor cortex
MLR: mesencephalic locomotor region
MUA: multi-unit activity
nRT: reticular thalamic nuclei
PD: Parkinson's disease
PPN: pedunculopontine nucleus
SNr: substantia nigra pars reticulata
SPR-KO: sepiapterin reductase knockout
STN: subthalamic nuclei
SUA: single-unit activity
VL: ventrolateral thalamus
WT: wild type
ZI: zona incerta Example 1: Construction of hChR2 Expressing Mouse Mice (WT, C57BL/6J, n=31) over 8 weeks old were used. Animal care and handling were performed according to the guidelines of the Animal Care and Use Committee of the Korea Advanced Institute of Science and Technology (KAIST, Korea). WT littermates were generated by mating heterozygous mutants (C57BL/6J background). SNr (substantia nigra pars reticulata) or GPm (medial globus pallidus) neurons was infected with an adeno-associated virus (AAV) vector harboring the gene for the light-activated cation channel channelrhodopsin-2 (hChR2) driven by the elongation factor 1α (EF1α) promoter (FIG. 1). The AAV2/1-EF1α-DIO-hChR2(H134R)-mCherry-WPRE (Cat# AV-1-20297P; titer: $5.36 \times 10^{12}$ gc/ml) was generated by the Vector Core Facility at the University of Pennsylvania (USA). For virus injection, all mice were anesthetized with avertin (20 mg/ml of tribromoethanol, 20 μl/g i.p.) and placed in a stereotaxic apparatus (David Kopf Instruments, USA). All injections were delivered at a rate of 0.1 μl/min. For expression of opsins in a limited target area, AAV9-CMV-CRE-EGFP and AAV2/1-EF1α-DIO-hChR2(H134R)-mCherry-WPRE was mixed at a 1:1 ratio. A total of 1.0 μl of virus mixture was injected into the GPm (−1.3 mm anteroposterior [AP]; −1.8 mediolateral [ML]; 4.25 dorsoventral [DV]). For expression of opsins in SNr (−3.3 mm AP; −1.4 ML; 4.9 DV), nRT (−0.7 mm AP; −1.3 ML; 3.5 DV) and ZI (−2.5 mm AP; −1.85 ML; 3.8 DV), the virus prepared in same titer was used with different volumes (0.8 μl, 0.4 μl, and 0.5 μl, respectively) according to the size of target area.

After injection, a fiberoptic probe with an external metal ferrule (200 μm diameter, 0.39 NA; Doric Lenses Inc., Canada) was implanted into the VL thalamus and fixed to the skull using Super-Bond (Sun Medical Co., Japan) and dental cement (Stoelting, USA). Coordinates for the VL thalamus were −1.0 mm AP, −1.1 ML, and 3.4 DV.

Example 2: Construction of $Ca_v3.1$-KO Mouse

The $Ca_v3.1$-KO mice of the present invention were the offsprings of the $Ca_v3.1$-KO mouse prepared according to the method described in Lack of the burst firing of thalamocortical relay neurons and resistance to absence seizures in mice lacking alpha(1G) T-type $Ca^{2+}$ channels (Kim et al., Neuron, 31: 35-45, 2011). The specific procedure for preparing the $Ca_v3.1$-KO mouse described in the literature is as follows.

A mouse cDNA of the $Ca_v3.1$ gene (cacna1G) sequence was isolated by RT-PCR and was used for isolating mouse genomic DNA clones containing the $Ca_v3.1$ locus from a phage library. The targeting vector containing 11.7 kb homologous fragments with double selection markers, neo and TK, was made and introduced into J1 embryonic stem cell lines. The targeted ES clones were identified by Southern blot analysis and used in the generation of germline chimeras, as previously described (Kim et al., 1997). Male germline chimeras were crossed with female C57BL/6J mice to obtain F1 heterozygotes ($Ca_v3.1+/−$) and these F1 were intercrossed to obtain homozygous mutant mice ($Ca_v3.1-/-$).

Example 3: Construction of Halorhodopsin Expressing WT Mouse

To design an optogenetic experiment, Halorhodopsin (eNpHR3.0), a light-dependent chloride pump, was expressed in WT mice to facilitate photoinhibition of VL neurons while hChR2 was expressed in GPm to allow photostimulation of GPm inhibitory inputs to the VL.

The AAV2/9-EF1α-DIO-eNpHR3.0-EYFP-WPRE (Cat# AV-9-26966P) was generated by the Vector Core Facility at the University of Pennsylvania (USA). For virus injection, all mice were anesthetized with avertin and placed in a stereotaxic apparatus. All injections were delivered at a rate of 0.1 μl/min. For expression of opsins in a limited target area, AAV9-CMV-CRE-EGFP and AAV2/9-EF1α-DIO-eNpHR3.0-EYFP-WPRE was mixed at a 1:1 ratio. A total of 1.0 pt of virus mixture was injected into the VL. Coordinates for the VL thalamus were −1.0 mm AP, −1.1 ML, and 3.4 DV.

After injection, a fiberoptic probe with an external metal ferrule was implanted into the VL thalamus and fixed to the skull using Super-Bond and dental cement. Coordinates for the VL thalamus were −1.0 mm AP, −1.1 ML, and 3.4 DV.

Histological analysis revealed that 50% of thalamic neurons express eNpHR 3.0 (FIG. 19).

Example 4: Construction of SPR-KO Mouse

The SPR-KO mice of the present invention were the offspring of the SPR-KO mouse prepared according to the method described in A murine model for human sepiapterin-reductase deficiency (S. Yang et al., Am. J. Hum. Genet., 2006). The specific procedure for preparing the SPR-KO mouse described in the literature is as follows.

The mouse Spr gene encodes 261 aa and consists of three exons. Previously a phage clone containing the entire Spr gene from a 129/SvJ (129) mouse genomic DNA library was isolated. To construct a targeting vector, a 3.3-kb HindIII-SacI fragment including a part of exon 1 and a 3.8-kb SacI-HindIII fragment containing the exon 3 region were sequentially inserted into the XhoI and XbaI sites, respectively, of the pPNT vector. The phosphoglycerate kinase (PGK)-neomycin cassette replaced a portion of exon 1, intron 1, and the entire exon 2 encoding the short-chain dehydrogenase/reductase domain. After electroporation of the linearized construct, G418-resistant and 1-(2-deoxy-2-fluoro-1-(3-d-arabinofuranosyl)-5-iodouracil (FIAU)-resistant colonies were selected. Approximately 300 double-resistant colonies were screened by Southern-blot analysis using a 5' external probe. One of the three positive clones was microinjected into C57BL/6J (B6) blastocysts to generate chimeras, which were crossed with B6 mice to establish and maintain the Spr+/− mouse line on a mixed 129/B6 hybrid background. The genotype of offspring from the breeding of heterozygous mice was determined with PCR primer sets SprF1 (SEQ ID NO: 5; 5'-AAGTGGTGCTG-GCAGCCGCCGAT-3') and NeoP3 (SEQ ID NO: 6; 5'-CG-GTGCTGTCCATCTGCACGAGAC-3'), for detection of the mutant allele, and srex2F (SEQ ID NO: 7; 5'-CCTC-CATGCTCTGTTTGACT-3') and srex2R (SEQ ID NO: 8; 5'-GTTCCCCTCCTTGCCTAGC-3'), for detection of the wild-type allele. The genomic region amplified by the srex2F and srex2R primer set was deleted in the mutant allele, and thus no PCR amplification occurs for the Spr−/− mice.

The survival of SPR-KO mice was maintained by treating daily with BH4 (Schircks Laboratories, Switzerland) in ascorbic acid (Sigma, USA) beginning on P2; N-acetyl-L-cysteine solution (Sigma) was used as a vehicle control. The dose of BH4 and vehicle are based on the method of Yang et al. (2006).

Example 5: Construction of Halorhodopsin Expressing SPR-KO Mouse

A SPR-KO mouse expressing halorhodopsin was constructed by injecting a virus expressing halorhodopsin into GPm according to the method described in Example 3 to the SPR-KO mouse constructed in Example 4.

Figure 25:
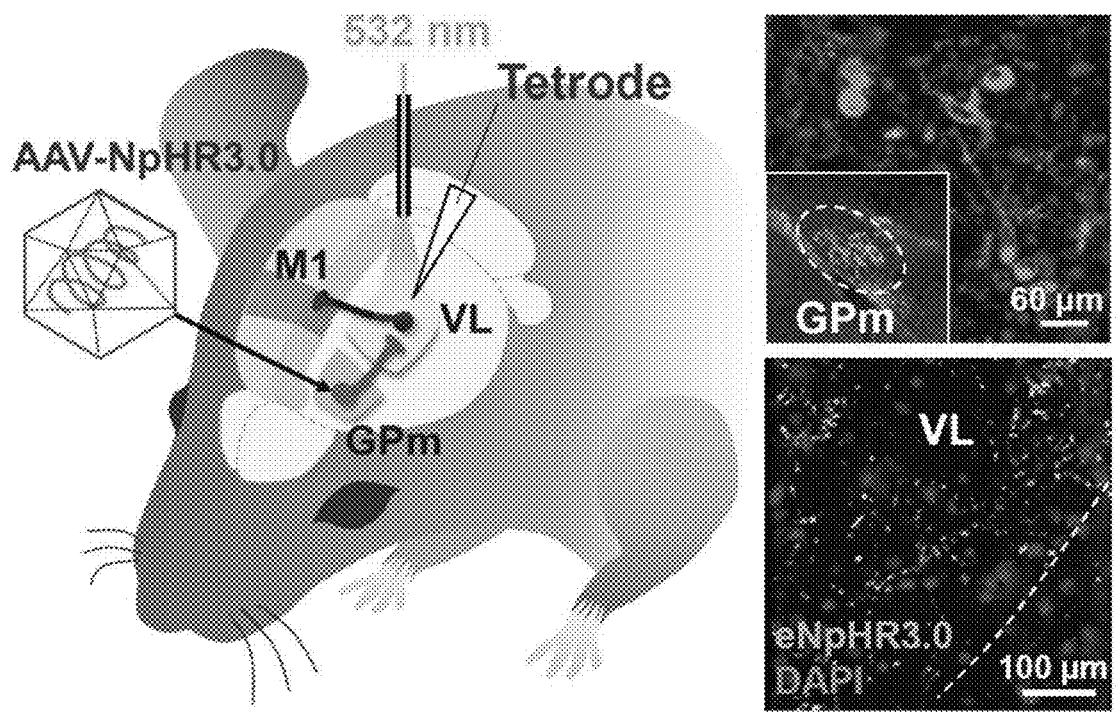
FIG. 25 illustrates the experimental scheme for photoinhibition of GPm-VL synapses while recording the activities of VL neurons in WT and SPR-KO mice and expression of eNpHR3.0 protein in somata of GPm neurons and their axon terminals in the VL thalamus.
Figure 26A:
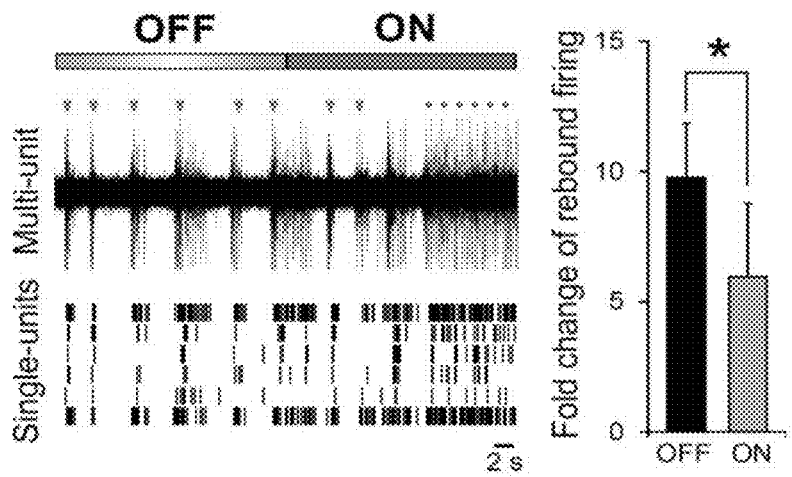
FIG. 26 (A) illustrates the multi-unit and single unit activity and Fold change in rebound spiking activity of VL neurons in SPR-KO mice following spontaneous inhibitory events before and after photoinhibition of GPm-VL synapses (Green rectangle: 532 nm continuous light for GPm photoinhibition).
FIG. 26(B) and FIG. 26(C) respectively illustrate the comparison of the VL neuronal activities and Comparison of the rebound firing in MUA and LFP before and after the ethosuximide treatment in SPR-KO mice.
Figure 26B:
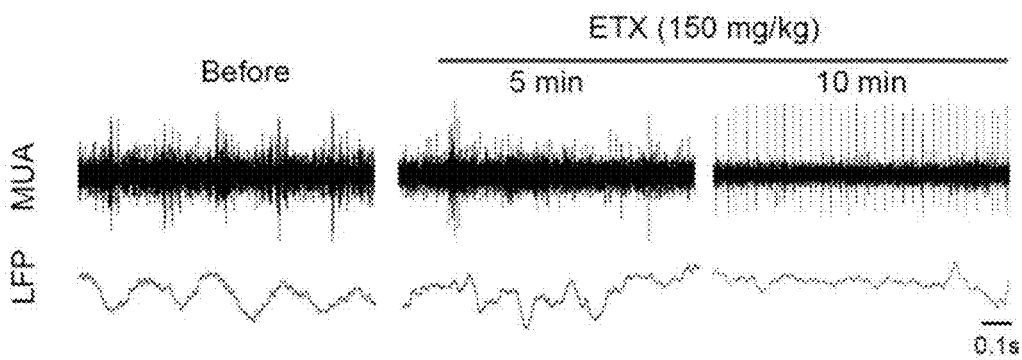
Figure 26C:
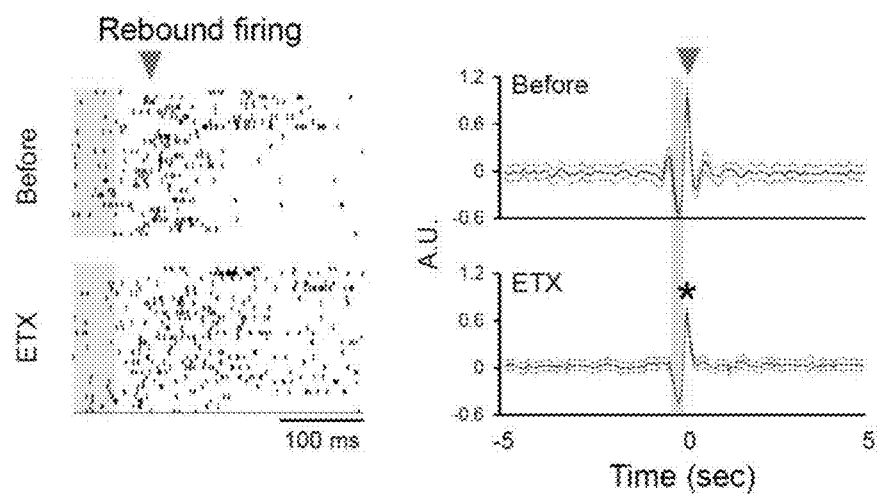

GPm was infected with an adeno-associated virus (AAV) harboring eNpHR3.0 under the control of the EF1α promoter. Illumination with green light (532 nm) was used to photoinhibit GPm inputs, and multi-unit recordings were used to determine the effects of photoinhibition (FIG. 25).

Example 6: Construction of SPR-KO Mouse Expressing shRNA Targeting $Ca_V3.1$ Gene The SPR-KO mouse prepared in Example 4 was injected with a virus expressing shRNA targeting CaV3.1 gene prepared according to the following method.

A lentiviral vector expressing short hairpin RNA (shRNA) to target the $Ca_V3.1$ T-type calcium channel was constructed as the paper by Kim et al. (2011). The recombinant lentiviral vectors were produced and concentrated commercially (Macrogen LentiVector Institute). The lentivirus titers of $2 \times 10^6$ transduction units/ml were used. The solution containing the viruses carrying the $Ca_V3.1$-shRNA or the scrambled control were injected into the right VL thalamus with Nanofil 33G blunt needles and a Nanofil syringe (World Precision Instruments) using a micro syringe pump (Eicom). 10 days after viral transduction, analyses were performed.

Experimental Example 1: Photoactivation of the GPm-VL Pathway Modulates Locomotion The effect of basal ganglia (BG) inhibitory input on the thalamus was examined.

In Example 1, GPm (medial globus pallidus), SNr (substantia nigra pars reticulata), ZI (zona incerta), or nRT (reticular thalamic nucleus) neurons were infected with an adeno-associated virus (AAV) vector harboring the gene for the light-activated cation channel channelrhodopsin-2 (hChR2) driven by the elongation factor 1α (EF1α) promoter (FIG. 1).

To determine the specific role of GPm-VL inputs, the axons of GPm neurons were photostimulated by illuminating (473 nm) the core area of the VL. For optogenetic stimulation experiments, 473 nm light was provided by a diode-pumped solid-state laser (CrystaLaser, USA) controlled by a pulse generator (Agilent, USA).

For analyses of fine movement and locomotion, mice were subjected to both cylindrical- and square chamber assays. First, mice were placed in a cylindrical glass chamber (diameter, 15; height, 20 cm) and allowed to explore the chamber and adjust to the fiber-optic cable for 1-3 min. Light stimuli (20 Hz, 5-ms pulses for 473 nm) were applied in 3-5 sessions, with each session lasting for 15-20 s. After the sessions, mice were placed directly in an acrylic chamber (25×28×22 cm) and allowed to explore for 1-3 min, and the same light stimulation sessions were repeated. The assay was performed between 1:00 PM and 6:00 PM in a dimly lit room and recorded with a camcorder at a sampling rate of 25 samples/s. The video recordings were analyzed using Etho-Vision XT 8.5 (Noldus Information Technology).

Figure 2A:
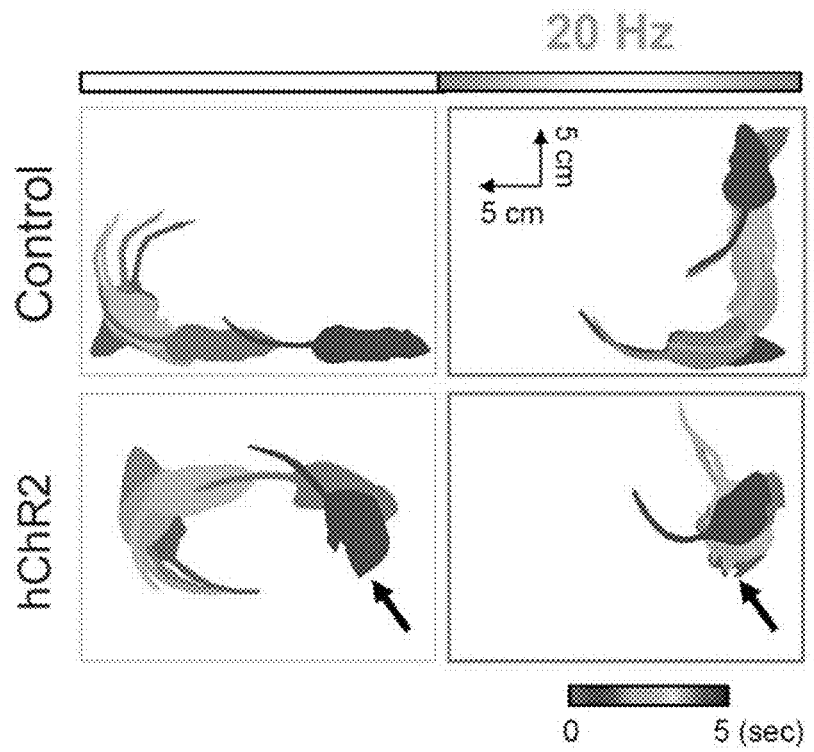
FIG. 2(A) illustrates the movement of the mouse before and after (blue rectangle) photostimulation on the GPm-VL synapse.
Figure 2B:
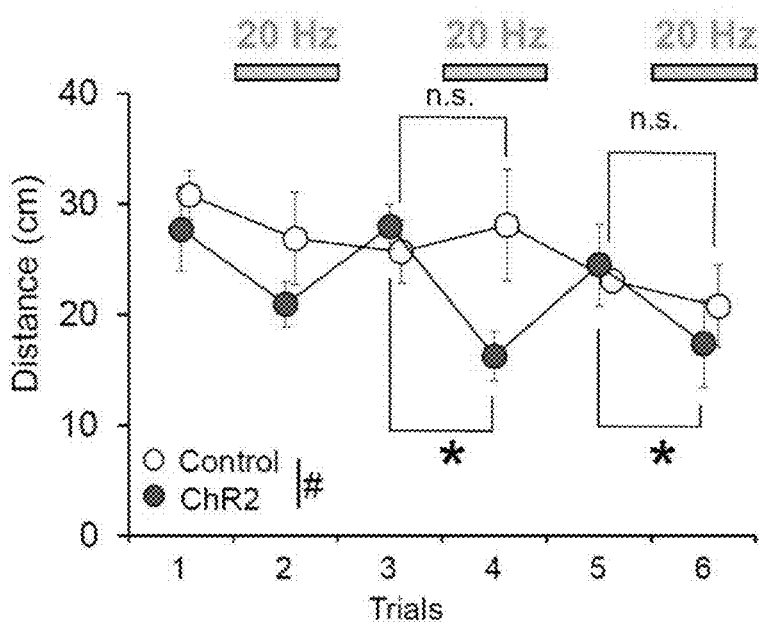
FIG. 2(B) illustrates the quantification of the photostimulation effect on locomotion (Blue bars: 15 s photostimulation (20 Hz, 5 ms pulse width)).

Compared to mice infected with control virus expressing mCherry only, hChR2 mice displayed significantly less spontaneous locomotor activity in response to VL photostimulation, indicating hypokinesia (FIG. 2). In contrast, photostimulation of VL inputs from SNr and other inhibitory inputs from the nRT or ZI neurons had no significant effects on locomotion (not shown). These results clearly indicate that the GPm-VL circuit is critical for the suppression of locomotion and plays a unique role compared to other inhibitory inputs to VL.

Experimental Example 2: Photoactivation of the GPm-VL Pathway Induces Motor Responses Through Muscular Contraction The present inventors examined whether the GPm-VL circuit affects the generation of motor signals. The electromyography (EMG) was applied to measure muscular activity (FIG. 1C).

<2-1> In Vivo Spike Recording in a Waking State

For implanting head-plate and EMG electrodes, WT mice were anesthetized with avertin and placed in a stereotaxic device. A custom-designed head-plate with a circular window (1 cm diameter) was implanted by cementing to the skull with Super-Bond and dental cement. For recording muscle activity of the forelimb, an EMG electrode was bilaterally implanted in the lateral part of the triceps brachii muscle. For recording muscle activity of neck muscles, two Teflon-coated tungsten EMG electrodes (A-M Systems Inc., USA) were implanted in the neck. All connectors were fixed to the head-plate with dental cement. All electrodes for EMG recordings were then connected to an electrode interface board (EIB-16; Neuralynx).

After at least a 3-d recovery period, mice were habituated for 15 min to the head-restrained conditions used for recording sessions, and recordings were performed the next day.

Three trials of 10 s optical stimulation, with a 50 s inter-trial interval, were performed. Three-trial sets of optical stimulation were repeated using the following conditions: 5-, 25-, 50- and 100-ms pulses at 1 and 5 Hz, and 5- and 25-ms pulses at 20 Hz. EMG was recorded with a Digital Lynx acquisition system (Neuralynx). Data were digitized at 30-5 kHz for EMGs.

To identify the activated EMG signals, EMG spikes above a threshold (2.5-3.5×SD of basal EMG amplitude) were extracted from raw EMG signals using Spike Extractor software (Neuralynx). Peri-event histograms at various frequencies were calculated using Neuroexplorer (Nex Technologies). For the frequency analysis of 20 Hz photostimulation-induced EMG activities, the power spectrogram was computed from rectified EMG signals using Neuroexplorer software. Representative traces in each frequency range were computed using the Butterworth filter in MATLAB (version R2013a; Mathworks, USA) software.

Figure 3:
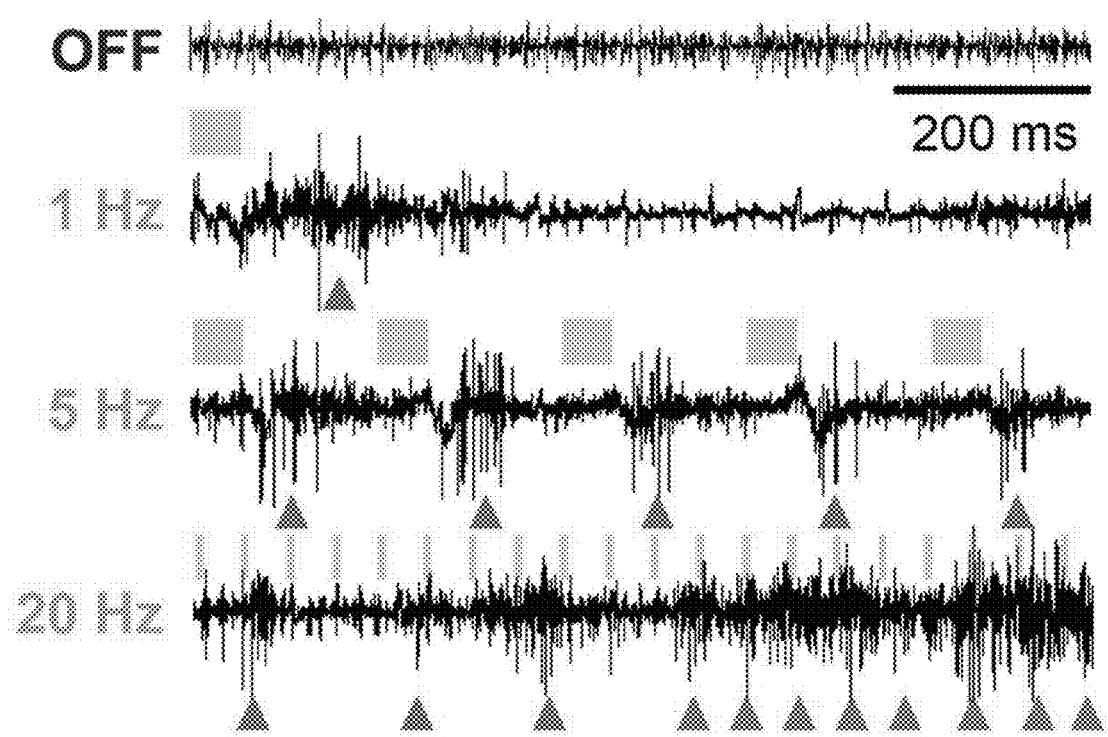
FIG. 3 illustrates the representative traces of photo-induced EMG signals in WT mice (Blue bars: Light stimulation (1 Hz, 50 ms pulse width; 5 Hz, 50 ms pulse width; 20 Hz, 5 ms pulse width); Green arrows: Slow muscle twitching; Red arrows: Rapid muscle twitching).
Figure 4:
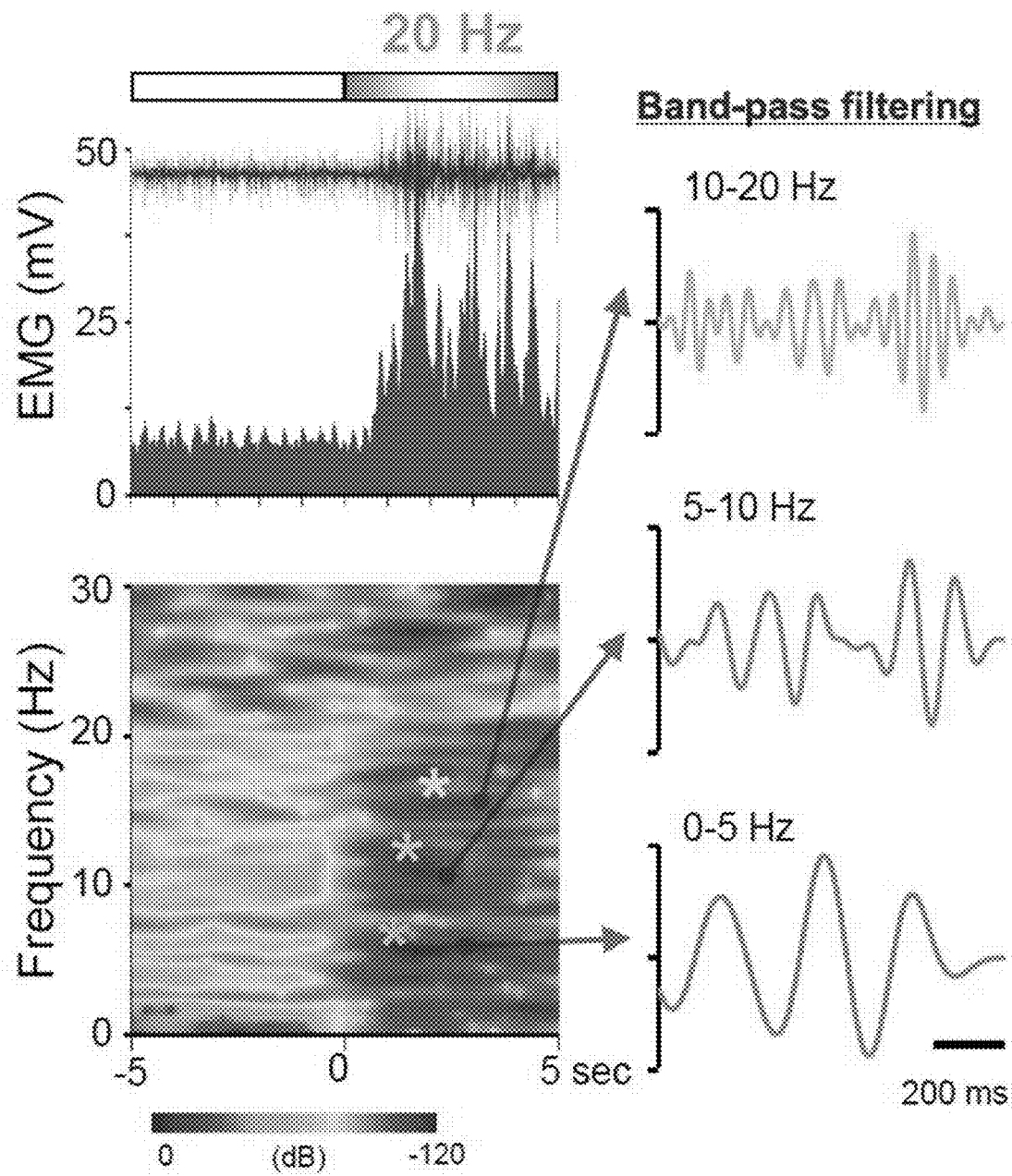
FIG. 4 illustrates the representative photo-induced EMG signal from a WT mouse (left) and band-pass filtered EMG activity in each frequency range (right) (Rectified EMG signals (filled line plot) showing photostimulation-induced muscle activity. The frequency distribution of EMG activity is presented as a pseudocolor spectrogram. Three color asterisks in the spectrogram indicate the frequency ranges with clear increases in EMG amplitude).

Shortly after photostimulation of GPm-VL inputs, muscle contractions occurred. The magnitude of this activity varied with the frequency of photostimulation (FIG. 3) and light pulse duration (not shown). Photostimuli at 1 Hz reliably evoked muscle twitches (FIG. 3). In contrast, low-frequency (5 Hz) trains of light flashes induced tremor-like activity at the same frequency (green arrowheads in FIG. 3) whereas high-frequency trains (20 Hz)—mimicking the frequency of GPm oscillations observed in PD—induced both high-frequency muscle activity (red arrowheads in FIG. 3, yellow EMG signals in FIG. 4) and low-frequency tremor activity (green arrowhead in FIG. 3, red and green EMG signals in FIG. 4).

<2-2> Rigidity Test

The high-frequency muscle activity may reflect muscular rigidity, a state of continuous contraction. To test the degree of rigidity, the ability of mice to hold onto a bar (FIG. 5) was examined.

The front paws of a mouse were positioned on a 2-mm horizontal wire bar 4 cm above the ground, and the latency to paw release was analyzed. Three trials were performed for each mouse, with each trial lasting for 1 min; the results for each mouse are presented as the average of the three trials. The test was performed between 12:00 PM and 6:00 PM.

During 20 Hz photostimulation, the latency of spontaneous bar release was significantly delayed compared to the performance observed without photostimulation, indicating rigidity (FIG. 5). These results signify that GPm inhibitory input to VL alone is sufficient to trigger signals for muscle contraction, potentially leading to various motor responses, including suppressed locomotor activity, tremor, and rigidity.

Experimental Example 3: GPm-VL Inputs Induce Inhibition and Rebound Firing in VL Neurons by Activating T-Type $Ca^{2+}$ Channels <3-1> Correlation of Neural and Motor Responses in WT Mice To identify the neural correlates of these motor responses, the activity of neurons in VL and motor cortex (M1), as well as muscle activity during photostimulation of the GPm-VL input were monitored (FIG. 6(A)).

VL multi-unit activity, EMGs, and cortical LFPs were recorded simultaneously in vivo following optical stimulation. For implanting head-plate and EMG electrodes, the electrodes were implanted according to the method described in Example <2-1>. For recording cortical LFPs, a tungsten wire (Cat. #796000; A-M Systems Inc.) was acutely implanted into the M1 cortex (0 mm AP, −1.0 ML, 1.0-1.5 DV) during preparation for the recording session. All electrodes for LFP and EMG recordings were then connected to an electrode interface board (EIB-16; Neuralynx).

After at least a 3-d recovery period, mice were habituated for 15 min to the head-restrained conditions used for recording sessions, and recordings were performed the next day. Mice were prepared for recordings by anesthetizing with isoflurane (1.5% in oxygen), after which their head-plate was fixed to a holder device. Holes were drilled in the skull above the right VL for multi-unit activity (1.0 mm AP, −1.0 ML), the M1 for LFPs (0 mm AP, −1.0 ML) and the temporal cortex for the ground electrode (2.0 mm AP, 2.0 ML); the dura was cleanly removed to allow insertion of electrodes. An optrode for recording VL multi-unit activity was fixed to a micromanipulator (Stoelting) and lowered into the VL thalamus. LFP and ground electrodes were localized in the M1 and temporal cortex, respectively, and fixed to the head-plate with cyano-acrylate (Loctite; Henkel, Germany). The holes were sealed with 1.5% liquid agar, and the mice were allowed to recover from the anesthesia. Recording sessions were started after the mice fully regained consciousness. VL neurons connected to the GPm were identified by delivering 50-ms-width light pulses at 1 Hz and observing VL neural activity every 100-150 mm in the VL region.

After light-responsive VL neurons were detected, basal neural activity was recorded for 5-10 min, and then three trials of 10 s optical stimulation, with a 50 s inter-trial interval, were performed. Three-trial sets of optical stimulation were repeated using the following conditions: 5-, 25-, 50- and 100-ms pulses at 1 and 5 Hz, and 5- and 25-ms pulses at 20 Hz. After each trial, the optrode was lowered 200-500 μm to detect another light-responsive VL neuron. When neuronal firing was detected, basal activity was recorded and optical stimulations were repeated. Upon completion of recordings, mice were sacrificed after making an electrolytic lesion (1 mA, 5 s) to confirm the anatomical location. Neural signals, including VL multi-unit activity, M1 LFPs and EMGs, were recorded with a Digital Lynx acquisition system (Neuralynx). Data were digitized at 32 kHz and band-pass filtered at 300-5 kHz for multi-unit activity, at 0.5-50 Hz for LFPs, and at 30-5 kHz for EMGs. TTL signals from the pulse generator were recorded concurrently with neural signals.

The light-induced neural activities were computed as the perievent firing rate histogram in 25-ms bins. To analyze the rebound firing (post-inhibitory activities) induced by photostimuli, the subset of multi- and single-units which showed both significant silencing was utilized during the light illuminations and firing increase over then the basal activity after the photostimuli. All analyses were performed using MATLAB (Mathworks, USA) and Neuroexplorer (Nex Technologies, USA) software.

Activation of GPm-VL inputs (blue bars in FIG. 6(A)) led to the expected inhibition of VL neurons during light flashes (FIG. 6(A)). However, at the end of each light flash, VL neurons showed a surge of action potentials (VL in FIG. 6(A)). This rebound firing was accompanied by increased activity in the motor cortex (M1), as evident from local field potentials (LFP in FIG. 6(A)), and muscle responses, indicated by enhanced EMG activity in neck and arm muscles (Neck-EMG and Arm-EMG in FIG. 6(A)). These results support the possibility that activation of GPm-VL inhibitory synapses induces rebound firing of VL neurons, which, in turn, stimulates the motor cortex and causes muscle contraction.

<3-2> Correlation of Neural and Motor Responses in $Ca_V3.1$-KO Mice

To determine the molecular basis underlying the rebound firing produced in VL neurons by GPm inputs, the same experiment as described in Example <3-1> was performed using the $Ca_V3.1$-KO mice constructed in Example 2. The $Ca_V3.1$ gene encodes the α1 subunit of T-type $Ca^{2+}$ channels known to be critical for inducing rebound burst firing in response to inhibition.

When GPm inputs were photostimulated in vivo, $Ca_V3.1$-KO neurons showed robust inhibition (FIG. 7) but significantly diminished rebound firing, compared with WT neurons (FIG. 6(B)). Remarkably, absolutely no muscular responses were observed (FIG. 6(B)) under various photostimulation conditions. The activity of VL neurons in $Ca_V3.1$-KO mice consistently showed lower correlations with both M1 and muscular activity, relative to WT neurons (FIG. 6). Based on these findings, GPm-VL inhibitory synapses induce excitatory motor signals via activating T-type $Ca^{2+}$ channels.

Experimental Example 4: The Motor Signal Depends on the Number of VL Neurons that Generate Rebound Firing in Response to Inhibition To gain further insight into how VL neurons induce motor signals in response to GPm inhibitory input, the time course of action potential firing in VL neurons from WT and $Ca_V3.1$ KO mice was analyzed in response to photostimulation of GPm input.

The activity of VL neurons was measured according to the VL multi-unit activity test method described in Experimental Example <3-1>.

For single-unit analysis, spikes were extracted using Spike Extractor software (Neuralynx), then clustered semi-automatically using the AutoKlustaKwik function in Spike-Sort 3D software (Neuralynx), followed by manual adjustment of the clusters. Only high-quality single units were used for data analysis. This protocol was also used in the other in vivo recording experiments. Low-threshold spike (LTS) bursts were defined using the criteria of Kraus et al. (2010), as follows: 1) a pre-silent period >100 ms, 2) interspike intervals <4 ms following the first two spikes, and 3)<4-ms interspike intervals between subsequent spikes. All other spikes were considered tonic spikes. After clustering single units, all spikes in each unit were sorted into tonic spikes or LTS bursts.

WT neurons evoked a surge of rebound firing within 200 ms of the post-inhibitory period that exceeded the firing rate measured prior to inhibition in multi-units (FIGS. 8(A) and 8(C)). In contrast, $Ca_V3.1$-KO neurons lacked this early-onset rebound firing and slowly regained baseline activity more than 200 ms after photostimulation ($p<0.05$, FIGS. 8(B) and 8(C)).

It was initially considered that possibility that the temporal pattern of spiking or excitability of individual VL neurons could explain the motor response evoked by activation of BG inputs.

One candidate mechanism is low-threshold burst firing, which consist of multiple action potentials at 200-400 Hz that serve as a strong motor signal. $Ca_V3.1$-KO VL neurons lack low-threshold burst spikes (not shown) and these mice do not show photostimulation-induced motor abnormalities (FIGS. 6(B) and 7). However, single-unit recordings revealed that low-threshold burst spikes were rare during the rebound firing induced by various photostimulation conditions in WT mice (not shown). In addition, in WT mice most motor responses were associated with rebound firing that lacked low-threshold burst spikes (not shown). This indicates that low-threshold burst spikes are not involved in the generation of motor signals during GPm-VL photo stimulation.

Figure 10:
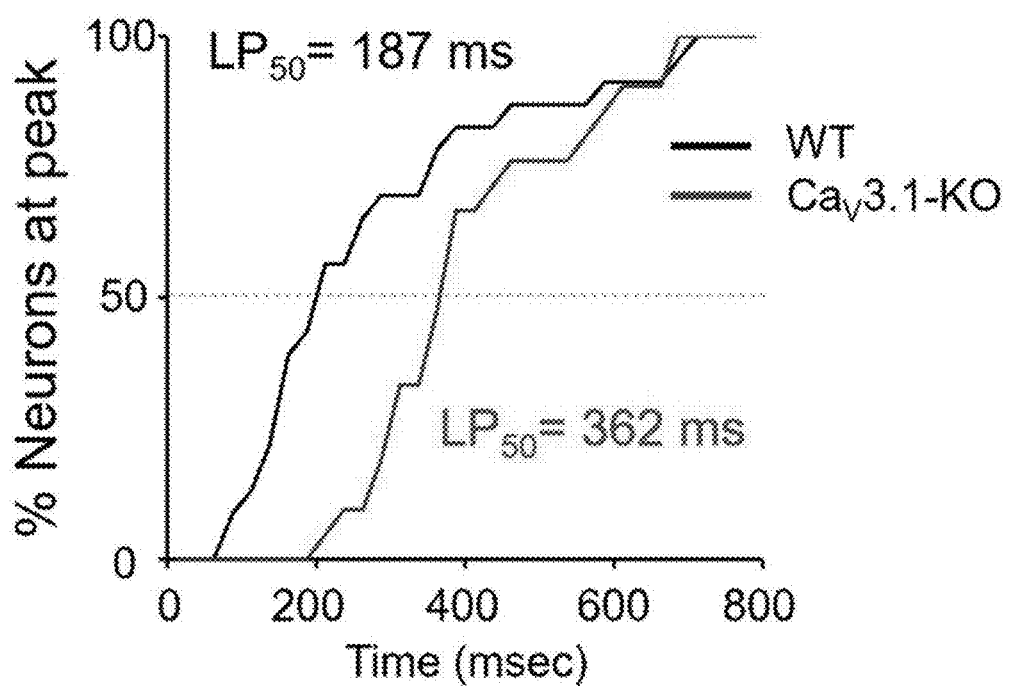
FIG. 10 illustrates the comparison of cumulative response probability (% total neurons recorded) based on latency to peak rebound firing rate for WT and KO mice (LP50 is the time at which 50% neurons exhibit peak rebound firing).

Next, the possibility that the firing rate of WT neuron is higher than KO neuron in the post-inhibitory period was tested. These data showed no significant differences in the peak firing rate (FIG. 8(D), (E), (F) and FIG. 9) or in the average firing rates of individual VL neurons between the two genotypes in the post-inhibitory period (not shown). Instead, as individual WT neurons reached a peak firing rate faster than KO neurons (LP50 for WT=187 ms; LP50 for KO=362 ms), a greater portion of neurons show peak firing within 200 ms of the post-inhibitory period (78% for WT vs. 14% for KO) (FIG. 10). These results suggest that the early-onset surge of rebound excitability, which might be critical for motor response induced by GPm-VL photostimulation, seems to depend on the number VL neurons with rebound firing rather than low-threshold burst spikes or averaged firing rate of individual neurons.

Experimental Example 5: T-Type $Ca^{2+}$ Channels Facilitate Rapid Repolarization of Membrane Potentials to Generate Early-Onset Firing To obtain detailed mechanistic information on how individual VL neurons produce early-onset rebound firing independently from low-threshold burst spikes, whole-cell patch-clamp recordings in VL slices from WT and $Ca_V3.1$-KO mice were performed to obtain high-resolution measurements of electrical activity in single neurons (FIG. 11).

<5-1> Whole-Cell Patch-Clamp Recording to Measure Neuronal Responses to Photo Stimuli Brain slices were prepared from WT and $Ca_V3.1$-KO mice 2 weeks to 7 months after the injection of AAV into the medial globus pallidus (GPm) region. In brief, isolated brains in high-sucrose artificial cerebrospinal fluid (sACSF; in mM: 87 sodium chloride, 75 sucrose, 25 $NaHCO_3$, 2.5 KCl, 0.5 $CaCl_2$, 7 $MgCl_2$, 1.25 $NaH_2PO_4$ and 25 d(+)-glucose), maintained at pH 7.4 by gassing with 95% $O_2$/5% $CO_2$, were sliced into 350-400-mm-thick coronal sections using a Vibratome (VT-1200; Leica, Germany). Slices were transferred to an incubation chamber filled with oxygenated ACSF consisting of (in mM) 125 NaCl, 2.5 KCl, 1.25 $NaH_2PO_4$, 25 $NaHCO_3$, 25 d (+)-glucose, 2 $CaCl_2$, 2 $MgCl_2$, 3 sodium pyruvate, and 1 ascorbic acid. Slices were incubated at 36° C. for 30 min and were maintained at room temperature for at least 30 min prior to use.

Whole-cell patch-clamp recordings were performed at 32° C. under an upright microscope (FV1000MPE, Olympus, Japan) in a recording chamber perfused with 95% $O_2$/5% $CO_2$-aerated ACSF as the extracellular solution. VL thalamus neurons were identified using infrared differential interference contrast (IR-DIC) optics in combination with a digital video camera (MCE-B013-U; Mightex, Canada). Whole-cell patch-clamp recordings were obtained from these neurons using glass pipettes (5-12 MΩ) filled with an internal solution consisting of (in mM) 130 K-gluconate, 2 NaCl, 4 $MgCl_2$, 20 HEPES, 4 $Na_2ATP$, 0.4 $Na_3GTP$, 0.5 EGTA, and 10 $Na_2$ phosphocreatine. The osmolarity of the solution was 290-295 mOsm, and the pH was adjusted to 7.25 using 1 M KOH. Unless otherwise indicated, all current measurements were made using a holding potential of −60 mV.

Electrical responses were acquired with a patch-clamp amplifier (Multiclamp 700B; Molecular Devices, USA) and pClamp software (Molecular Devices), digitized at 20 kHz using an A-D converter (Digidata 1440A; Molecular Devices), and analyzed using Clampfit (Molecular Devices). In parallel with the patch-clamp recordings, photostimuli were applied through a 25× (1.05 NA) water-immersion objective lens; the entire width of the microscope field (500 μm diameter) was illuminated. A mercury arc lamp (USH-1030L; Olympus), used to provide light to activate ChR2, was filtered using a band-pass filter (465-495 nm). Light pulses (5 $mW/mm^2$, 10-ms duration) were applied at 20 Hz for 10 s, controlled by an electronic shutter (Uniblitz VS25; Vincent, USA).

First, the properties of GPm-to-VL synaptic transmission were investigated. Photostimulation of GPm input induced inhibitory postsynaptic potentials (IPSP) in VL neurons (FIG. 11(A)). No significant differences between WT and $Ca_V3.1$-KO VL neurons were observed in terms of mean IPSP amplitude (FIG. 11(C)) or the fraction of VL neurons exhibiting IPSPs in response to photostimulation (FIG. 11(B)). These results indicate that GPm-VL inhibitory synaptic transmission is not altered in $Ca_V3.1$-KO mice.

<5-2> Whole-Cell Patch-Clamp Recording to Observe Rebound Firing in Thalamic Neurons Next, the intrinsic firing properties of VL neurons from WT and $Ca_V3.1$-KO mice were examined.

Adult male mice (7-19 weeks old) were anesthetized by i.p. injection of avertin, and sacrificed. The isolated brains were immersed in ice-cold artificial cerebrospinal fluid (ACSF; in mM: 125 NaCl, 2.5 KCl, 1.25 $NaH_2PO_4$, 25 $NaHCO_3$, 25 dextrose, 2 $CaCl_2$, 2 $MgCl_2$, 3 Na-pyruvate, 1 ascorbic acid, maintained at pH 7.4 by gassing with 95% $O_2$/5% $CO_2$) and were sliced into 250 μm thick coronal sections using a Vibratome. The slices were transferred to an incubation chamber filled with NMDG recovery solution (in mM: 92 NMDG, 92 HCl, 30 $NaHCO_3$, 2.5 KCl, 0.5 $CaCl_2$, 10 $MgSO_4$, 1.2 $NaH_2PO_4$, 20 HEPES, 5 Na-ascorbate, 3 Na-pyruvate, 2 thiourea, 25 dextrose, maintained at pH 7.4 by gassing with 95% $O_2$/5% $CO_2$) for 15 min at 36° C. Then the slices were maintained in oxygenated ACSF at room temperature for at least 1 hr prior to use.

VL thalamus neurons were recorded in oxygenated ACSF at 28-30° C. and visualized under an upright microscope (BX-51WI; Olympus, Japan). Whole-cell patch clamp recordings were performed using glass pipettes (3-4 MΩ) filled with internal solution (in mM: 130 K-gluconate, 2 NaCl, 4 $MgCl_2$, 20 HEPES, 4 $Na_2ATP$, 0.4 $Na_3GTP$, 0.5 EGTA, pH 7.25, 290-295 mOsm). VL thalamus neurons were ruptured at −70 mv. $I_T$ was identified in voltage-clamp mode using −30 mV hyperpolarization steps (200 ms) from a holding potential of −70 mV, then 5 mV depolarization steps (500 ms) from the holding potential. Spike latency and jitter after hyperpolarization were tested in current-clamp mode. After establishing the smallest holding current (maximum, 600 pA) at which the cell spontaneously and stably fired (1-8 Hz), 100 ms hyperpolarization currents, which varied from cell to cell (−215 to −400 pA) were applied, until a single rebound spike appeared after hyperpolarization.

T-type calcium channels were blocked by applying 500 μM $NiCl_2$ (Sigma) in ACSF for at least 10 min. After confirmed the effect of $NiCl_2$ application by recording $I_T$, holding currents at which the cell spontaneously and stably fired (maximum, 550 pA) were identified as described above. From these holding currents, we applied the same amount of 100 ms hyperpolarizing current as was applied prior to $NiCl_2$ treatment.

To confirm the effect of T-type calcium channel on rebound firing, the experiment with $Ca_V3.1$ KO mice was performed. After establishing the smallest holding current at which the cell spontaneously and stably fired (1-8 Hz), we applied 100 ms, −300 pA hyperpolarization currents were applied to VL thalamus neuron of $Ca_V3.1$ KO mice (Ra; 15.64±1.57 Mohm, holding; −52.04±11.19 pA) and wild-type mice (Ra; 14.25±3.23 Mohm, holding; −74.78±21.96 pA).

Figures 13A, 13B, 13C, 13D:
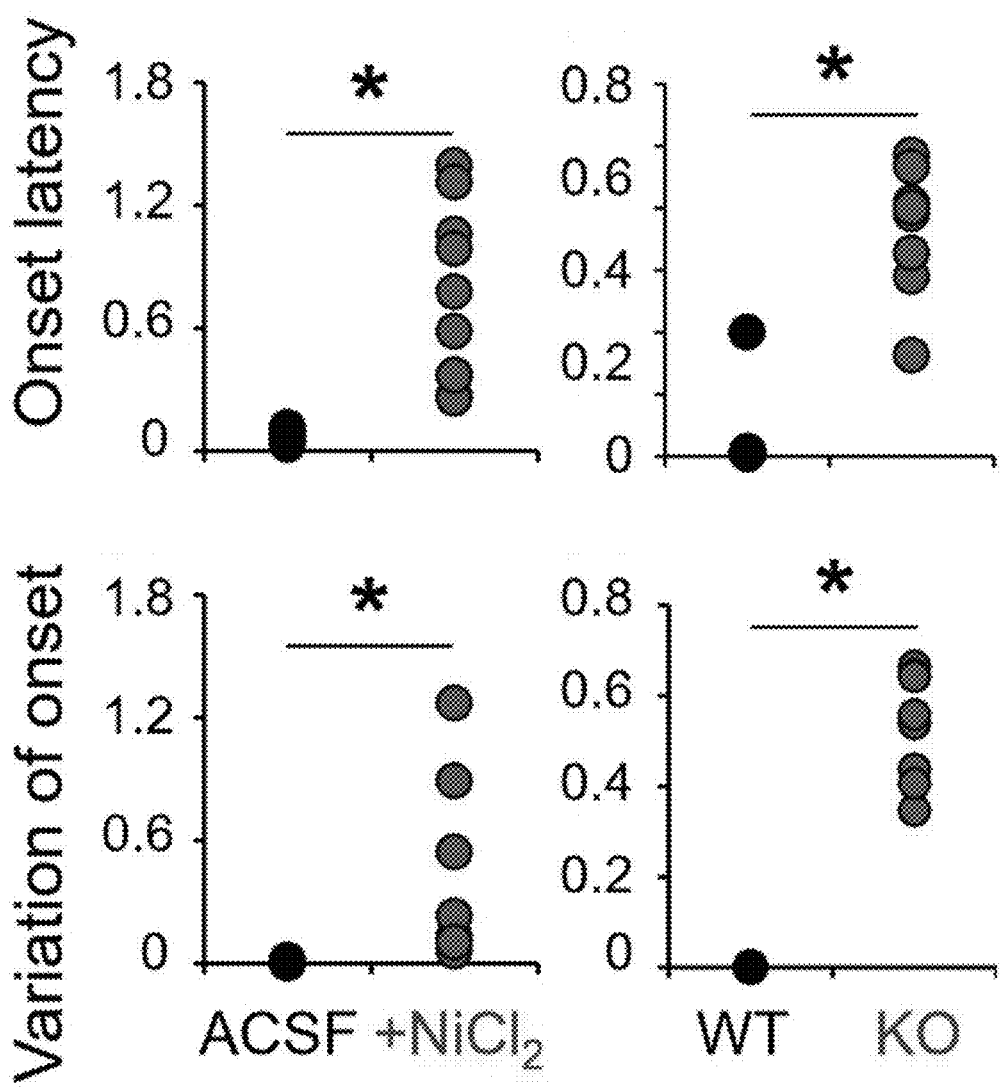
FIG. 13(A) and FIG. 13(B) illustrate the latency to first spike.
FIG. 13(C) and FIG. 13(D) illustrate the onset variation of the first spike before and after $Ni^{2+}$ treatment and between WT and CaV3.1-KO neurons in brain slices.

To mimic GPm-mediated inhibition in vivo, a hyperpolarizing current pulse (100 ms duration) was injected into VL neurons at a resting membrane potential of approximately −55 to −60 mV (FIGS. 12(A) and (B)). In every trial, WT neurons reproducibly exhibited single spikes soon after (~70 ms) the end of hyperpolarization. The timing of these early-onset spikes was replicated in many individual neurons, even in recordings obtained from different thalamic slices (FIGS. 12(C) and (D)). Blocking T-type $Ca^{2+}$ channels with nickel ($Ni^{2+}$, not shown) did not significantly alter neuronal intrinsic properties or firing rate (not shown). However, $Ni^{2+}$ treatment did produce a delay in early-onset spikes (FIG. 13(A)), which became much more irregular (FIG. 13(C)). As a result, rebound spikes occurred within a narrow time window (<200 ms) after application of the hyperpolarizing inhibitory stimulus in WT neurons but were delayed and dispersed in $Ni^{2+}$-treated neurons (FIG. 14). $Ni^{2+}$ treatment recapitulated the differences in post-inhibitory firing activity between WT and $Ca_V3.1$-KO neurons observed in vivo (compare to FIG. 10). Additionally, similar delays in the timing of early-onset spikes were observed in KO neurons (FIGS. 13(B) and (D)).

The delay in onset of post-inhibitory spikes caused by $Ni^{2+}$ (FIGS. 12, 13 and 14) may arise from delayed recovery of membrane potential after inhibition. This recovery rate determines the timing of action potential firing and is dependent on T-type $Ca^{2+}$ channel activity, because it was slowed by $Ni^{2+}$ (FIG. 15). Thus, in VL neurons rapid recovery from inhibition depends on $Ca^{2+}$ influx through the $Ca_V3.1$ channel. Furthermore, this recovery facilitates induction of rebound firing from many VL neurons within a narrow time window, thus yielding a higher excitatory output from the thalamus.

Experimental Example 6: Early-Onset Surge of Rebound Firing Mediates Motor Dysfunction <6-1> Correlation of Rebound Firing and Motor Abnormalities in CorWT and CaV3.1-KO Mice To define the causal relationship between rebound firing and motor abnormalities, first, the analyzed event-related potentials (ERP) was analyzed. Neural and muscular responses of WT and $Ca_V3.1$-KO mice were measured according to the EMG Recordings and VL single-unit activity method described in Experimental Example <3-1>. After the measurement, rebound firing analysis was performed as follows.

The rebound firing was identified from total multi-unit activities extracted from the spikes in each tetrode using threshold-based Spike Extractor software (Neuralynx). The onset time for rebound firing was identified as the time when the firing rate was increased over the mean firing rate, after the inhibitory period (over 50-ms) which shows lower firing rate than the mean. Because the reliable mean firing rate could not be computed within short duration, alternative method was utilized in the recording dataset shorter than 30 s. The 50-ms window was shifted every 10 ms and the firing rate was computed in each window. In cases where the firing rate steadily increased in three consecutive windows, the starting point of the second window was defined as the point at which firing rate increased. Since the firing rates in the first window were lower than basal activity, this method successfully identify the post-inhibitory activities.

All neural and muscular responses to each photostimulus (5, 25 or 50 ms pulse) were averaged, thereby filtering out random and uncorrelated signals (FIG. 16).

In response to brief photostimuli (<5 ms), WT mice exhibited a robust reduction in the firing rate of VL neurons but failed to show rebound firing or muscular responses (FIG. 16(A)). In contrast, flashes 25 ms or longer efficiently induced muscular responses (blue arrows in FIG. 16) accompanied by VL neuron inhibition and a greater amount of rebound firing that peaked approximately 170 ms after application of the photostimulus (red arrowheads in FIG. 16).

In $Ca_V3.1$ KO mice, photostimulation of GPm-VL synapses reduced the firing rate during the stimulus but did not induce significant rebound firing or muscular responses (asterisks in FIG. 16(B)).

Additionally, behavioral responses during photostimulation of GPm-VL synapses between WT and $Ca_V3.1$ KO mice were compared. Locomotor activity test was performed according to the method described in Experimental Example 1, and tremor test was performed according to the procedure described below. Each trial lasted for 30 min, and all trials were video-recorded. The test was performed between 12:00 PM and 6:00 PM. The intensity of tremor was scored by two independent investigators blinded to group-identifying information. Tremor intensity was rated on a scale of 0 to 4, as described by Lars M. Ittner et al. (Ittner et al., 2008), where 0 indicates no tremor, 1 intermittent slight tremor, 2 intermittent tremor, 3 strong tremor with rare quiescent periods, and 4 continuous tremor.

While WT mice showed decreased locomotor activity and tremor-like behaviors, as illustrated in FIGS. 1 to 5, $Ca_V3.1$-KO mice were resistant to the generation of multiple motor abnormalities (FIG. 17). These data strongly suggest that early-onset rebound firing within 200 ms after inhibition, mediated by $Ca_v3.1$, functions as the thalamic motor signal.

Figure 18:
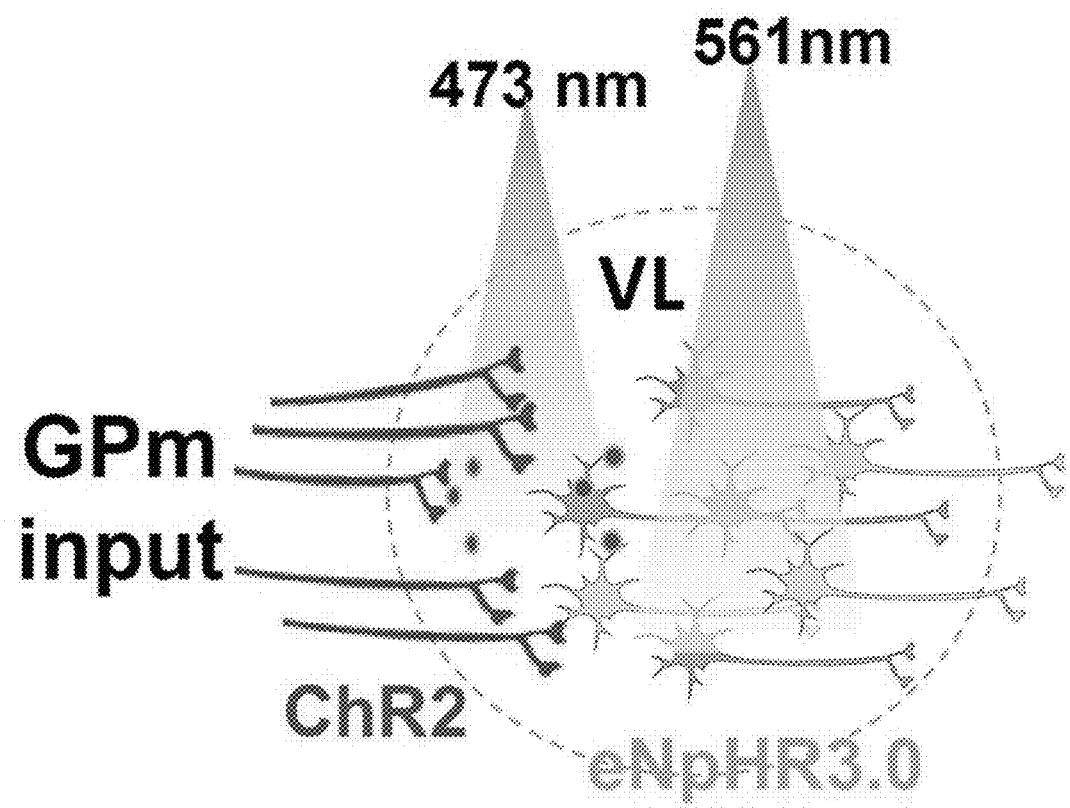
FIG. 18 illustrates the experimental scheme for photoactivation of GPm-VL synapses and photoinhibition of VL somata.

<6-2> Relationship Between Rebound Firing and Motor Abnormalities of Mice Expressing Halorhodopsin in VL Neurons and hChR2 in GPm To further test this suggestion, an optogenetic experiment in which rebound firing was inhibited during specific time windows was designed (FIG. 18). For this purpose, mice expressing halorhodopsin (eNpHR3.0) were constructed in Experimental Example 3. HChR2 was expressed in GPm to allow photostimulation of GPm inhibitory inputs to the VL, while halorhodopsin could photoinhibit VL neurons.

With this arrangement, 473 nm light (blue rectangles in FIG. 20) was applied to activate GPm-VL inputs and 561 nm light (green rectangles in FIG. 20) was used to inhibit postsynaptic activity during either the early or late post-inhibitory period (FIG. 20). FIG. 20 illustrates the representative EMG responses measured according to the method of EMG Recordings described in Experimental Example <3-1>. While photoactivation of GPm-VL inputs robustly induced muscular contractions (FIG. 20(A)), this motor response was abolished by postsynaptic photoinhibition during the early (<200 ms) post-inhibitory period (FIG. 20(B) and FIG. 21).

Figure 21:
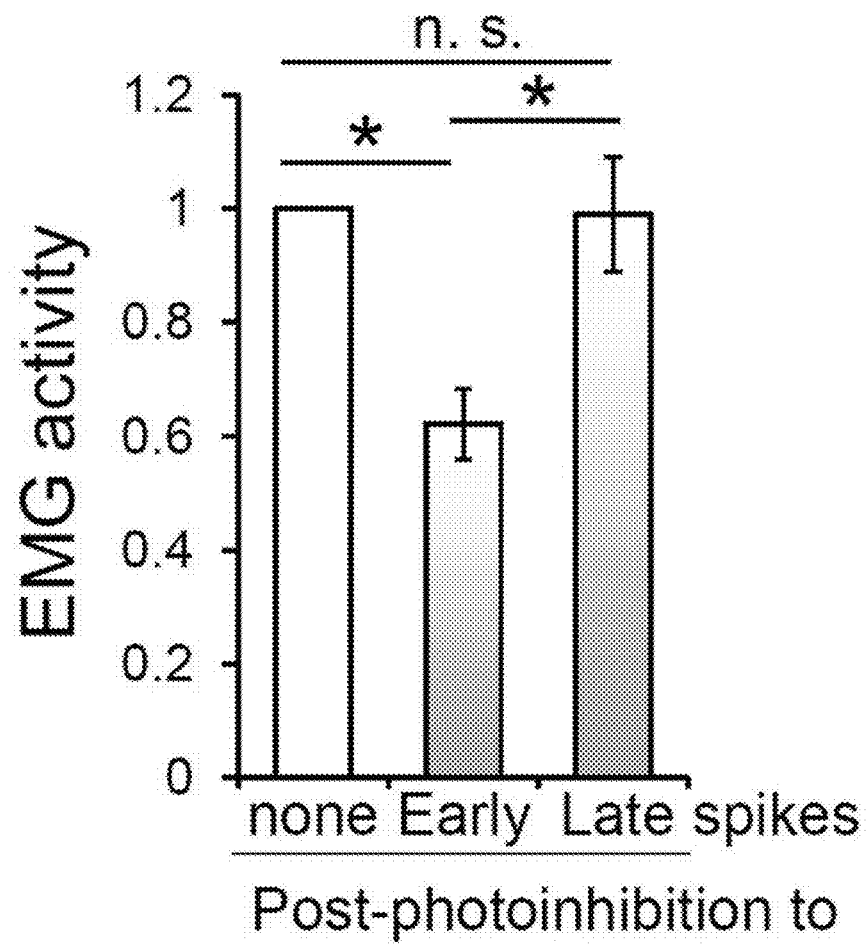
FIG. 21 illustrates the comparison of muscle activation in photoactivation of GPm-VL synapses with no photoinhibition of VL somata (None), photoinhibition of VL somata within 200 ms GPm-VL pathway photoactivation (Early) and photoinhibition of VL somata during 250-500 ms after GPm-VL pathway photoactivation (Late).

In contrast, photoinhibition >200 ms after activation of GPm input had little effect, allowing robust motor responses similar to controls (FIG. 20(C) and FIG. 21). These results suggest that the motor signal induced by the GPm input depends on very short-term integration of firing, rather than long-term integration or the average firing rate. Thus, the number of neurons that evoke rebound firing with similar timing within the first 200 ms post-inhibition controls the amount of excitatory output from the VL.

It was further investigated whether rebound firing mediates the hypokinesia produced by activating GPm inputs to VL. As in Experimental Example <6-1>, locomotor activity test and tremor test were also performed with mice expressing hChR2 in GPm and halorhodopsin in VL neurons.

Figure 22A:
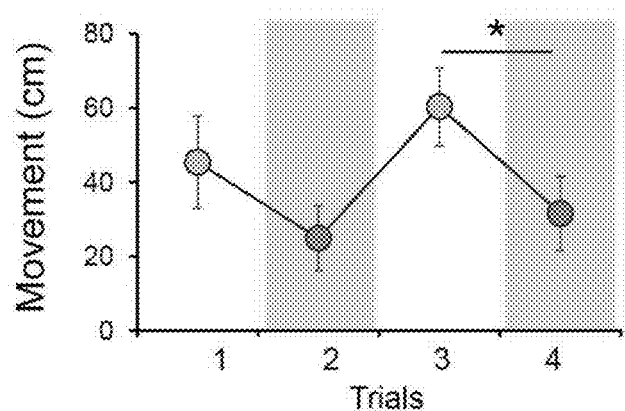
FIG. 22(A) illustrates the quantification of the effect of GPm-VL photostimulation with blue light on locomotion.
Figure 22B:
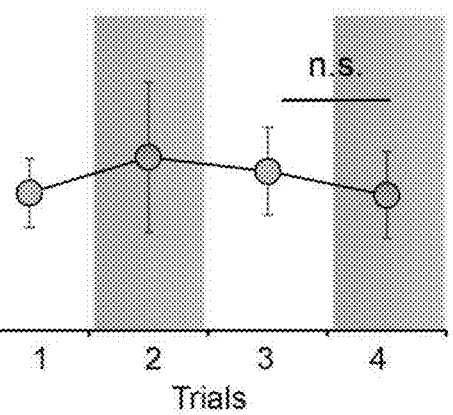
FIG. 22(B) illustrates the quantification of the dual stimulation effect with blue light (for activating hChR2 in axon terminals from GPm to VL thalamus) and green light (for activating eNpHR3.0 in VL somata) on locomotion.

Rhythmic photostimulation of the inputs via blue light (473 nm) induced a significant reduction in locomotion (FIG. 22(A)) similar to the results shown in FIG. 2. However, pairing photostimulation of GPm inhibitory inputs with photoinhibition of VL neurons via green light (561 nm) efficiently restored locomotion activity (FIG. 22(B)). These results strongly support the conclusion that multiple motor dysfunctions arise from rebound firing of VL neurons.

Experimental Example 7: Dietary Supplementation Rescues Motor Abnormalities Resulting from Dopamine Deficiency in SPR-KO Mice These results thus far indicate that rebound firing in VL thalamus is sufficient to cause multiple motor abnormalities. Next, it was investigated whether this thalamic mechanism is altered during PD-like motor abnormalities. For this purpose, the GPm-VL circuit was examined in a mouse model of dopamine deficiency, specifically, the sepiapterin reductase knockout (SPR-KO) mice constructed in Example 4. SPR catalyzes the synthesis of tetrahydrobiopterin (BH4), a cofactor for tyrosine hydroxylase, the rate-limiting enzyme in the synthesis of dopamine. The SPR gene is linked to a locus for familial Parkinson's disease (PARK3) of unknown genetic identity. Mutations in SPR are associated with L-DOPA-responsive dystonia, which is characterized by PD-like motor dysfunction, including akinesia, rigidity, and tremor. Similarly, SPR-KO mice show motor abnormalities. However, their short lifespan (2-3 weeks) and severe health problems have limited analysis of their behavior and underlying circuitry.

To improve the survivability of SPR-KO mice, their daily diet was supplemented with tetrahydrobiopterin (BH4), which extended their life-span to old age. Older-aged KO mice had fewer dopaminergic axon fibers and lower striatal dopamine levels compared with WT mice (not shown). After cessation of BH4 feeding, mice rapidly (within 24 h) developed severe motor impairment, including akinesia, gait disturbance, tremor, and rigidity (not shown). Except for rigidity, all these motor problems were ameliorated by the administration of L-DOPA, a standard treatment for PD (not shown). These results indicate the utility of SPR-KO mice with BH4 dietary supplementation as a reliable and reversible model of dopamine deficiency for analysis of PD-related neural circuitry.

Experimental Example 8: SPR-KO Mice not Administered the BH4 Diet Show Enhanced Rebound Firing <8-1> In Vivo Spike Recordings in SPR-KO and WT Mice In vivo spike recording was performed to measure rebound firing in SPR-KO mice. For multi-unit recording, SPR-KO and WT mice were anesthetized with urethane (1.35 g/kg, i.p.) and placed in a stereotaxic apparatus (David Kopf Instruments). Body temperature was maintained at 37° C. using a temperature-control device (Homothermic Blanket System; Harvard Apparatus, USA). After making a single incision in the scalp, the skull was exposed, a hole was made above the VL region, and a quartz-coated tetrode (5-2 MΩ; Thomas Recording, Germany) was implanted into the VL thalamus (−0.825 mm AP, −1.0 ML, −3.3-3.5 DV). Signals were amplified 95-fold using an AC amplifier. Acquired signals were filtered with a 300-5 kHz band-pass filter for measurement of multi-unit activity or a 0.50-50 Hz band-pass filter for the measurement of LFP, and digitized at a sampling rate of 10 kHz (DT3010; Neuralynx, USA). The location of the tetrode in the brain was confirmed by briefly dipping the tip of the tetrode in fluorescent dye solution (DiI, 50 mg/ml; Sigma) before implantation. The position of the electrode in brain slices was visualized by fluorescence microscopy (IX51; Olympus) using a rhodamine filter.

The rebound firing was identified from total multi-unit activities extracted from the spikes in each tetrode using threshold-based Spike Extractor software (Neuralynx). The onset time for rebound firing was identified as the time when the firing rate was increased over the mean firing rate, after the inhibitory period (over 50-ms) which shows lower firing rate than the mean. Because the reliable mean firing rate could not be computed within short duration, alternative method was utilized in the recording dataset shorter than 30 s. The 50-ms window was shifted every 10 ms and the firing rate was computed in each window. In cases where the firing rate steadily increased in three consecutive windows, the starting point of the second window was defined as the point at which firing rate increased. Since the firing rates in the first window were lower than basal activity, this method successfully identify the post-inhibitory activities.

Figure 24:
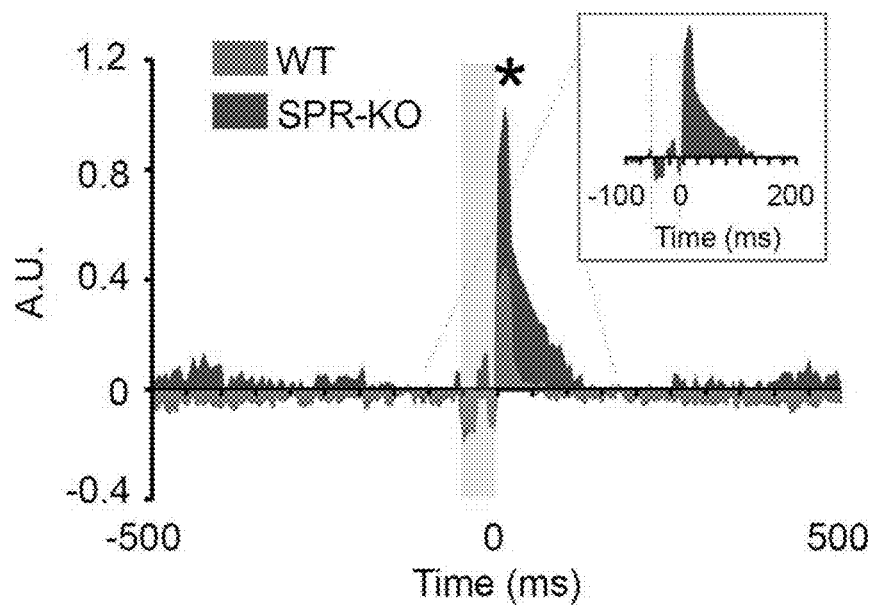
FIG. 24 illustrates the quantification of spikes following spontaneous inhibitory events in VL neurons of WT and SPR-KO mice.

To measure spontaneous rebound activity, spontaneous inhibition as a decrease in neuronal firing rate to a level 50% lower than the baseline frequency was detected. After detecting such epochs of inhibition, multi-unit spikes in time for the 50 ms preceding (pink shading in FIG. 23) and following the inhibitory event (FIGS. 23 and 24) were aligned. Consistent with the response of VL neurons to photostimulation of GPm inputs (FIGS. 6(A) and 8(A)), inhibitory events in WT mice were followed by rebound firing (red arrowheads in FIG. 23). Rebound firing was dramatically greater in SPR-KO mice (red arrowheads in FIG. 23(B)), particularly within the first 200 ms after inhibition (FIG. 24). The intrinsic properties of VL neurons in SPR-KO mice were not significantly different from those of WT neurons, as measured by their ability to induce tonic and low-threshold burst spikes in brain slices (not shown). Instead, increased rebound firing appears to depend on greater inhibitory drive to the VL. Thus, a dopamine-deficiency induced inhibition appears to evoke rebound firing in a PD-like mouse model.
<8-2> In Vivo Spike Recordings in SPR-KO Mice Expressing Halorhodopsin To address the role of GPm-VL inputs in the spontaneous rebound firing observed in SPR-KO mice, as described in Example 5, GPm was infected with an adeno-associated virus (AAV) harboring eNpHR3.0 under the control of the EF1α promoter. Illumination with green light (532 nm) was used to photoinhibit GPm inputs, and multi-unit recordings were used to determine the effects of photoinhibition (FIG. 25).

For the optogenetic inhibition of GPm-VL synapses in SPR-KO mice, the recording experiment was performed after injecting the virus to express eNpHR3.0. Such photoinhibition of GPm inputs to VL substantially reduced rebound firing in KO mice (FIG. 26(A)).

To examine the effect of pharmacological inhibition of T-type calcium channel, ethosuximide (150 mg/kg, i.p.) was treated during the recording experiment in SPR-KO mice. Treatment with ethosuximide (ETX; i.p. 150 mg/kg), a blocker of T-type $Ca^{2+}$ channels, also reduced spontaneous rebound firing of VL neurons in SPR-KO mice (FIGS. 26(B) and (C)), suggesting that in a dopamine-deficient state GPm inhibitory input mediates rebound firing in the VL via T-type calcium channels.

Experimental Example 9: GPm-VL Inhibitory Inputs Mediate Motor Defects in SPR-KO Mice To assess the impact of GPm inputs on the motor deficits of SPR-KO mice, first, a loss-of-function optogenetics experiment was performed by photoinhibiting the GPm-VL pathway.

Locomotor activity test, akinesia, rigidity test and tremor test were performed according to the methods described in Experimental Examples 1, <2-2> and <6-1>.

Figure 28:
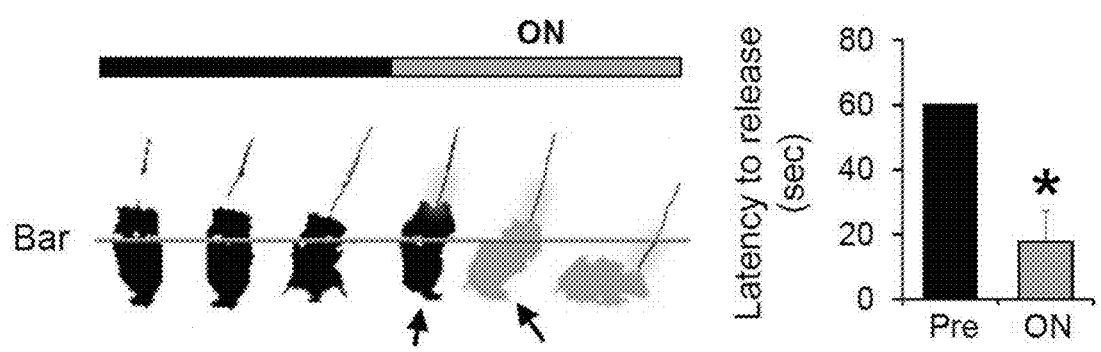
FIG. 28 illustrates the photoinhibition of GPm-VL synapses reduces rigidity of SPR-KO mice measured in a horizontal bar test (The green rectangle: the period of photoinhibition (20 s, continuous 532 nm light)).

Photoinhibition of GPm inputs to the VL rescued the locomotor defect of SPR-KO mice, allowing free movement (FIG. 27(A)). Additionally, photoinhibition decreased the locomotion latency of SPR-KO mice to the level of WT mice (FIG. 27(B)) (2.18±1.16 s vs. 2.19±0.71 s for WT mice) and reduced the time spent being immobile (FIG. 27(C)) (25%±16% vs. 29%±10% for WT). Photoinhibition of GPm-VL inputs also decreased the latency to release a horizontal bar by >35%, indicating efficient reversal of muscular rigidity (FIG. 28). The most significant change observed was a >50% reduction in tremor activity (FIG. 29(A)).

To examine the effect of pharmacological inhibition of T-type calcium channel, ethosuximide (150 mg/kg, i.p.) was treated during tremor tests. In addition, the same tests were performed on the mice treated with the shRNA constructed in Example 6.

The abnormal motor functions of SPR-KO mice were ameliorated by reducing rebound firing, either via administration of ETX (FIG. 29(B)) or VL-specific knockdown of the $Ca_V3.1$ gene with targeted shRNA (FIG. 29(C)). Taken together, these results indicate that GPm inputs mediate a powerful rebound firing of VL neurons, which underlies multiple forms of PD-like motor dysfunction in SPR-KO mice.

Experimental Example 10: Rebound Excitability of VL Neurons in Normal Conditions Having established that rebound firing plays an important role in motor dysfunction of dopamine-deficient SPR-KO mice, and that inhibition of rebound firing rescues the PD-like motor impairments of these mice, VL neuron activity in WT mice was recorded to determine whether rebound firing also occurs in physiological situations (FIG. 30).
<10-1> In Vivo Spike Recording During Natural Resting-Running Transitions Mice were anesthetized with avertin and placed in a stereotaxic device. Mice were prepared for recording on the running wheel by cementing a custom-designed head-plate with a window opening above the right VL thalamus to the skull with Super-Bond and dental cement. A small screw, serving as a ground electrode, was implanted in the skull above the cerebellum.

Mice were trained to voluntarily run on the wheel with their head fixed. The implanted head-plate was clamped to a holder device, which was modified from Royer et al. (2012). Training sessions were started more than 2 days after surgery to allow recovery. Mice were mildly water-deprived for 5-8 h before training. When a mouse ran more than the conditioned distance (about 15 cm, 6 blocks in the distance meter) within 5 s, it was rewarded with sucrose-in-water. Training was continued over 4 d (20 min/d) until each mouse had run more than 10 times during the training session.

For recording awake, behaving status (FIG. 6), mice were anesthetized with isoflurane (1.5% in oxygen), and their heads were fixed to a holder device. The skull above the right VL thalamus (1.0 mmAP, -1.0 ML) was drilled to make a hole, and the dura was removed to allow insertion of a silicon probe (16 channels separated by 25 NeuroNexus, USA). The probe was fixed to a micromanipulator and lowered into the brain. After reaching the VL thalamus, the hole was sealed with 1.5% liquid agar applied at near body temperature. After the mice had completely recovered from the anesthesia, a recording session was started and typically lasted for 60 min.

Mouse behavior and reward delivery were recorded as text in a computer file, and video was recorded for detailed behavioral analysis using the Cheetah acquisition system (Neuralynx). Neural signals were recorded with the Cheetah 16-channel acquisition system (Neuralynx) and band-pass filtered at 0.5-50 Hz for LFP and 3-5 kHz for single-unit activity.

A 20 min period when mice were active was selected for analysis. Behaviors were classified into five categories; Rest (Nogo), Go transition (Nogo to Go), Movement (Go), Stop transition (Go to Nogo), and other behaviors.

Rest and Movement were determined when the mice showed no movement (Rest) or actively ran (Movement). Other behaviors except runs, such as licking and grooming, were not included in the Movement category. Complete moving and resting states were classified by removing periods 3 s before and after active movement, and 1 s before and after subtle movement.

Go and Stop transitions corresponded to initiation (Go transition) and termination (Stop transition) of a run, respectively. Behavior was considered a Go transition only when mice showed no movement for 3 s before movement initiation, and actively ran for more than 3 s after movement initiation. Behavior was considered a Stop transition only when mice actively ran and slowed down for 3 s before movement termination, and did not move for 3 s after movement termination. The precise times of Go and Stop transitions were determined by analyzing video recordings (29.97 frames/s) with frame-scale, and synced with a single-unit recording system (TS clock in the Cheetah acquisition system).

Figure 31:
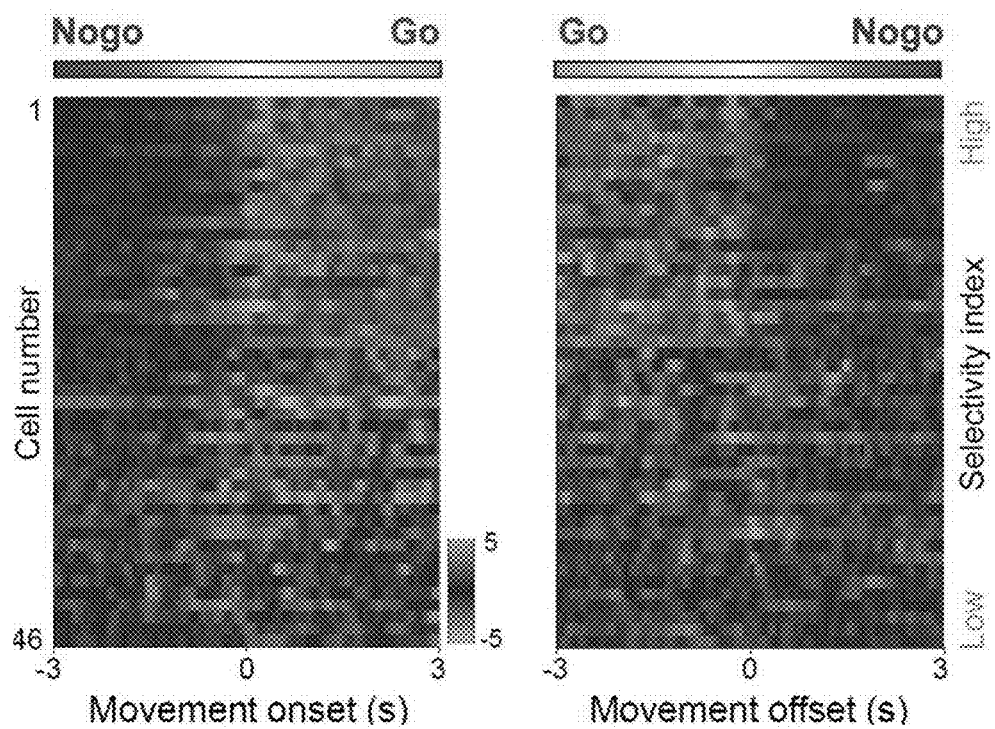
FIG. 31 illustrates the firing activities of VL neurons arranged in descending order of the selectivity index expressing the association of spiking with movement (selectivity index=(fmovement fresting)/(fmovement+fresting)) (Each horizontal row presents the activity of individual VL neurons 3 s before and after the transition. The neurons in upper rows showed higher movement-related neural activities).
Figure 32A:
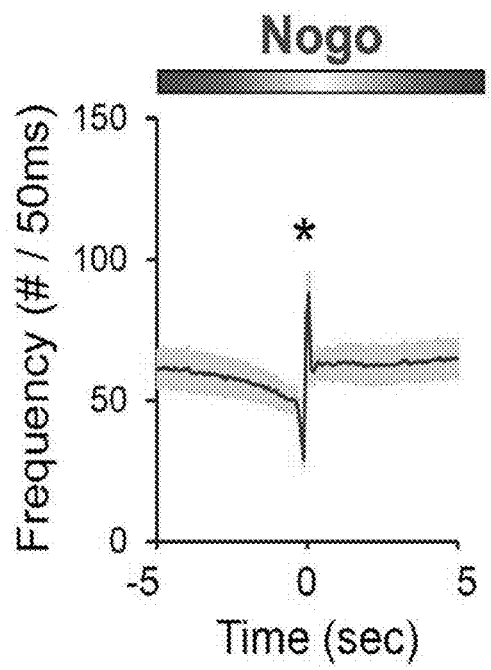
FIG. 32(A), FIG. 32(B), FIG. 32(C) and FIG. 32(D) illustrate the alignment of multi-unit spikes for 50 ms preceding and following an inhibitory event defined as a reduction in baseline firing frequency of >50% during one of the four possible behavioral states (FIG. 32(A) Nogo, FIG. 32(B) Nogo-Go, FIG. 32(C) Go, FIG. 32(D) Go-Nogo).
Figure 32B:
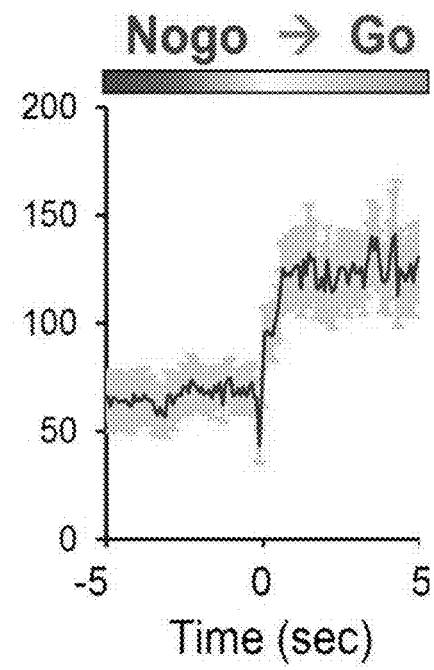
Figure 32C:
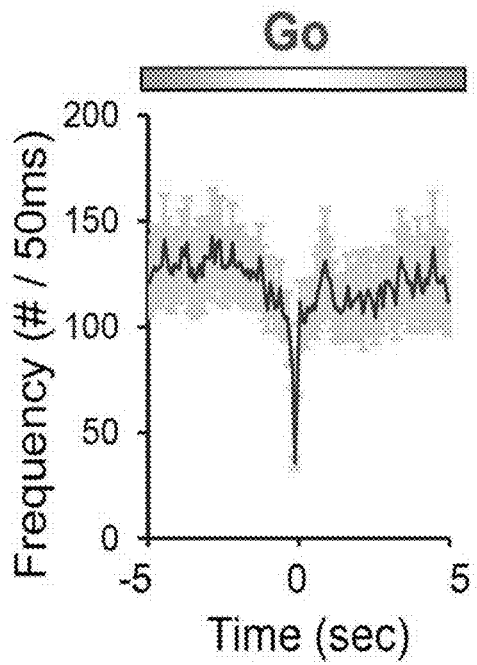
Figure 32D:
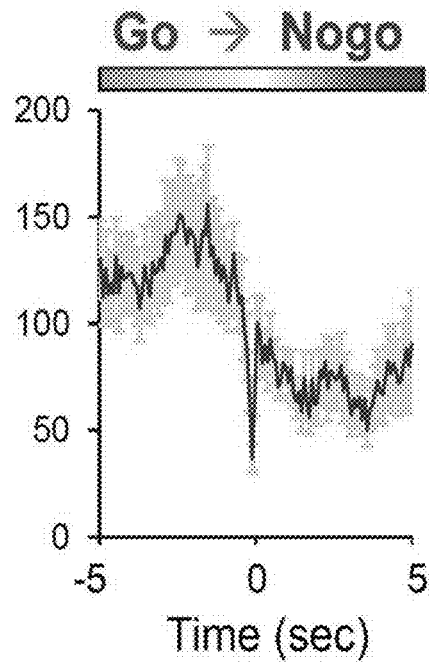

Initially, the movement-related activity of VL neurons in WT mice was compared during the natural transition between resting and running (FIG. 31). Selectivity index values were determined based on the firing rates associated with specific movement states (No-go vs. Go) and subsequently sorted in descending order. Nearly all thalamic neurons (94%) exhibited state-dependent changes in their activity. The majority of neurons displayed a higher firing rate during the Go than No-go state. This relationship was most apparent during transitions between the two states (FIG. 31) and is consistent with a rate-coding model, namely that a decrease in the average firing rate of VL neurons is associated with reduced locomotion.

Next, rebound firing during different behavioral states was examined by aligning the recordings of multi-unit spikes for 50 ms preceding and following each inhibitory event, which again was defined as a 50% or greater reduction in baseline firing frequency. Comparison of VL neuronal activity during four behavioral states (FIG. 32) revealed the strongest rebound firing during the No-go state (asterisk in FIG. 32), occurring approximately 1-5 times per second. The normal incidence of rebound firing was significantly lower than in the dopamine-deficient state (~40%, FIG. 24), indicating the involvement of a smaller number of neurons involved in rebound firing in these mice compared to WT mice. Given that rebound firing of thalamic neurons activates muscles (FIGS. 6 to 10 and FIGS. 16 to 22), the spontaneous rebound firing observed in WT mice may also stimulate the muscle activity required for maintaining their posture on a running wheel during the resting state. The PD-like symptoms observed in SPR-KO mice may arise from increased rebound firing of neurons and subsequent dysfunctional muscle movement (FIGS. 23 to 29). This hypothesis is consistent with the observation that PD symptoms are more severe during the resting state.

Decreased firing of VL neurons potentially involves a reduction in motor activity and additional induction of post-inhibitory excitation stabilizes this 'standstill' by inducing sufficient muscle tension. However, excessive rebound firing may trigger pathological conditions that interfere with voluntary motor control, such as akinesia, rigidity, and tremor.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

We claim:

1. A method for treating Parkinson's disease in a subject, comprising inhibiting rebound firing of ventrolateral thalamus (VL) neurons in the subject, comprising injecting a polynucleotide encoding a halorhodopsin protein, or a vector comprising the polynucleotide, into VL or globus pallidus (GPm) neurons of the subject and irradiating postsynaptic VL neurons of the subject with green light, thereby treating Parkinson's disease in the subject.

2. The method for treating Parkinson's disease according to claim 1, wherein the halorhodopsin protein comprises the amino acid sequence represented by SEQ ID NO: 1.

3. The method for treating Parkinson's disease according to claim 1, wherein the polynucleotide encoding the halorhodopsin protein comprises the nucleotide sequence represented by SEQ ID NO: 2.

4. The method for treating Parkinson's disease according to claim 1, wherein the vector is a DNA vector, a plasmid DNA vector, or a recombinant viral vector.

5. The method for treating Parkinson's disease according to claim 4, wherein the recombinant viral vector is a retrovirus, adenovirus, adeno-associated virus, or lentivirus vector.

6. A method for treating Parkinson's disease in a subject, comprising:
   injecting a recombinant adeno-associated virus (AAV) vector encoding a halorhodopsin protein into ventrolateral thalamus (VL) or globus pallidus (GPm) neurons of the subject; and
   irradiating the postsynaptic VL neurons of the subject with green light,
   thereby treating Parkinson's disease in the subject.

* * * * *

SEQUENCE LISTING

```
<160> NUMBER OF SEQ ID NOS: 8

<210> SEQ ID NO 1
<211> LENGTH: 291
<212> TYPE: PRT
<213> ORGANISM: Artificial Sequence
<220> FEATURE:
<223> OTHER INFORMATION: Synthetic polypeptide (Halorhodopsin)

<400> SEQUENCE: 1

Met Thr Glu Thr Leu Pro Pro Val Thr Glu Ser Ala Val Ala Leu Gln
1               5                   10                  15

Ala Glu Val Thr Gln Arg Glu Leu Phe Glu Phe Val Leu Asn Asp Pro
            20                  25                  30

Leu Leu Ala Ser Ser Leu Tyr Ile Asn Ile Ala Leu Ala Gly Leu Ser
        35                  40                  45

Ile Leu Leu Phe Val Phe Met Thr Arg Gly Leu Asp Asp Pro Arg Ala
    50                  55                  60

Lys Leu Ile Ala Val Ser Thr Ile Leu Val Pro Val Val Ser Ile Ala
65                  70                  75                  80

Ser Tyr Thr Gly Leu Ala Ser Gly Leu Thr Ile Ser Val Leu Glu Met
                85                  90                  95

Pro Ala Gly His Phe Ala Glu Gly Ser Ser Val Met Leu Gly Gly Glu
            100                 105                 110

Glu Val Asp Gly Val Val Thr Met Trp Gly Arg Tyr Leu Thr Trp Ala
        115                 120                 125

Leu Ser Thr Pro Met Ile Leu Leu Ala Leu Gly Leu Leu Ala Gly Ser
    130                 135                 140

Asn Ala Thr Lys Leu Phe Thr Ala Ile Thr Phe Asp Ile Ala Met Cys
145                 150                 155                 160
```

```
Val Thr Gly Leu Ala Ala Ala Leu Thr Thr Ser Ser His Leu Met Arg
            165                 170                 175

Trp Phe Trp Tyr Ala Ile Ser Cys Ala Cys Phe Ile Val Val Leu Tyr
            180                 185                 190

Ile Leu Leu Val Glu Trp Ala Gln Asp Ala Lys Ala Ala Gly Thr Ala
            195                 200                 205

Asp Ile Phe Ser Thr Leu Lys Leu Leu Thr Val Val Met Trp Leu Gly
            210                 215                 220

Tyr Pro Ile Val Trp Ala Leu Gly Val Glu Gly Val Ala Val Leu Pro
225                 230                 235                 240

Val Gly Tyr Thr Ser Trp Ala Tyr Ser Ala Leu Asp Ile Val Ala Lys
            245                 250                 255

Tyr Ile Phe Ala Phe Leu Leu Leu Asn Tyr Leu Thr Ser Asn Glu Gly
            260                 265                 270

Val Val Ser Gly Ser Ile Leu Asp Val Pro Ser Ala Ser Gly Ala Pro
            275                 280                 285

Ala Asp Asp
    290

<210> SEQ ID NO 2
<211> LENGTH: 7286
<212> TYPE: DNA
<213> ORGANISM: Artificial Sequence
<220> FEATURE:
<223> OTHER INFORMATION: Synthetic polynucleotide (Halorhodopsin)

<400> SEQUENCE: 2
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac tagggggttcc tgcggccgca cgcgtaagct ttgcaaagat ggataaagtt    180
ttaaacagag aggaatcttt gcagctaatg gaccttctag gtcttgaaag gagtgggaat    240
tggctccggt gcccgtcagt gggcagagcg cacatcgccc acagtccccg agaagttggg    300
gggaggggtc ggcaattgaa ccggtgccta gagaaggtgg cgcggggtaa actgggaaag    360
tgatgtcgtg tactggctcc gccttttttcc cgagggtggg ggagaaccgt atataagtgc    420
agtagtcgcc gtgaacgttc ttttttcgcaa cgggtttgcc gccagaacac aggtaagtgc    480
cgtgtgtggt tcccgcgggc ctggcctctt tacgggttat ggcccttgcg tgccttgaat    540
tacttccact ggctgcagta cgtgattctt gatcccgagc ttcgggttgg aagtgggtgg    600
gagagttcga ggccttgcgc ttaaggagcc ccttcgcctc gtgcttgagt tgaggcctgg    660
cctgggcgct ggggccgccg cgtgcgaatc tggtggcacc ttcgcgcctg tctcgctgct    720
ttcgataagt ctctagccat ttaaaatttt tgatgacctg ctgcgacgct tttttttctgg    780 caagatagtc ttgtaaatgc gggccaagat ctgcacactg gtatttcggt ttttggggcc    840
gcgggcggcg acgggcccg tgcgtcccag cgcacatgtt cggcgaggcg gggcctgcga     900
gcgcggccac cgagaatcgg acgggggtag tctcaagctg gccggcctgc tctggtgcct    960
ggcctcgcgc cgccgtgtat cgccccgccc tgggcggcaa ggctggcccg gtcggcacca   1020
gttgcgtgag cggaaagatg gccgcttccc ggccctgctg cagggagctc aaaatggagg   1080
acgcggcgct cggagagcg ggcgggtgag tcacccacac aaaggaaaag gcctttccg      1140 tcctcagccg tcgcttcatg tgactccacg gagtaccggg cgccgtccag gcacctcgat   1200
tagttctcga gcttttggag tacgtcgtct ttaggttggg gggagggggtt ttatgcgatg   1260
```

```
gagtttcccc acactgagtg ggtggagact gaagttaggc cagcttggca cttgatgtaa    1320
ttctccttgg aatttgccct tttgagttt ggatcttggt tcattctcaa gcctcagaca    1380
gtggttcaaa gttttttct tccatttcag gtgtcgtgag gtaccggatc ctctagagtc    1440
gactccggaa taacttcgta taggatactt tatacgaagt tatgcagaat ggtagctgga    1500
ttgtagctgc tattagcaat atgaaacctc ttaataactt cgtatagcat acattatacg    1560
aagttatggc gcgcctcatt acacctcgtt ctcgtagcag aacttgtaca gctcgtccat    1620
gccgagagtg atcccggcgg cggtcacgaa ctccagcagg accatgtgat cgcgcttctc    1680 gttgggtct ttgctcaggg cggactggta gctcaggtag tggttgtcgg gcagcagcac    1740
ggggccgtcg ccgatggggg tgttctgctg gtagtggtcg gcgagctgca cgctgccgtc    1800
ctcgatgttg tggcggatct tgaagttcac cttgatgccg ttcttctgct tgtcggccat    1860
gatatagacg ttgtggctgt tgtagttgta ctccagcttg tgccccagga tgttgccgtc    1920
ctccttgaag tcgatgccct tcagctcgat gcggttcacc agggtgtcgc cctcgaactt    1980
cacctcggcg cgggtcttgt agttgccgtc gtccttgaag aagatggtgc gctcctggac    2040
gtagccttcg ggcatggcgg acttgaagaa gtcgtgctgc ttcatgtggt cggggtagcg    2100
ggcgaagcac tgcaggccgt agccgaaggt ggtcacgagg gtgggccagg cacgggcag     2160 cttgccggtg gtgcagatga acttcagggt cagcttgccg taggtggcat cgccctcgcc    2220
ctcgccggac acgctgaact tgtggccgtt tacgtcgccg tccagctcga ccaggatggg    2280 caccacccg tgaacagct cctcgccctt gctcaccacg ttgatgtcga tctggtccag      2340
ggggatgtac tcgccctcgc tggtgatcct gctcttggcg gccgcatcat cagccggggt    2400
cccagaagca gatggaacat ccaaaatgct gccggacacg acagattcgt ttgacgtcag    2460
atagttcagg agcaagaatg cgaaaatgta ctttgccacg atatccagga aagaatatcc    2520
ccagctcgtc acccccaacgg gcaacaccgc gataccctcg actccaagag cccacacaat    2580 tggataccccc agccacatca ctactgtcaa cagcttcagg gtattgaaca tgtcagcggt    2640
tcccgcggct ttggcgtcct gtgcccactc caccagcagg atatacaaga ccaccgaaaa    2700
gcatgcacaa ctgatagcgt accagaacca tctcatgagg tgggaggagg tagtcagggc    2760
cgcggcaagg ccagtcacgc acatagcgat atcgaaagtg atagctgtga agagctttgt    2820
agcattgctt ccgccagga gacccagagc gaggagaatc atgggcgtgg aaagtgccca    2880
ggtgagatac cgtccccaca tggtgactac accatctacc tcttctcctc ccagcatcac    2940
tgagctgcct tctgcaaaat ggcccgctgg catttcaaga acggaaattg tcaggccgct    3000
cgccaatcca gtgtaggagg caatgctgac gacaggcaca aggatggttg acacagcaat    3060
aagttttgcc cgtggatcat cgagtcctcg ggtcataaaa acgaacagca gtatactcag    3120
tcctgcaagt gcgatgttga tatagagact gcttgcaagc aaagggtcgt tcagcacgaa    3180
ctcgaacaac tccctttggg taacctcggc ttgaagggcc acggcactct cggtcacggg    3240
aggcagggtc tctgtcatgg tggcgctagc ataacttcgt ataaagtatc ctatacgaag    3300
ttatttgcct taacccagaa attatcactg ttattcttta gaatggtgca aagaataact    3360
tcgtataatg tatgctatac gaagttatga attcgatatc aagcttatcg ataatcaacc    3420
tctggattac aaaatttgtg aaagattgac tggtattctt aactatgttg ctccttttac    3480
gctatgtgga tacgctgctt taatgccttt gtatcatgct attgcttccc gtatggcttt    3540
cattttctcc tccttgtata aatcctggtt gctgtctctt tatgaggagt tgtggcccgt    3600
```

```
tgtcaggcaa cgtggcgtgg tgtgcactgt gtttgctgac gcaaccccca ctggttgggg    3660
cattgccacc acctgtcagc tcctttccgg gactttcgct ttccccctcc ctattgccac    3720
ggcggaactc atcgccgcct gccttgcccg ctgctggaca ggggctcggc tgttgggcac    3780
tgacaattcc gtggtgttgt cggggaaatc atcgtccttt ccttggctgc tcgcctatgt    3840
tgccacctgg attctgcgcg ggacgtcctt ctgctacgtc ccttcggccc tcaatccagc    3900
ggaccttcct tcccgcggcc tgctgccggc tctgcggcct cttccgcgtc ttcgccttcg    3960
ccctcagacg agtcggatct ccctttgggc cgcctccccg catcgatacc gagcgctgct    4020
cgagagatct acgggtggca tccctgtgac ccctccccag tgcctctcct ggccctggaa    4080
gttgccactc cagtgcccac cagccttgtc ctaataaaat taagttgcat cattttgtct    4140
gactaggtgt ccttctataa tattatgggg tggagggggg tggtatggag caaggggcaa    4200
gttgggaaga caacctgtag ggcctgcggg gtctattggg aaccaagctg gagtgcagtg    4260
gcacaatctt ggctcactgc aatctccgcc tcctgggttc aagcgattct cctgcctcag    4320
cctcccgagt tgttgggatt ccaggcatgc atgaccaggc tcagctaatt tttgtttttt    4380
tggtagagac ggggtttcac catattggcc aggctggtct ccaactccta atctcaggtg    4440 atctaccac cttggcctcc caaattgctg ggattacagg cgtgaaccac tgctcccttc     4500
cctgtccttc tgattttgta ggtaaccacg tgcggaccga gcggccgcag gaaccctag    4560 tgatggagtt ggccactccc tctctgcgcg ctcgctcgct cactgaggcc gggcgaccaa    4620
aggtcgcccg acgccgggc tttgcccggg cggcctcagt gagcgagcga gcgcgcagct    4680
gcctgcaggg gcgcctgatg cggtattttc tccttacgca tctgtgcggt atttcacacc    4740
gcatacgtca aagcaaccat agtacgcgcc ctgtagcggc gcattaagcg cggcgggtgt    4800
ggtggttacg cgcagcgtga ccgctacact gccagcgccc tagcgcccg ctcctttcgc     4860 tttcttccct tcctttctcg ccacgttcgc cggctttccc cgtcaagctc taaatcgggg    4920
gctcccttta gggttccgat ttagtgcttt acggcacctc gaccccaaaa aacttgattt    4980
gggtgatggt tcacgtagtg ggccatcgcc ctgatagacg gttttcgcc ctttgacgtt     5040 ggagtccacg ttctttaata gtggactctt gttccaaact ggaacaacac tcaaccctat    5100
ctcgggctat tcttttgatt tataagggat tttgccgatt tcggcctatt ggttaaaaaa    5160
tgagctgatt taacaaaaat ttaacgcgaa ttttaacaaa atattaacgt ttacaatttt    5220
atggtgcact ctcagtacaa tctgctctga tgccgcatag ttaagccagc cccgacaccc    5280
gccaacaccc gctgacgcgc cctgacgggc ttgtctgctc ccggcatccg cttacagaca    5340
agctgtgacc gtctccggga gctgcatgtg tcagaggttt tcaccgtcat caccgaaacg    5400
cgcgagacga aagggcctcg tgatacgcct atttttatag gttaatgtca tgataataat    5460
ggtttcttag acgtcaggtg cacttttcg gggaaatgtg cgcggaaccc ctatttgttt     5520 attttctaa atacattcaa atatgtatcc gctcatgaga caataaccct gataaatgct    5580
tcaataatat tgaaaaagga agagtatgag tattcaacat ttccgtgtcg cccttattcc    5640
cttttttgcg gcattttgcc ttcctgtttt tgctcaccca gaaacgctgg tgaaagtaaa    5700
agatgctgaa gatcagttgg gtgcacgagt gggttacatc gaactggatc tcaacagcgg    5760
taagatcctt gagagttttc gccccgaaga acgttttcca atgatgagca cttttaaagt    5820
tctgctatgt ggcgcggtat tatcccgtat tgacgccggg caagagcaac tcggtcgccg    5880
catacactat tctcagaatg acttggttga gtactcacca gtcacagaaa agcatcttac    5940
ggatggcatg acagtaagag aattatgcag tgctgccata accatgagtg ataacactgc    6000
```

-continued

```
ggccaactta cttctgacaa cgatcggagg accgaaggag ctaaccgctt ttttgcacaa    6060
catgggggat catgtaactc gccttgatcg ttgggaaccg gagctgaatg aagccatacc    6120
aaacgacgag cgtgacacca cgatgcctgt agcaatggca acaacgttgc gcaaactatt    6180
aactggcgaa ctactactc tagcttcccg gcaacaatta atagactgga tggaggcgga     6240
taaagttgca ggaccacttc tgcgctcggc ccttccggct ggctggttta ttgctgataa    6300
atctggagcc ggtgagcgtg ggtctcgcgg tatcattgca gcactgggc cagatggtaa     6360
gccctcccgt atcgtagtta tctacacgac ggggagtcag gcaactatgg atgaacgaaa    6420
tagacagatc gctgagatag gtgcctcact gattaagcat tggtaactgt cagaccaagt    6480
ttactcatat atactttaga ttgatttaaa acttcatttt taatttaaaa ggatctaggt    6540
gaagatcctt tttgataatc tcatgaccaa atcccttaa cgtgagtttt cgttccactg     6600
agcgtcagac cccgtagaaa agatcaaagg atcttcttga gatccttttt ttctgcgcgt    6660
aatctgctgc ttgcaaacaa aaaaaccacc gctaccagcg gtggtttgtt tgccggatca    6720
agagctacca actctttttc cgaaggtaac tggcttcagc agagcgcaga taccaaatac    6780
tgtccttcta gtgtagccgt agttaggcca ccacttcaag aactctgtag caccgcctac    6840
atacctcgct ctgctaatcc tgttaccagt ggctgctgcc agtggcgata gtcgtgtct    6900
taccggttg gactcaagac gatagttacc ggataaggcg cagcggtcgg ctgaacggg      6960
gggttcgtgc acacagccca gcttggagcg aacgacctac accgaactga gatacctaca   7020
gcgtgagcta tgagaaagcg ccacgcttcc cgaagggaga aaggcggaca ggtatccggt    7080
aagcggcagg gtcggaacag gagagcgcac gagggagctt ccaggggaa acgcctggta     7140
tctttatagt cctgtcgggt ttcgccacct ctgacttgag cgtcgatttt tgtgatgctc    7200
gtcagggggg cggagcctat ggaaaaacgc cagcaacgcg ccttttttac ggttcctggc    7260
cttttgctgg ccttttgctc acatgt                                         7286
```

<210> SEQ ID NO 3
<211> LENGTH: 65999
<212> TYPE: DNA
<213> ORGANISM: Artificial Sequence
<220> FEATURE:
<223> OTHER INFORMATION: Synthetic polynucleotide (Cav3.1)

<400> SEQUENCE: 3

```
gagggatcca gctgtggtgt gcgccgggct cctcgccgcc gctttctctc gttctctccc     60
tccgcgtctc ggccggagga ggaggcagtg gcgccggcga cagctacggc aacggcagcc    120
acggcggcgg cagcgacatc tccgcctcca cccccgcccg ggacggcccc ccacggtctc    180
cccgccctc ccggtcctct agccgccgc ggggcggagg aaggagccag ccccaccc        240
ctccaaaccc acccccaaag agatccctcc tcccctcccc ctccccccgc cgtctctggc    300
gtggagccgg gacgatgctg accccttaga tcctgctcca gctgcgccga gggaagaggg    360
ggcgcccctc cccggacccc cgcccttcac cgggtggccc ctttttttcct cctcctctcg   420
ggggctgctt caccgaaggt agcgcccatt cgggcaaccg gagcctgggc gcgaagggaa    480
gaagccggaa caaagtgagg ggaagccggc cggctagtcg gggagcccccc gggaacccag   540
gggaagcggg actctcgcca ggcggggctt ccctgggacc cggcgccccg cgggcagcat    600
gccccctgagg gcaggggag ctgagctgaa ctggccctcc tggggggctca gcaagctctc    660
tagagccccc cacatgctcc cccaccgggg tcccccggtt gtgtgaggac acctcctcgg    720
```

| | |
|---|---|
| aggggctccg atcgccctc ttcggacccc cgggacccca gctggccaga ggatggatga | 780 |
| ggaagaggat ggagcgggcg ccgaggagtc gggacagccc cggagcttca cgcagctcaa | 840 |
| cgacctgtct ggggccgggg gccggcaggg gccggggtcg acggaaaagg acccgggcag | 900 |
| cgcggactcc gaggcggagg ggctgcccta cccggcgctg gccccggtgg ttttcttcta | 960 |
| cttgagccag acagccgcc cgcggagctg tgtctccgc acggtctgta acccatatcc | 1020 |
| ttcggggcac agcgatgggc cggactaggg gggtccacag gagggcgggc cgtgttgcca | 1080 |
| gaggggaccg taagccaggt gagttggaga agtgagcctg gactgtgaac agttgagtgg | 1140 |
| gggactgtta aggaggggag ggggcgtccg agtagaagcg gagactggtg ggtaccccag | 1200 |
| acgagcccca cctccgaata cacacacctc agccttcctt gggcggggt gagggtgga | 1260 |
| gggttgaaat ccaagctagg aaaagagagg agaggtgacc ctctggtaag catctggatg | 1320 |
| ctctacagat gtgggcagag gagggtcgtc atcctccaga tgtgggcagc ttcaggagcc | 1380 |
| tgggctttct actccgccag cccgccagcc gcgggttagc gagctgggtt tggttttcga | 1440 |
| gtttgggggc aggggtggag aggaagctgc ggggacggag gaggggagac cgcaatctcc | 1500 |
| tggggtttcc ttatgccccc ccccaaagt ttgcggcgga ttctagggtc cagtcccccg | 1560 |
| atctagtagt cctgaaggct gaggttttta ctgacctagc gggaaacggg gggtgggggc | 1620 |
| aggtcctgtc cccccaacac cctcccaatc cgcgggttgg aggcacaaca aggagatttc | 1680 |
| ggcggcgct gatgtcaggg gtgcagaatg agaacaagat gtggtgaagg gggagctgtc | 1740 |
| tgcccccaga gctggactgg agccccttc agagagagcc caatgcggcc agcgccctcc | 1800 |
| ccacctcaat tctttatctg atgttgagtg ctaaggttgg gttggggagt tttgtgcttg | 1860 |
| gttttttgtt tttgtttt ctaagggggg ggggagact gacaaaagcg ccggcaagtg | 1920 |
| ggggatggga ttaagctcgg ccacactacg cctccccttt cacaaatcag agtgttccgg | 1980 |
| ctgatggcag accaggtatg ggaaaccgca gtcgtctgaa agtattgggg ggaccagaga | 2040 |
| ctgccagtgt gttcattaag gaggactgag gtccagctcc ttaagcctac tctgtggatg | 2100 |
| ggttttagga acgcatgccc aacattccag gcagatgaat tttgattctc agcctcacct | 2160 |
| ctgcttagcc tggcgtggtc agggaacccc tgatcctctt tttaaaaat aaaaccaaac | 2220 |
| ccctagcaca aagcactcac tggcttgact gacgcccatc tctgggtac tggaaaggtg | 2280 |
| gggggctggc tggtatggct atcccagtaa gggatagcct cttctgattc tcttcttcta | 2340 |
| gcccagaggc tctctgggag tcaggctggg agaccccagg tttaccctgt agcccctgag | 2400 |
| aacccaagtc cggctccgct ttggagcaca ggggcagcgg gagagcttga tgctgccctc | 2460 |
| tgcagccact gcctctagtg cgcaaagcag gatgtaagct gagtgccccc acccgctgct | 2520 |
| ctacactccg tgagtctttg agaagctccc ctcagccctc caatcctttt gcccttcct | 2580 |
| tccttccttc cttccttcct tccttccttc ctctctaaac cgaagaaagg agaagaggga | 2640 |
| ctctgaggag tgtggtctcc ctaactggct tgctatctgg aattatgagt ctccatccca | 2700 |
| aggtctcctt ctctgtggca gagatggaga agagaaaaga agccctcatg cccactccta | 2760 |
| gccacattat gaatgggaaa cccccagcag tccctatcct ctctttctca ggagtcctag | 2820 |
| gggtgactgg aacatcttgt cacctctccc ttcaaatacc ccctaaaagc agaccttttg | 2880 |
| gcaagtatct ctgcccactt gccctatctc caggtggagg acctggaggt aaatactttc | 2940 |
| ctggagaaa ataagtgacc aggcttacaa gagggaaaag aggtgagagt ctagttaatc | 3000 |
| ttgagatttg gggagcaggc ccgatctggg gagtggtgtg tggtctgggt gtgtagcacc | 3060 |
| tatgtcccta gatcttaact agctagctga atatgccgag aacaatttct tggtaagggg | 3120 |

```
ggctgcctgg acatttattc ccatttcccc atccgaccca agtcacaagg acaagtgtat    3180
ttccacggcc agagaaggaa tctgaacggc ccctgagcc ttaaccctct cctttctctc    3240
tttttggtat ccgtgaggct tctgttggct tcaggagtcc ccaatgtagg tcatgaagac    3300
attggtcctg aggggcctga ctggcttccc ctccccaatg gactgaagct agttagcctt    3360
tttctcgaca tactttctc agcccttcc tcttgcagcc tcattaaaag gccagatttc    3420
ctagagtgga gatctaggtg taggtaggaa gtgtgtgtgt gtgtgtgtgt gtgtgtgtgt    3480
gtgtgtgtgt gtgtgtgtgt gtgttgtgga gggaggaagg aggaagggca caaaagttta    3540
tgttcctgta ctggggagat cagggacatg ggcccaagca gctccctggc agaccactgc    3600
ctcccaggtt acgggggaac actggccttt gcaatgtgtt tcttacaatg tgagggcgtg    3660 cggttccct ccgggaagg agttcctgag cattccctct cgggttgttg tgtcacatct    3720
ggaagtttgt gtaggagttt ctccaagctc agagcccagc acagcttttt ctcatttgga    3780
aatcacaggc tggcatttgg gatggaggag tgggagggg gccagagaag gagaggggag    3840
cctgccagga gttgagggga ggagggggcg gggggggggg gtaggcctga gagacaggag    3900
tcctaatggc ttccagaagt gaatgtgagt gtggaactgt gcgtcactgt gtgtgtccaa    3960
gtgtgtgtct ctagaaggga ggaggcccta ggaatttctg taatcttcct tgccattgtc    4020
ccagtgcccc aagtcttccc aagagaggat tctccattgg gtcctcagga gagagagaga    4080
gagagagaga gagagagaga gagagagaga gagagagaga gagagagaga gagagagaca    4140
gacagacaga cagagagaga cagagagaga gacagagaga gagagacaga gagagattga    4200
gagagagaga gctcacacat aagggggttg tttgaatctc atatgtcccc tcgtcccatt    4260
tccaaatcct agaccatcca gagcagattc tggggagaag agctgaggca gagaattgag    4320
tggaactggg gtggggcag aggatcttgg gtagtctgtc ccagattctt ctttcttctg    4380
ggtcatatgg actcctctgc acgtactctg ttccactgct gggggactcc ccatcaccc    4440 tagtgccagt tggagccatt cctgggatta cccctccacc ctggcccccc ttctgctgtt    4500
cccgccccag ctctcacccc gcccagcctg cctcagctgg gacggcgaca gacacactgc    4560
acacacacac acacacacac acacacacac tcacacacac acataccca gtcacagagt    4620 ttgaatcaga tttctggcct atttcccctc ccaaagattc cagtggccct ctctcatgtg    4680
tctctgtgtc ttctgtctcc tgtctctgtc tctgggtggg gctggctgcc tttcaggcag    4740
gcttcagttt tcagtttagt tggaaacctc tctccccaca cacccacaca ccggagctgg    4800
gggcgcatgg ggaaacaggg tagttagtag gacggggcca ttgttgggga ttccccttt    4860 ctgaagaaaa aataaatgag cacaggccat caaactaaat ccctgcattg tcttccaccc    4920
taggaagcat tggctcccat agactaccaa cctcctgttg ggacgggtgg agcaagaacc    4980
tgtgtcccat ccccaactc ttattagaag gccagaattc ctggttccag gccaatttcc    5040
tcctcagtat tccttagtct cacatttcca gacttctggg aggagagag gcagctagaa    5100 ggcctgcttg ctgtctgggt tcacaccctg ggcccagggc cttagatctc tagttgccaa    5160
taatctaggc aaaagcccta tctagataaa aacctatgga gaagactcat tgtggatat    5220 agcatgctct atttccctct cccaggaaag agagaagggg ggaggatgg tagagaggtc    5280 tgcttctgct gttctcgctt tctctgcttt tgatggtggg ttatggggag aagaaagatc    5340
ctcccctctc ctgctcccac cctttgggat ccactccagc ccggacagtc accatagcaa    5400
cagtagacat gtgaccgcac aggtctctca tagtcactat ggcaaccagt gtccccgtt    5460
```

```
cccttggtta ccatggggat ctgtcacatg gttcccccc  ccccaacctg ataacctgtg  5520
ggtctccctg cttcttttc  cttgcataag gacaagagag cagtctgggc aaggggaaag  5580
aatgtgtaag ggggtgggga ggggtgtctc ttcagtttcc atggcaacaa atccacacca  5640
cctggtgaca cattcttctg ttgttatggc aacagaagaa catcacacag tgacatagtg  5700
ccgtgttgcc aaggaaacaa gccccaccct gaaaagggtg aaagaccccc cccacacaca  5760
cacacacata ccttagatat tcctctattc agattgttct agatttgcca gtccttttat  5820
acctacctac agtgaagggg aagccagagt gcaagggata tgcctgggtg caggctggat  5880
tgccaagggt ccggagaagg ggattttggt gaagagcctg atatgggtt  gtctggggc   5940
aggttctgac tatcagaggc cccagactga gtgtgtctgg gacaaagttc ctccataggt  6000
caagtctgtt cctccttaca tcactgtcat gaatttgtca ctgttcaggg aaacatcagg  6060
aaatcatgaa tggggaggca catctggctt ctagattggc agatgagtga ctgatagaca  6120
cagtggctca ttcatttatt cttgctgatc atttgctctg gactgcatat gacactgggc  6180
tttgtagtgt ggctgctgtt aacgctgtga cagagccaag cacatggatg acttgaccag  6240
gtagggccac tgtcattgga tgtccaaata gatacctggg gcccttctcc cccaacattg  6300
ttctccaggg cccctcctag gccctgtctc tcctgcagag gagaatgggc taggttgggg  6360
gaaaacagac cagttattaa gggtaattgt gtcctttcct ttccaagtgg tggcttcctc  6420
cctttccccc ctcttccaga gtgacctctg gctgaccccc attctggaga gagatccatc  6480
gctacagtca ggaaaacaaa cagcccctgt aggaatactt tcatttaccc ctctcaccta  6540
ctaagccact ttaaacctag gataatattt cattttttta ctttttttt  ttttttgag   6600
acagggtgca gccctggctg tcctggaact aactctgtag accagactgg cttcgaactc  6660
caagatccgt ctacctctta ggtgctggga ttaaaggcgt gcaccatagt ctctttctct  6720
taagggatgg atattaggga aactgaaaca tcttatgact tctagggtgt taggcatggg  6780
tggtgatagt gatgtgcacc ccagagaaaa gagcctggct agatagaatg aggaaggctt  6840
caaagtggct gagggagaag tcagggttgg tgattcagca cagaggtggg ggatggggaa  6900
ggccagctgg gaggctgaga ctggtcctct gaacctccct gatcacctcc tcaggcctgg  6960
tgaaagcatt accactccag aagcaaggct aagacaggaa aggcccatgg gctccaggcc  7020
ctgagtggat tggcagggca gacgacaggc agctgcaacc cctttcttct ttctggactc  7080
tacttgtctc tggtttcttt gctctttctg tctcactcct gttttccac  gaggaaacta  7140
gggtgtctgg ttgtatatct gaggggtcca gggcccggaa ccttctttat ccagagggga  7200
tcttgtatat tttcatgcca acgggctgaa ggtcaaccac gcaacagaac ttatgtagaa  7260
aggctcggga tggagaaaga attccctctg ctccctagcgg cttgggttta gaaggtacaa  7320
gaaatatggt ggcagtctgg cctcacgtat ggcactgatg tccactccgc agagctgaag  7380
cttgtcccca gtgcaggccc tggcttggag agcagttttg atctgaaagg catggacatg  7440
gtgactacag gctgaggact ttgagaagac agggagctgg cagttggaga gagagcttgg  7500
ggctcctctg aagtgtcagg ggtaaggagg gggttgacga tgtaggcttg tgtatgtgta  7560
gtgcaggaa  ggaaggcgac agagtaggcc acaagcttgg aagcctcagt ctcatcctgg  7620
cgtcttgagc aactctggca catgacttgg cttcagctct ctgggtcttg ctgtccttgg  7680
gtttcggggg tggggtggag tggggtgggg tgggtgggtg gggaatagaa tgatccacct  7740
tggatgcttc acgggctgt  tgtgagcaac gtcgtggcat tgtgcgaaag tgcgtggtaa  7800
actgtaaggc aggcttaatc cgactgtagg tttgtgtaac acattcgcat acattatctc  7860
```

```
acttgcttct cacatctatc cggtgagcga ggaggatgag attcacagca aactcgtgga   7920
gcctggcatt tccacacgca caatcgatgc tattccctac atggcttgtg caaatagcca   7980
gggtagtcat ggcttctct accttacaaa ggaggaagat gggatcgaag tctctcaggg   8040
tgggagtggg tggtggtggt ggtggtgatg gtggttaata gacaggtagc aagcattcgg   8100
gatgccagga gaggctccca tcagccctgg ctctggatag ctgtttcctt gacacctgat   8160
acgtggttcg agcgagtcag catgctggtt attctcctca actgtgtgac tctgggtatg   8220
ttcaggccgt gtgaggacat tgcctgtgac tcccaacgct gccggatcct gcaggtgagt   8280
gtgtgtgtgt gtgtgtgtgt gtgtgtgtgt tagtggttct tggatcttag taccctgaac   8340
tctgttctac cagatccaac tggtgggttc caggtggggt gtgtgtgggt gtccccagt   8400
ccctcagttt cttcagcccc tcctttctac gtcaggcctt cgacgacttc atctttgcct   8460
tctttgctgt ggaaatggtg gtgaagatgg tcgctttggg tatctttggg aagaaatgtt   8520
acctgggaga cacttggaac cggcttgact tttttatcgt cattgctggg tgagggcttg   8580
ggctagggtg ggagagtagt gggcagatct cctgcctctt tggttgtcca ttcagcccag   8640
gctgcctgct tccagtgctc gggcctgtcc tctgaatctc accatcttcc ttttgagtcg   8700
gaggagactg tcattgcttg gtgggaggtg tccctgcccg ctagacagag agctgatctt   8760
cagcctccct tggtagagga gaggggagag tcctgggtca ctctgtcacc tcacagcagg   8820
agtcttccct ggcctctttc acatggagtt ggcctcaaac tcaagggcc tccttcccgg   8880
cccctcccca caggatgctg gagtactcgc tggacctgca gaatgtcagc ttctccgcag   8940
tcaggacagt ccgtgtgctg cgaccgctca gggccattaa ccgggtgccc agtgagtgac   9000
cccttagccc tcacccctgg acagagggcc ctcagaggaa atgtggcaca ggcatcatga   9060
cctgaccatt tgaagctgag acagagaagg gttcagtagg gacccagtca gagcccctag   9120
ctctggtggt atcactagca aagctacctg ggaaaatctc catcccactc ttttcagcca   9180
ggctttagac agaatcttag aaataccttta gacgacccct tcctagggga ataaaggtgg   9240
gtggggacca gtggagcaag tgtcagaccc acagaagggg atacaaagtg ctagtggccc   9300
tctctcaaga caaggctact ccacgcctta ccctctggcc ctggttgtat tccccgtcc   9360
ccaccccac cccccacccc tttccaactc ttgcagtgac tgctgggacc attatctaaa   9420
ttaaaccgca ttggttctg gagccaacaa aggtttggca gctccagctc ctttgccgtt   9480
ctgcccctcc tcctttgcag gcccccttg caattcttca acctatacac gattgcagat   9540
ggtccccact gggtcctcag gaggggatat cgtgcctgac tttatgcctg atgctgcagt   9600
agccgtgtgt gtgtgtgtgt gtgtgtgtgt gtgtgtgtgt gtgtgtgtgt gagagagaga   9660
gagagagaga gagagagaga gagaaagaga gagagagatg cagttatctc tgggagggca   9720
gaacagctga gtgagtctgg ggtgggacag tgatgtttgg tgctaaggtg gagatccaga   9780
agagggggcgt ggctggcctc ctctcccagg tgacagctac tagatttata gacctcagac   9840
taaccactgc tgtaattccc ttaatgcaag ccctgaggaa ttgatctcag ttggagcgct   9900
gaggagctga tgggggggggg ggtgaagaac tgaaaaggat taggaccgac tacagcaagg   9960
tggctgtagc catcaggaag gttaatcatt tgctggtgtg ctggtgttta gaacctttgc  10020
cctagagaga acagggccca cccagggcac tttgggggtc aaatggacca ctggagatcc  10080
attagtttga caagagctta gaagctctgg gttttctgaa ggctagttca aatgtttggg  10140
tcttggacct ggagggagga aggtgagtgg gtccctaata gggcttttat ctggggctgg  10200
```

-continued

```
gagtatgtag tggccttgac cctggaggga ggaaatattc ccccaaagat agagttatgt   10260
ctcttcagac cctgacttca agatctggac ccagcaggaa acagacacag agaacacaga   10320
tgcagggctt aggggctagg agtgggctca gaaacctggt tacatgctgg tcttcttgtc   10380
tgcctctagc ctttctctag gtccgtccta gttctcccag tggccctctg ggccatcat    10440 ttaggaaggt caggtgactg tgtctggtga gagaaggaag tgggaggtgt gtgtgtgtgt   10500
gtgtgccagt gccttgggga gcaggatttg gaagcacaaa atcctaaatt taagtcctgg   10560
cgcttacttt tagcagatcc catcctgagc agctcacgtc acttctgtga gcctcagact   10620
tctcatctgt aaattggggg tgatatcatc agccccatgg tgacacggga agagtgagat   10680
gggactcaga acttagaggg ctttggaaac cacagttggt accatacaac aattaatatg   10740
agtattaaca attaaggatt gcctgggaga gttaggggtt tatgccagtc tcccctccag   10800
cttaaatggg tggaccctct tggggaagac tgccagcctg tgccctggc acactggagc    10860 ctccagcatg gctcttctgc ccccacaggc atgcgcattc tcgtcacatt actgctggat   10920
accttgccta tgctgggcaa tgtcctgctg ctctgtttct tcgtcttttt catctttggc   10980
atcgttggtg ttcagctgtg ggcagggcta cttcgaaacc gatgcttcct ccctgagaat   11040
ttcagcctgt gagtcacggt ggagccggtg ggtgatggac tggggagctg tggacctctc   11100
ttagtccctg gcttcctgtt gccatggata tatgtggtct catatctggc atttggctct   11160
caaacttagt tacacagtgg gacaacctgg ggcattttaa agtcctgatg cccaggttac   11220
cccttccaga gatcccccatt gcattgacct ggggttcaac taggatttag gcctttaaaa   11280
agccctccca gaagccagcc acaaagtaca tagctttaat ctcagaactc tggagacaga   11340
gttgggtgga tttctgtggg tttcaggctg gcttagttta cgtaggtcag ggccagccaa   11400
agatatatag tgagatcttg ccttaaaaga aagaaagaga ggaagagaga gagagagaga   11460
gagagagaga gagagagaga gagaggatgg atacataagt cagggccagc caaagatata   11520
tagtgatacc ttgccttaaa agaaatacag agctgggcgt ggtggtgcac gtctttaatc   11580
ctagcactcg ggaggcagag acaggcggat ttctgagttc gaggccagcc tggtctacaa   11640
agtgagttcc aggactgcca gggctataca gagaaaccct gtctcaaaaa aaacaaaaca   11700
aaacaaaaca aaacaaaaca aacaaacaag agaaatacag acatacacaa agacagaagg   11760
aaagaaagaa agcagctggc tccttgaggg ctggggatat agctcagttg gtagagtgtt   11820
tacctgcttt gcccaatccc ctcccccacg gtaggtctgg cctaccctct gtgttccttg   11880
gcttctcagt ggaggaccct cctcaacagc cttatctctg cctcccctcg ccctgcagcc   11940
cgctgagtgt ggacttggag ccttactacc agacagagaa tgaggacgag agcccttca    12000 tctgctctca gcctcgggag aacggcatgc gatcctgcag gagcgtgccc acactgcgcg   12060
gggaaggcgg tggtggtcca ccctgcggtc tggactatga ggcctataac agttccagca   12120
ataccacctg tgtcaactgg aaccaatact ataccaactg ctctgcaggc gagcacaacc   12180
ccttcaaagg cgccatcaac tttgacaaca ttggctatgc ctggatcgcc atcttccagg   12240
tggggccaca cgggccctgg gatgttgccc agaacagtca caggacactg cacaacttgg   12300
gagtgctcat tctcagggtt agggtggtga ccaggggagc ggaacagacg ggaggagact   12360
ttagtggtgc cagccagagt cagccgtctc tcttgcctcc acaggtcatc acactggagg   12420
gctgggtcga catcatgtac tttgtgatgg atgctcattc cttctacaac ttcatctact   12480
tcattcttct catcatcgtg agtgactcct ccagccttcg tgggagcggg gcatcctgga   12540
gacacgggta gaggcagaga atagatggga agttcttagc tctcaagtcc tgtagggtg    12600
```

```
gcagcataat gagtgagtca ggagaaatcc aagaccaaaa gccagactct accacctgct    12660
actgttagga ccttttgcac gccatcttct ttgaggctcc attctcgcta atggctttag    12720
gctcttcacc ggtaaaatgt gtgtgtgtgt gtgtgtgtgt gtgtcagggg ggcgtgtgtt    12780
ctgaacccac aatgctatca cccccttctc cagggggtgct cagaaatggc caagtttagt    12840
tctgtctttg tgagcccag gggaacactg ccagcattcg gttggaaaag agaaagatgt    12900
tcggcatcct gaaatgctta caagcaaaga atcatgcacc ccaaattcca atcagtattg    12960
agaaatactg agagatcgct cattccttcc agctctgaaa ttccagggct ctgtgaaggc    13020
agaagacagg ccaaagcagc atcgtttaat cattttaatc actaccagtc atagtcgatg    13080
ctttcatggc taccacttac agctgatatt tattgagcac ttactgtgtg ccagccgctg    13140
ctctctgcac ttcctggggg gggggcggca tttcttcctc accgtgattt ccttgccacc    13200 tttgttttc aagcaaagaa aaccactttc cctcatttat ctgcccccac cacgtgcctt    13260
gtctaagcgg gttgatcaga cttgccaggg agggttgtta gtgctggtgt ggctgttctt    13320
cctccttatg tactcctgtg aggtgggcac ttcgaggact ctggcttcta agtaagaact    13380
cagagctcta gagggttggc cactggtcca ggattgtcgg aagtcgggc tagagttgag    13440 atgtcaggtc caggttacca actccaaatc catgtcactg agaggccagt gcagagccag    13500
gtggagggtc agatcccgag agaggaagat taagaatgaa attaagatca ttcaaggcgt    13560
gggacaagct tcagagagcc gaggacagag tgacgctact cctggggaga gccacagtct    13620
gtaggctctg agaaagggca attccctagg ctgccacaac tttccctggt ataaaagaat    13680
tgaccaggct tggcgcaaag cttggctggg gacctgtacc atccctgacc atttaccaca    13740
agagtgaagc aggtacttca ggcgagtcag ttgttcttca tctgctgaat tgttggtgtc    13800
ctcaggaatg cttgggtggg gggaggggca gacggggaca tcaggggcct agtttccacc    13860
ctcccacaca cctcctgaaa attcttccca aacagctctc tggaatcaca ctagtgaagc    13920
taattatcat aattactagg acatgagcta ggggggagaaa aaaagtccgc ttcgttagca    13980
caaatattta tctccatcct ttaggggttgt tgtctaaaca ataggttgcc cagggtcctg    14040
gggaaactga ggcacagaga tggagactgg ggaaggatgg gcgagtcaga acgacaggtt    14100
tgttaggctt ggggggggggt cccctccttt cagatgggga tattgacttc ctgtggttaa    14160
gaatcttacc caaggtcata aagcaagaat ggatacaagt gggaggatta taagtaaatc    14220
tcaaagggtt aatccgagtt gaatgttgtg ggttccctgt attttatcca tttctataac    14280
attctctcct aatagaaact gggaggatgc cttaggctct ccatgggtac acatttaaag    14340
gcagggaact ggaggataac tgcaaagtat gctatcacca gcagtagtgg gctaggcctg    14400
agctgttgca aaccctgtg cctggccccc aggtactcca ttgattgtgg cagctggcct    14460
gaagtttcgt ttttcttcag gacatctctt cttctgtcc ccaccctgc aggtgggctc    14520 cttcttcatg atcaacctgt gcctggtggt gatcgccaca cagttctctg agaccaagca    14580
acgggagagt cagctgatgc gggagcagcg tgtacgattc ctgtccaatg ctagcaccct    14640
ggcaagcttc tctgagccag gcagctgcta tgaggagctt ctcaagtacc tggtgtacat    14700
cctccgcaaa gcagcccgca ggctggccca ggtctctagg gctgtaggcg tgcgggctgg    14760
gttgctcagc agcccagtgg cccgtggtgg gcaggagccc cagcccagtg gcagctgctc    14820
tcgttcacac cgtcgtctgt ctgtccacca cctggtccac caccatcacc accaccatca    14880
ccactaccac ctgggtaatg ggacgctcag agttccccgg gccagcccag agatccagga    14940
```

```
cagggatgcc aatgggtccc gctggctcat gctgccacca ccctctaccc ccactccctc   15000
tgggggccct ccgaggggtg cggagtctgt acacagcttc taccatgctg actgccactt   15060
ggagccagtc cgttgccagg cgcccctcc caggtcccca tcggaggcat ctggcaggac    15120
tgtgggtagt gggaaggtat accccactgt gcataccagc cctccaccag agatgctgaa   15180
ggataaggca ctagtggagg tggcccccag ccctgggccc ccacccctca ccagcttcaa   15240
catcccacct gggcccttca gctccatgca caagctcctg gagacacaga gtacgggtga   15300
gagcgtgggt gggtatgctg ggaccccaca gttggaggct gggtggtaat ttggaagact   15360
aggagtctga gaacccaggg ccccagggtg cagattccag gttctctcgc agccttctgt   15420
agccctgaca tctttggacc aatcccattg cttcttttga gccctgctta tttcatccgt   15480
tcaaatggga attatgatta ttgtatatat taggagtaat gagagcagtc acacatgcat   15540
acttaccatg gctgcactc tatgcctctg gccataacat ctaactgctg ctgcccaatg    15600
gagtgcttgt cacatgcttt gcaggcaaga tctgcttgag tcctctggac aggttggtaa   15660
taagcttaca ggcacccttg ctgtgtgcac aagaggcaca aggtggctag gagtgtcggc   15720
aagtatgacc tcaagaccat ctgactctgc agcccactct ctgtcctttg tcccagggct   15780
cagcggggtg ggaaatggtg tgtgactgtg gcagtctggt gcctcacaag gtgactgctg   15840
taaacagaga gacctggagc aggagcagtc agtgcagaaa gcagctagcc tgtgggtaga   15900
acttcggtga cctgagggat tagtgatact tgccgcttgt gggcaggcta cccatgcaga   15960
cacagcctgg ggccttgtgt ttcagcgagg atgtggtgac agaaagttat gggataagtg   16020
agatgtcccc tgggaccaga aaatgtcacc acagaacaca gagtgaaagg ttcttatgct   16080
agctctccca ctgccctgcc ctgggtcgtg ggccggtcac atcccacatg caggcttcca   16140 cttttccactg tatagtaggt gggattgaga ccatcactac tgtgggagct tagtgatgtc   16200
ctgtgctata cagatgcatt ccggagggga acgtgtcgtt ttgtgcctac tagggtcag   16260 gctttgagcc aaggaccatc tcacacttac ttcaacagtg tggtctcaga ggtgccactc   16320
atttcttata ttctgtgacc aaaataggat ttagatggac agaggatgcc ttggggcatg   16380
tccctgagtg tattcagaat atacttggta tacgtatgtg tgctaatgtg catgaaggaa   16440
ggtggggact ccatgtgtgt atgtctatat gagggtacaa gtgtctgact acatgcatt    16500 tgggtatggt gctccttcct ggtgtgtgca tatgcccata tgtgtgtggg tctggtgtaa   16560
caacattgga tggcacaaat gtgtttgggt acccatgttt ggtgtatatt tatcatggta   16620
tacaaatagc atgtgcccac tacacatgtg cacagtatgt gcatgtagtg tgtgcgtatg   16680
tgtatctggt aggtgggata agatgtgtgt atgtgtgggt gggtcccaaa gatcccttgg   16740
gaaatgcaac tcagcactgt gtgggtgcat acctacactg cagggaaggg gagatggtct   16800
aggttcctgg cctaaatctc ctaagaccta ggaggacatg gtggctacct ctctatctca   16860
atcctaggat ccttagaagt gaccaccaat acggtgctat tgacataggg gtattttgtt   16920
tatcagaaat gccccattca ttaagtgctc agcacaccta tctctggaac cccagcctcc   16980
ctcctgcagg gtctacatcc tcctaggacc aggagctccc aaagagcctc taacacctac   17040
tcttttgttc caggagcctg ccatagctcc tgcaaaatct ccagcccttg ctccaaggca   17100
gacagtggag cctgtgggcc ggacagttgt ccctactgtg cccggacagg agcaggggag   17160
ccagagtccg ctgaccatga aatgcctgac tcagacagtg aggctgtgta tgagttcaca   17220
caggacgctc agcacagcga cctccgggat ccccacagac ggcgacgcc gagcctgggc     17280 ccagatgcag agcctagttc tgtgctggcc ttctggaggc tgatctgcga cacattccgg   17340
```

```
aagatcgtag atagcaaata ctttggccgg ggaatcatga tcgctatcct ggtcaatacc   17400
ctcagcatgg gcatcgagta ccacgagcag gtaggggtgc agcccaggct ggctctggac   17460
aatggcttct tctctagggc tggttcctcg ctgtggctgg gagaagggggg atggagagac  17520 gaagtgatgg gtggagcctc tagggggtaa gcgctttgat gattacttcc tttctgaatg   17580
aggttgctca ggcaggcaca ggtatgtcct gtctgggaag gcttctcagg agaaggaggc   17640
tttatgtgtg tgtaatgagc gtatgggta acaagccacc agaagacttg ggtctcttgg    17700
tctcttctct tggaaaatgc aaggcaggca agggatgtgt tatctcagta agtagagggt   17760
gactgacagg cagaagggcc atgcaggtag aagggaagaa tgggtggtat tgagtgcctg   17820
tgcttgggag attagcaggg tgcggcaggc aaggcagtct tggcttggcc tcaggtcaga   17880
accttgctgt aaaccagggt ggctctggca gggcagctta aaaccagtga gcctgaggag   17940
ctgctccaag gaggaggctg tttagtcagg agaagaggag gctcagcagg acggtgagc    18000 tgtcttcaaa tatttggagg actgtcatgt ggaagcttgt tctgtgggtt gatggctgcc   18060
agctatagag cctgggctga gagaggaagc tacctctaag ctgtgcaggt ggaatgtgtg   18120
gtcaagtcag ggggactccg ctggcctgtg ctggcctgtg cacatatgca gggctgtctg   18180
aagaagttgg ccagtggtgc tgcatgtagg ttcttctgtg ttattgtctc tttggctgtt   18240
tatctgggaa gtcttgccac cctgaggtag caggagggga gttgaccatc ggactctcac   18300
cttttctggt tctgaagtga gcatgtgcag ccctcctgcc agatcccac gctgacacag    18360 aggcatcgag agcttgtgac agtcgcacag gagtggagga gtgtctcaac cagtatggga   18420
tgagccgggt gtggggtag ggtgtgaagc cagcaaaatg ctcactttttc agagggggttt 18480 gaaccctggt accctcaccg cccccccccc ccccgaact ctaccctgga aatgtcatga    18540
gcagatatct ggctctttct tgaactgccc tgtctggcca ggcacacccc ttcatttttc   18600
acatccattg gctccattct ctcttgcttg aataacccac tgtggaacag ctatgccttg   18660
cacggttctt ccccagtgtc agcgaggtgt gtgtggaatc acacactggc tgcagtgcca   18720
acgggtggcc atgcatggca ctgggtgggc gtgttgtgtc tgggccgaat ggggcgtggg   18780
catgtatgca cacgccagct ctgccagcct cccgcagaga ggtgctctac tctgccaggt   18840
ggctggggga gggtggggga cagcatttcc cccttctgtg actcaagaga taaaaacccc   18900
taacctctac ctccttggat cccctagcct gaaccgccac ctcctctgtt tcactcagca   18960
ccagttttgt ttaagtccct ctctcccaag ggaacacatt tttgatgccc tccctccc     19020 ctgggggat gcatccaaca gtccctgcct ggccagatgc tgctggtgga ggctttgatt    19080
gcactgggaa gaagctgagt cagacaggct gaaggcagat gaagctgcag caagagggct   19140
ttcagttaga tgtcaagaag gatgcccctt tggaaaggaa agaaaagcca ttagttgaag   19200
tacttccagc atctccttag ccacgttcct gaggaaagag gagacaaccc tagctccccc   19260
ttaaccctca gtaataggaa gccctcattc taagctggca gcatctgctg tagggggataa  19320 gtttgtccta gaacctggtt gatgtaggcc ccatgggggt gagtgggagt ccccagcagg   19380
ctgggcagat gactggttgc cgcctggcaa gctcagagga tggggagggt gtcataaaac   19440
tccagaagct gccatggtcc tgtgcttgca ggcactgtgg catgaatgtc ccgccatctg   19500
ggcctctgag caggctgaag ggggtgctgg gtaggagggt ggagatggat gcagggctga   19560
gagatgcaga ggggcttaga ggggacacgg gaacggggca ggatgcagag agggcgaact   19620
tgagacccag ggagaagggg acagaaaagg cggggacagg tgtggaagga gagagagaca   19680
```

```
ggaaggcaga gaggaaggac actgaagaca gaggcggagg tctagatgca aaggaggaca    19740
ggggcaggga gggggagctc aggacccaga tggagctgac tgcagggaa gtggggctga     19800 ttggaaggaa ggctctgcag atgctactgc ggtggctctt gggccccagg ctcctacttt    19860
ccccatgggg ctcttaatga agtgattgta tccatcaatt gcggtattga tcagcttggg    19920
gagccctgga gaaggtgtga gttcagtccc agtcctcccc tccctggct ccccctgctt     19980 gttgttcagt tttgttgctg aagacgtttt gttgttgttt ccctccacc tacctctcag     20040 tgagggaact tcatcttgtt acacccaag accctcaagg ctgggaccat gttcacctca     20100
ccattttctt ctgattcccc tagcccttaa ccactagcca gcagtactgg tgcaaaagcc    20160
ggaaagatta gtgagaggga caaggacaca aaaggaggcc ctgagcaaga aaatgacatt    20220
gtgactatag gatgagcaaa ggaccctgtc ctcaccacca gggggtggt tcggagagta     20280 cagatggtga attatccgtc catccctcct attacattct atctattcat ccatctacca    20340
actcactaat ccatccatct atccatccaa ccatccatcc tcccacctgc ccatccatcc    20400
attcatccac taactcactc atccatccat ccatccatcc atccatccat cctcccacct    20460
accaatccat ccatccaccc actcatccat tcattccatt ttattccacc cacccaccca    20520
cccaccaaac ccccatccat ccatccattc tcccactacc tattcatcca tccatccatc    20580
ctcccactac ctattcatcc atccatctat ccatcctctc atctgtccat ccatctatcc    20640
acccatccat cctacattca tatcctttgt gtcagagttg ggtttgcaca gtggtgctaa    20700
taaatgttta acaagttgcc ctcagtaaaa caaataagc taggcctaat ggtgctggcc     20760
atcccagctg aagcagaaag attgaaggtt caaaccagc ctggactata tttactgaga     20820
ttctgtaaca acaacacag caacaacaac attaaacatt tagctatttt attttctgta     20880
tatgtgtgtg attgggtgga tatttgtgta tgtatgttga agagctcatg ggggtcagaa    20940
gatcccttga aactggagtt acagaatatt ctgagctgcc acgtggggat tagaaaccaa    21000
acctgtccct ttgcaagagc agtaagtgct cttaacggct gagatgtctc tctagtcttc    21060
aaaaaaaatt tttttgagt aaaggagagc tgagaatata actccagagt cgagtgcttg     21120
cttagcatgc cctagatcct aggttcaaac tctggctcta tagaaacaaa caagctcaac    21180
ctaattggcc cgtttccacg gggtaaatgc tcccaccata gccaagtgga gtagggaagg    21240
gatggactct gagctggtca tcgaaagctg catcggggac actaaattca ggtattcaga    21300
atgagcgagt cactagatat gggctggatg aacaagtgac aagatgttag gttgagaaaa    21360
actcaggcca gatcctgtga ggcacgggaa ggagtttggc ttatgctgat atgttcttag    21420
caaagatatt ttttttaaaag caggtttgtg tttcatcaaa agattcccgg aagtcatgat    21480
gaagtaaagt gaaaagaca ggaggggttg ctgcgtgctt ttttttttt tttttttttt      21540 ttattcctgg agagaaaggg actggggcga gcccacaggt ggctgaatcg tcagactccg    21600
taatagggag ctaacaggag aggacagaac aaagatgacc ccaggcttcg gcggtggggg    21660
gggggggggg gagagcaggg ccttgacaag atgtacctgg ggccactctt atctttctaa    21720
aaagaagtgg tcctgtgccc tgttgtccca cctagggctt ctctatgagt ttcggtcttg    21780
gagtcacaga ctaattgttc catcttggtt atgagtccca gtaagagcag gtgctaatgt    21840 tttgttttaaa gaacaagatg gcagcatata gggctggaga agttgaagaa gaatagaagt   21900
ctgggatagt tggccttta ggccaagaga ggacaggata ggaacaatct ggcttgtcac     21960
cagtgtctgg acccatcttg tcactgaaga tgtatgtcca gagaagggtt tctatttataa   22020 gtgatggagg ttggctccca gtaagggaag agatggtgag atgagggtgg gacccacatg    22080
```

```
tgacattcct ggactcttga aggggggtcac acactccttt tcagctctgt tgaaagctgg    22140
ggagcactct ctcctcagac acagacatgc cacatagtta ttccaaatgt ggcgtttgag    22200
ggcaaagctt catgggtggc ttctaattgg gcctggcctt tgctctccag atagtgagct    22260
agggctgtca gcctagcaag atgttgggtg aaaattttt gatggctgac tgctcccata    22320
ttttcaaggg gtcttggatg agggaagtaa gaaaggacca ttctggagct agaaggctga    22380
ggggagcttg tgtcctctca gggatcccct ggctctaggt ctccccagtt cctcatgagt    22440
gcacatcttg ggcacaaccc actgggagaa ttctagaatg tcagagggtg ggacagagcc    22500
agaacaccca ggcagggtgt gcccttgttc tgtttcaatg tcagttcatg cctaatacca    22560
ggagctgaac tccaggggac aaggagagga gctctcacct ccacaacagg tgagggaggt    22620
ggtatcagaa aggggcagga tgtgggggc catccagctg gcctagcttg gaaatgtact    22680
gagtggcata taggcacaag gtgatcaagg cgagagtgac agggatgtca caaggactct    22740
aaggaagcct gagctgccag taggtgcagg cctgttgggg gggggggaga agggagctct    22800
ctctatcact cagatgacag gccaggagag cctcatgcca agggcctggg tgaaagagaa    22860
caaaggtggg caggtctgca atcctactgc ccaggtcttc agccctggca cctgactgtc    22920
gggatggatg gcaggcaagc atgcctccca gataactctg aggtttccaa gacagaatct    22980
ccaggccggt ggagtggggg gagggggaag gagcacattc gaagagaagg tgaagggttt    23040
gttttggatg tgttgagttt gagatggctg cgggccatgc ggagagggat atcaggcagg    23100
cgctgaccgt ctgaacaagg agccaggggag ttggaggggg cttggttagt gtcctctaca    23160
ctccggtgac agctggaggg tggggagtga ggtgatggtg ggaggcgcac gggaagggga    23220
gggcatgggc ctagaatgaa ctctggctga ggggaaggag actgatggag cgggccccct    23280
agagagacag gagatggctg cctaaggcca aggaaggtgc agggcaggag gggccagtcc    23340
tggctgagtg cggccaaggc aattactacc agaaggacta gaaagatcct tgagaggtgg    23400
ggccagggct tgtaggtgaa tgtgcagagt gcacattcct gtatgtgggc agagcaggag    23460
agagacttat gagaaatgat ggggtccact gatacagggg atcctaatgc aggtggggga    23520
gggagggaga cgaaggtgca gactgaggaa ggaactgaag ggtggccaag tttgggacag    23580
aaaggaagct ccgcgtggga acaggaaact caggcatagc acaaccctgg ggctgcccag    23640
caggcatgga ctgtttggtc agcacagcct tgttcatgtc tctgacaact ccactctgtg    23700
gttcaggaga cagcagagag cccggaacac ggggactcac ccaaaccagg gacctccgca    23760
gcaggagtct tctgaagtcc atagcgtgag tgtggccttc agcagtgaga ggttggccag    23820
gaagatgagg aacagaagag ccccccctccc tccctcatcc cctgcttcct tccttcccat    23880
cccttttccc ttcttggtga gagtctctca ctatgtagcc caggctggcc taaactcact    23940
gtctaactca ggctggcctc acatttgtgg cagtattccc gcctcagcct cttgaggact    24000 gggggttacaa gtgtctgtct ccaatgtcac atgctgggaa tcaaaccag gctccacact    24060 gctgggcaag cactctctat tctcagccct cccatcctcc cctcccccc tttttttcct    24120 ttctttcttt tggtaaaaga tgggttacct tgtagcctgg actggcctag aactgaaaat    24180
gtagctgtcg ccacagtgac cttgagctct ttctcccgct gcttcctaag tactgagatt    24240
acaggcatgg gccagcgtgc caggctcgag gctccagcat tttaagtggc aggggcctgg    24300
gctgtctgtc ttgaagctga gccaacactg gcaagactaa gcctacctgg cttgtattca    24360
cttgggaaac ttctagtagc tggagagcct ggggagagga taaggctggc tgctggctcc    24420
```

```
atcgatactt aaggggcaca ggggaagtac agtgggggct ctggggtga ggggtgcaga      24480 gaggtgctgc cagagaggct gagacgggag gggcaaaacc ataatctgca tgcagccggc      24540
ctgcgagatt gctcaagaat tccttgccac tctcctgtct ccctggcttc tcacaccctc      24600
cagaatgcct aactcaggca ccctcatcca tccctgctgc ctgcctagac cccagctcct      24660
ggaagttggg aacagccaac acagggctga ggttagctga ggagtccaga ttggtgagcg      24720
gaatcttata gcattggtag agctgccagg ggctgagaag acgggcatga gacacaggaa      24780
gcctggagtg gcacgaccca gcctcctctt agctctagct ctggcttctc cacctttccc      24840
ttggaaaagc gcatcactgt ctgtcagaac cggctcccgg gcctcctgcc gggacagctg      24900
cagtatctct taattggtct tcatctcccc tccaagccat ctgcatgccg ccacccctgc      24960
agccagatta atctccttaa tacacagccc tgcacatctc ctccctccct tcagaagcat      25020
caatggcagt gtcgtgggcc aaggctggtc cagctttggt tgtggctgga ggccactctc      25080 cctgggggg ggggtctcac aacctcatcc tttgtcatct tactcactag gtttggggtc      25140
tcaagtatga tccccacacc cacccaaaca cacagacaca cacacacaca cacacacaca      25200
cagagacaca cacactcctt cctctgcccc ttgtgctact gctgcatgca gatggggtg      25260 ttttccatgg ctactcttcc ccagtgcccc cgcctgcgct ggcccattga ctaaagctgg      25320
cttgaagctt catgttgatc ctagcttttt ctcctactga gatgtagctt gcagatggtc      25380
tgccctgtca cattttgag agctctctgc actcacaggg ccacctgagc ctggtcctga      25440
gcttcaagtc ttcacgggct tgaactcact ggttctgtag agtcgtctca tcacaagggg      25500
gtagctttct gtctgacaca agaggtccca ggaggtccag gctgctgagg gatgtgccca      25560
aggtcacata ggtaaacaga cacagagtcg ggcagataga ctcagagtct actgtctttg      25620
ggttgagtcc cacttttgta tcaagagtgt tctgtctaca gagggcactt aaagcacagt      25680
caagggagat gttatagtag caagcaactg acctagggtt atagttgcta caaagtaatg      25740
gtcaagagga gggcaggttg ggagatgagg aaggaaggac tacagctagc agcagcacag      25800
agcagaggcc tgggtctcag gggcagaggc cctcacacat atctactggg ttctgacatg      25860
gaatggcata ggaatggcag tgagtgccta gccagagatt tgaagatttg aagggatttg      25920
aagccaggga tttaacagg gggtatgtgt ctggaatgtg gaaccctgcc acaggggctg      25980
tgtgtgttct gtgtgggccc tctctcagag tgtagcagga gtgatatcat gagaagtata      26040
ctcaaagcct tctccaaaga agccttgtcc cctccatcaa gttcccacat gtctccaagc      26100
ctcagtttct ccaggccacc tcctgtccct ccacccttg tttggttgaa caaaggttga      26160
gtagagaggg ttttttgttt gttttgtttt gttttgtttt gttttgtttt gttttgtttt      26220
gattttgttt tttgagatag ggtttctctg tatagccctg gcagtcctgg aactcacttt      26280
gtagtccagg ctggcctcaa actcagaaat ccacctgcct ctgcctcccg agtgctggga      26340
ttaaaggggt gcgccaccat gctcagccga gtagagagat tttgagtaga aagaaatga      26400 actctgggag gtctgtagtc cactggcaca gtgctgggtt atagcagaac atgtctccac      26460
ctctgcccgt ttgcgtggtc agaactgcgg ctgcagtccc tggggcaacc ttgttactaa      26520
gaaagtgacc atgtgttgtc ctatgttggc aaaacattcc cagcctctga tttagtaact      26580
tggacagatc tggctttctg gagaaaaaaa gaaaaagaag ttgttgcttc atcttcgtct      26640
tcttctttgt cattgtcttc ttcttcttct tcttcttctt cttcttcttc ttcttcttct      26700
tcttcttctt cttcttcttc ttcttcttct tcttcttctt cttcttcttc ttcttcctcc      26760
tcctcctcct cctcttcctc ctcctcttct tctaattctt catttcctcc ttttcctccc      26820
```

```
ccttctctct tcctctcctc ctcctcctcc tcctcctcct cctcctcccc ctcctcctcc   26880
tctcttcttc ctcttcttcc atggattgcc agaggatgga atattgggtt ctggaagaag   26940
cagaggccta tcccttatgt gtgtgcagga gagtggcaag gctgagacaa gtgcttaatc   27000
cactgtacca ggcactctag cttctccaaa gctgctgggc agagtggggt gggatcttca   27060
gccttttctg cctctccctc tggtgaagat caatggtaca gccctccagg agtcccctgc   27120
actggccttc tccctgagcc ctttgctata tactgataag ctgcgtttgt gtgtgccccct  27180 aggctattgc ctatgcagat tgactagaac tctgaggatt acttccggct gaatgaaacc   27240
tttgtactca cagtagctgt tccgttaggg accactgttg atgcaaatct atatcagtga   27300
tgtggtgcta gtagggcatg gtggaccagg tttgtcagtt caaggctaac ctggaataca   27360
tagggagacc ttcccctgtt ttgttttttt ttgtttgttt gtttgttttt tgttttgtt   27420 aattctcaag aaagctcttg aaaggtacta tgctttcagc tgcttgcaaa aggtttgtgc   27480
atttagattc ttagtactac aaattgaatt atctttattg tttgaaatac agattgaatt   27540
gtcttttatt cagttaaaat gtttgagacc agaaatgttt tagatttgag agtatttcta   27600
tgtacataat aagatacttt aggcagggtt cattgatggt tcatatgtac tccttacaca   27660
cactgcctgg ttcagaaatt atgtaatatg tgctttggtt ttgtctcatt ttgtggtttt   27720 gttttttgtaa caggggtttt gccctggcta gcctgaaaca gactatgtag actaggctgg   27780
cctcgaatct acctgcctct gctggggttg aaggtgtata ccacctacct acctaggaca   27840
cttgttttga ctatgaccta tcacacgggt caggcaggaa tgtccactct gagcatcacg   27900
ttgctactca gaaagttgca gattttggat ttggggtttt caattggaga tacccaattt   27960
gtatactggc tgtgatagaa aatccacccg ttgtaagtgc acctcatgtt ggcttacgtt   28020
tagacacaag tccgcaagtc tctaggaggt gtgtcacatg ctttgtccat cagatgtctg   28080
gattcacggg ttccttactg tctcagtggc tttgatctca atcctcattg ctaagggata   28140
ttggggttgc agtgatgtga aattgggctc cttctctggt tcttcctgcc ctctgcctta   28200
gagcacattc ctagtatctc ttagcttttt ctgtagcata ggcagaggaa ggttttttagc  28260 tgaatgtcag aagtctacca agagccagcg acctatgagg cacagtagca gtgtgttcag   28320
agcccagggt ggaaagctgg gtaagggagc tgcataagtg aggcaggctc actgacaatg   28380
gctccttggt aactggattt tggagtgcag agtagggtca gagaaggtct aagccttggg   28440
ctttatctgc cttttccctg ccttctgcac tgtgccaata ctggaggggc taaaggtcct   28500
gtctcagcgt ggccctatta actagatctg gtagtagcat cctcttgtgc ctccattcag   28560
agcttgtgaa tcaaatactt gcttaagatc tgccagagca gtggagggct gaaagagttc   28620
ccccaataac tgcttagcca gacctgcctt taggaagaat cccattgcga gctgagagtg   28680
tatctgctgt gctcccccca ccccaacccc agtttcccag cccactaggg agaggccctt   28740
tccttccagc tctctaacct cccccttcc caccccaccc ctgcctggtc acacagatcg    28800
gggccattag gatacatttg gttgttccca ggacctggct ccacgcttgg acagccagac   28860
gagtcatctg ggtaaacagg aggaggtgtc tgtcggatgg aacaagagcc tcatttgact   28920 gtttcttta actcagcttc ttgggcagct actatgcacc ttggactttc aggttctagt   28980
tcacctgtca ggtgggcagt gactccattg agctaatgac atccctacct gcactccagc   29040
cctcagccag gacacacctc tcccttctcc cccagacagt catagctcct ctttcttatc   29100
catccctccc tccccagggc tctcctggga gagccactca cccttcagag ttcattacaa   29160
```

```
atgatctctc tctctctctc tctctctctc tctctctctc tctctctctc tccagccctt    29220
ctcagcatca ccccacccec accccccgca tcttcttgtc ctgaacttcc acattttctg    29280
tctggatcat ttattttggc accaaggcag gttctaaggt cccttgtggt tattcagctg    29340
tttagtaagt atacaacttg tttctagtta gacacagggc tcttgggagg cgtgtttctg    29400
cagctctttc aatgcccggt acattgctag gcatacagca ggcactttgt actggaggga    29460
aggagactag tgagctggaa cagacagatg agatggcttt tgtcatctgt tcttccgagg    29520
gcctcgctag gatgcatccc tgctcccatc ccagaccttg ggtaggaaca taaaaggaat    29580
tacctccggt gttttacagt tggccagaga agttgggaat cttactgaag gtcacagagt    29640
ggcagagtga caggacgggc tgaggattag ttcagatacc atcaggcaca agctgcagat    29700
gcatcctcat tctgggggccc gccctcctgc ttattaacac atatgtgccc atatgtgcgc    29760
acacttgcag tgtgtctgcg aggaaacacg catagcctct gacgtttgaa gtgggctgtc    29820
aggcacacgg agtagctgtg gagcgatctg tatggctatg tggagctaca gggctgggtg    29880
tgtgtgttga gctttggcta tagccctctg atgtcattta gcttggtggc ctgggcctca    29940
gtacagggac tggaaagtct tagacctccc aggagagaca gcagaattta cacagccacc    30000
cctaaagaaa tccatcgtct cgggatctga gatccagcct tggggtccat gtgtcccttt    30060
cccaggatgg ctgtatttga atgcctttct tcctagatac tccctaaggt tgccatttct    30120
gcacctcctc tccctgggggc ccatgttcca ggatgtctgg gatgtggggc ttggggggtga    30180 gtctgctgtt acatacctga ttacccttta gcccgaggag ctcaccaacg ccctggaaat    30240
cagcaacatc gtcttcacca gcctcttcgc cttggagatg ctgctgaagc tgctcgtcta    30300
cggtcccttc ggctacatta agaatcccta caacatcttt gatggcgtca ttgtggtcat    30360
caggtatgac tgcccctctc tgcttctgtc tgaaagaggg ccagcaggga tggctttgac    30420
cttctctctg ggcctcacct tgctctccta gagcctgtgc ccctttcctg cctgcttttt    30480
ctcttgtcct cgaccctacc caggcctggg gtggatgagg gttggaaagc tggctctcaa    30540
gtggagtcgg aggaagaggt acagacagct tcccctcttg caaagcgatt ggaaaccgac    30600
tcagacgccc agcaacttac tttagggttt ccacaacctg gaaagaattc catccctcc    30660 cccccactca ccccccccatc ccggcccagg gccagaactc ctttattggt ttctggaatt    30720
ggctttagat ttcattagaa gagaacaaag caaatattct ataacttgat gctctagcta    30780
tggcaggatt tagggagagg actgcctgct gccaggatgt gatgatctct ggtggggagt    30840
ggagggtcaa gagagctgga gctgtctgtc accgggattt tcagcccccct tgaagccaga    30900 agggctgtgc agactcttct ctgagctggg cagggcaggg cagctgagtc tcagatgtca    30960
ccaatgggtc ctcagaaagg gaagtcaggg gtaacgggcg cagggactca ggctgcctgc    31020
ctcccacagc gtgtgggaga ttgtgggcca gcagggaggt ggcctgtcgg tgctgcggac    31080
cttccgcctg atgcgggtgc tgaagctagt tcgcttcctg ccggcactgc agcggcagct    31140
cgtggtgctc atgaagacca tggacaacgt ggccaccttc tgcatgctgc tcatgctctt    31200
catcttcatc ttcaggtgag cgagcacaag gctggccagg ggtggggtgg ggcaaggggc    31260
aggatcccag gacccaccct gacctgtct gcgactccct gcatctccag catcctgggc    31320
atgcaccttt ttggttgcaa gttcgcatct gaacgggatg gggacacgtt gccagaccgg    31380
aagaattttg actccctgct ctgggccatt gtcactgtct ttcaggtttg agggtcacag    31440
ggcaggggtg agtcggggaa gttgggtgtc cagtcgagtc ctgactcctg tcccctgcct    31500
gcagattctg actcaggaag actggaataa agtcctttac aacggcatgg cctccacgtc    31560
```

```
atcttgggct gctctttact tcatcgccct catgactttt ggcaactacg tgctctttaa    31620
cctgcttgtc gccattctcg tggagggttt ccaggcagag gtaacccct gccctgtcta     31680 tctcacccta ctgagggatg cctgcttctt cttccctcca ctgctgatta tgaggcctga    31740
aagatcttgt aggcagtaac cactggacga agccagggtg ggcctcaggt gggaggtgct    31800
ccgtctcata aaacctgcca tccgggctga ggaagctgta tgggttataa gttggcaact    31860
tataagattc tctttcagtc agctgggccc tttcccagaa aggcaagtca aatttgagga    31920
cctatgtagc tggaccctag agcatggggtt tttatgggac atctggggag gacccatctg   31980
ggctgagggg tgtgggaggt ttgtgcgcaa gtcatctgag agcaggctga gccgatgaag    32040
atgccaccag ggcccaggc agggctgagc tgcccagggt gagaaatgag cccaattagc     32100
tgcaagcatg gcagagatga gagtcctatt tccagcccag actccatcac ctccgtcacc    32160
ggcagcgtca tcaattaata ttgatttaca ttgatcctgc cccggctgtg ccagggcaca    32220 cttctgtcc ccaaatccta cctccttctc cttcagctct gcctgccttc cacccaagc      32280 tcccgtcatc ccagcatctc aaacagggca ggttgaccca acctagaaat gcaccaggtt    32340
gggcccagag aagctcttgg tccagttctc gctaggtgac ccggatggaa actcccgctg    32400
cggccttgtc tataaatacc cagcacacgg tggaaaaaca aaaatctatt ttccgactct    32460
ttcccagcct tgcaagggag ggctgttccc cctgggccgg gttgggctga gggggaggg     32520 ggggttgttg ggcactagtg gctacagaag aatatgcccc gcactggcct ctctcagctt    32580
ccattttaat tgtatagtta tccattatca catttcctcc ctgctgggtg gcagccatga    32640
cagcctgaag tgcatgcctg ggggaggctt tagggatggg tgggactctc tcaatggcac    32700
tcaccttaca ataggacacc tttttgggt tttccttgga ccctaagagt tgagaggtgc     32760
cagaggattt tcccaagagc ctcatgattg gcaggtagct gccagctgcc tgctgaagtg    32820
agggttgagt ggggatgggg tctcttcagg ctctcccaaa ggcaactggt gacggccgag    32880
tttactctca ggcaaaaata aacgataaat aagttcccga gggaagcaga aagctcctga    32940
gcctataatc tcttctctat ccaccatggt ggacctaggg gtgtccagtg tagggagccc    33000
cttcgccact aaccggcttt cacaaacacc ttgttaaatt gagtgctgct gagctggcct    33060
ggttgctagg cagcagcaat gtctgagtgt gggaacagag ctgccaggcc ctgacgtctg    33120
gcctggtcac cctggccctg ctgggggcct gagagctttc ccagcatggg aaggattgac    33180
aagggccttg caggagatcc cttcctaacc ctttatagtg taagtgtcct tgctggagag    33240
tgtcacctag ggcctggtgc ccttcaaggg gcggattgct ttaggtatgg tgtgcgatag    33300
agaaaggatt ttgaggttag acctcctcca tgggtggggt gaagctgtgg tcctgagggg    33360
ttggaccaac tccactgtcc catgtggggt atcattagcc acctgtcctt accactgtgg    33420
ggtttcagta aaccccatgg tccggtttgg gggttgtgat ggcctgaaat actgttttgt    33480
atctatgaac gacctgcctc actggaagaa gtagctgtcc tgttttgagg gagtctagca    33540
ggagacctca agggatagat ctcctgctgg cctcaacctc ctacccagag tgggtagggg    33600
gtggtttcag ggcagaacct gcttggctgt tgatttcctg actccagggg ggtagtgcct    33660
tgaattcctg tatatttgtc atccgtgcgc ttaattagat gaggaagcag caggccctgt    33720
gtgtagccat taattgatac taaacaacat catggccgcg ctcccactgc tgcttgtcac    33780
atcgcatctg actctgggcc tatgcatcca ctctgacttg aaaggacttg ggctgagagg    33840
attagaattg atgacgaggc atgacttcat tcctcatcaa ggccctgtgc ccacctttat    33900
```

```
ccacttctcc ttgctgtcct ctctaccatc ccttacccct gctgtccatt cccacacaaa    33960
tgcctcagag cagagagaga agggaggtta cgttctcagc tggagaagta gggcacagcc    34020
cactgtcact gactctgcac cgtgtggggc agtggcatta acttctctga cctcaggtgc    34080
ctgccctgga agatgcctgt aacgatgcca tcttccactt gcaagggag tgagctctgg     34140 ccataagcgg tttaaggctg ggtatggtgg cacacaccta taactccagt gcttaaaggg    34200
cagaggcaag agaatcatgc gttccattct agtctgagcc atggagtaag accctgtctc    34260
aaaaaggcaa gggctgtgga tggaattcaa tggtaggaca cttgctgggc acagtcaagg    34320
ccatggttgt gattcctagt cccacagaga agcacagtga ccactcttac aaggactacc    34380
ggaagactcg atcctccccg acccgctctc atctttgtgg ccttcgcttt cacccttcag    34440
attcattcgg gcctggggc tcgaggctga attctggaag gctgtcctgt cccgctctcc     34500
ccaccccgtg tctctcattt cctttttttg gtcttcttgg acattgctg atctttgaag     34560 gcgtgagagc ctgtgaagag cagccttccc ctgcctcccc ctctccctgt aggaaatcgg    34620
caaacgggaa gatacgagtg gacagttaag ctgtattcag ctgcctgtca actcccaggg    34680
ggtaggtatg cgatcacgag tcggcatgcc cctgtgccca gtgccccctc cacactgccc    34740
ctgtgtctct gtgttcctgt gttcatgctc agctgttgtg caacctgtgg tccgccgtgg    34800
tggtcattgg tgtcgtgagg tttgctttga ttttaagtcc cttcccccc acttgaggac     34860 acagaaggga ggaccctctt tgcctctgcc acatcaaccc acagagggca cattcccatc    34920
tctgccgggc ctgtggatgg gccagagaag gaagggactt agaatcctct atgtgcacat    34980
gtctgtgggc accgcatgtg tgcctgcctg catctaggtc ccgttggagt ctgaaatatt    35040
ctgcctcagt agagtgaaga cctgtggtca tagaacatgc tccctcactt actctcttgc    35100
tcttttgccc ttcgctcatt gcccttcgcc cccactggag accccacaga cacctcacct    35160
cagtacaagt ccttggagga tgtaaggagg gtgtatattc cttgccataa tgtaaccaag    35220
atttttaagt gcacctctaa gtgtctgacc accagtcctc gaattaaacc ccaccagcca    35280
tctcagagga tgtccctcct tttggcccct tatgccaaac ctgtcctctg tttttttttcc   35340 tgcactgaca ctagaatttg gggcaaagcc aggcttccca tgggaccccca tagtgctatg    35400 catccctagc agtcccctgg agatcccact tgataattaa agacctcgtt aggggatgta    35460
aactgagtta atgaaagcga tcccctgaga tgccaattat ccaatattta tgcccttatc    35520
aaaagtagca atcaagtatt tttttaata acttcttaag gagaagtgta taattactgg     35580
gaaacctact gacctgctaa gaaggaagta aaaaaaaaat cctatccaga gacaagagag    35640
agaaatagaa atggggccag gaaggagctg tggcttgggg aaggcttgag gaggtcagag    35700
gtcagaggtc agaggtcaag ggactaaagt ggcatctttg tgcgaagtcg ctctggcttg    35760
ggtcttcctg tttccttcac agatccatag gtttgaagtt cagggaggga caacctgagg    35820
agaagggaaa ggaccttgag taggggttta gaattgggc tgtagtggcc acctcaccct     35880
ggtctcaccc ctttcagaca ccccttctcc cctgaactag tcttggtgcc agtccagcca    35940
ggctgcttgt gccgtggtgg gcttggattc tccatggcct ttcctaaggt ttggctagtg    36000
ggaagtagag gcgtcagcca tgggaagccc caggctccca gctgggtgg tctggcctgt     36060 ccccgtgcat gcctcatatc gtggttgctg gttttttgtgg tctgtgtgtg tgtgttcat    36120 gtgaagagag ggagcctcgg cccatgctga cgacacctac ctggccaggg tcctaatggc    36180
ccactgttcc ctgaccctag ggagatgcca ccaagtctga gtcagagcct gatttctttt    36240
cgcccagtgt ggatggtgat ggggacagga agaagcgctt ggcccgtgag tagtggtcct    36300
```

```
gagggtgcag cctctggcct ttggaccagc cgggatggac tcagaatccc ctctcctctt   36360
gcagtggtgg ccttgggaga acactcggaa ctacgaaaga gccttttgcc acctctcatc   36420
atccacacag ctgctacacc gatgtcactg cccaagagct ccagcacagg tgtgggggaa   36480
gcactgggct ctggctctcg ccgcaccagt agcagtgggc ccgctgagcc tggaactgcc   36540
catcatgaga tgaaatcacc ggtaagggaa tgcatgccac tgccccactg gtgggagatt   36600
agcaggacag cagaatgagg ggctgacggc agacaggtcc aaggagacag tgctggatgg   36660
ggcagatatt gacagaaagt cttagccgtg gaggttaaaa aaaaaagcat cattctaaac   36720
cagcctgtac tgttctcttg tgaccttggg caggacttag cctttcagga ccctttttt   36780 gcagagcaag ggtgggatac atgtttctcc tctatattta ttcagacgct agaatctgct   36840
gcaggtatgg tgaatgtaac tgatctttac tgccccacta ctgtgcgaga ggaaccatca   36900
ttgcgtccat tttagagatg aggacttcag tctcagatga ctgaaatgaa cagcagagcc   36960
gatagaggca gctcctcctg tgggagactg gcatcagcct gtgcttgcaa agtcctttag   37020
ttcctgttta tttctaatct gtacctttaa cttgttacta ttttatttgg catttcgaaa   37080
gagtctcact atgtagccca tgctggtttt gaacacatga tcctcctgcc ctagtctccc   37140
agagtcctgg gataagagat gtacaccatc cctgagccaa ggctttgtgt attttagttt   37200
tctgagacag agtctcacta tgtcactcta gctgtctgga actcactatg tagaccaggt   37260
tggccttgaa gtcacagggc ttgacctgcc tccagaatgc tgggattaaa gttgtgcacc   37320
accaccacca cagcaactgg ctaagacttt gctttgagcg accaaattat tgcctacatt   37380
tatgtagtag aatgtggtat ttaatgcgtg caaatatgga atgacgttat taagttaatt   37440
aacgcatata gcacctcatg tacttttta tttcataaca tttaaagtct actctgcaaa   37500
ttcaaaaaac acattaggtg gggtggtggt ggtggtggtg gtggtggtgg tggcggcggc   37560
ggcggcggcg gcggcggcag cggcggcgca cgcctttaat cccagcattc agggaggcag   37620
aggcaggtgg atctctgagt tcaaggccag cctggtctac agagtaagtt ccaggacagt   37680
cagggctaca cagaggaagc tttgtcttga aaaccaaac caaaccaaac aaactaacta   37740
actaacaaca acaaaaatcc ccccaaacca accaaccaaa gaaccaaaca aaacacccac   37800
tcccaccacc attaggccat tgccagctgt caccaccatg ctaccatcgg tgtgctcctg   37860
tgctctgatt gacattttgt acccttggat caatagctgc ccgtccccag cctcccaagc   37920
ccaagctccg tgagccacaa ttcagctctt ctattcattc agcattttta gaacctaaat   37980
tgtggtcatg ggggaccccg tttctctttg cctggcttat tttacttagt ctccttttct   38040
tcaaggtcac tcattcttca aggtcactca tgttgttggc agtgacagga tttccttttt   38100
tttttcttcc atttttttact atttgtattt gtgtgtgtga gtgtgtgtat gtgtgtgtga   38160
gtgtgtgtgt gtgtgagtgt gtgtgtgtct gtgtgtgtgt gtgtgtgtat ataggccaga   38220
ggtcagtgtt ggatgtcttt ctttattgtt caccacctta tcttttgaga cagggtctct   38280
ggctggaatt ggggcttacg gatggtctag actggcttgt cagcaaactt ggggatatg   38340 tttgtctcca cccctgacct cagtgctaga gttacaggtg tgcacaacca tacctggctt   38400
ttgtacatgg gtgctggata tctggactca ggccctcata tctgtgtggc aaggatttta   38460
tcactaagcc atctcctggc cttcctcctt ttagaggctg aatgctgtgt gtatgttcca   38520
tgtgttctgt ttcttttttaa aaaatttat tcctattttt acttataaat atatgcatgc   38580
atgtgtgtgc agatgtgtgt gagagagaca cagaggagag agatataaac tgagagagag   38640
```

| | |
|---|---|
| caagggagag atggagtaag aaaaaggaga gggagagaga gagagggagg gagagagaga | 38700 |
| gagagagaga gggagagaga gagaggaaga gagagagaga gagagagagg gagagagaga | 38760 |
| gagagggagg gagagagaga gagagaggga gggagagaga ggagagagag agggggggaga | 38820 |
| gagagagaga gagagggaga gaggagagag agagagagag ggagagagag agagggagag | 38880 |
| agagagaggg agagagaggg gggggagaga gagagagagg gagggagaga gagggggga | 38940 |
| gagagagaga gagagaggga gagagagaga gagagagaga gagacaacag tgcccttaag | 39000 |
| aggtcagaag aacatgtaat atcccccctg gaacctgagt tacaggcagt tgtgagccac | 39060 |
| ccgatgctga gaactgagct agggttcttt aaaaaagagt attgcatgct cttaaccact | 39120 |
| aagccatctg tgtaacccca ttttttacaa tccgtttggt tgctggatac tttgctattg | 39180 |
| tgcacagtga ttcaatgagt gtgagagtac atctgtttct tctgcatact gatttcaggc | 39240 |
| ctcgtctgga tacctagtag tagaattgct ggattagatg gtcattctat ttttagattt | 39300 |
| ttctgaatat cctccatata gttttccgtg gtagctgtac taatttatat tcacagcgtg | 39360 |
| cacatgttcc cttttctcca cattgacttg gacaatagtt actccaacag gtgtgaggta | 39420 |
| cttactgttt aagttggatt tcagaggttt ggagatggca aaagcactcg tcgcacgaat | 39480 |
| acgaggacct gactttgaac ccatgaccca catacaactg ggcatgagaa catttgtgtg | 39540 |
| tagcgtccca gggctcctgt ggtgagatgg gaggcagaaa caggcgaatc atggaagttc | 39600 |
| ctaggctagc ttcctgcctc tgcttccctc caaagtgctg ggatcacagg ctaacactat | 39660 |
| cacacccgc tttcaattga attgcttct tcaagggtc tcagccttcc ttatgctgca | 39720 |
| acccttcat tcagctttat gcatgtggtt accctcatgc ataaaattat tgtcattgat | 39780 |
| acttcataag catattcctg ctactgttat gaattataat gtaaatatct gtgttttcct | 39840 |
| agggtttcaa gagaccctg tgaaagggtc attcgacccc tgaaagggtt gaaacccaca | 39900 |
| ggttgagaac cactggcttt cttgctatta agttgagttc tttcttgtta ttttatactg | 39960 |
| cctgtcagtg ataacaagac ttatctcacc agcgaagtga agaacaaatg gtattgctaa | 40020 |
| atccgctta gagatgagaa aatggaggct cagggaggct tagtaactgg cctctggcct | 40080 |
| cacagttcta tagactgaag ccagatccta actgaggcac tgggttccag acaccaccag | 40140 |
| tgaacgtctc ttctcccagt gtcgattcca gggaggctca cagaataggg gcacacagga | 40200 |
| gaagtgaagg cccttgcagc ctctgctgag atcatttctc ctctgcttac cctgcagcca | 40260 |
| agtgcccgaa gctccccgca cagtccctgg agcgcagcaa gcagctggac cagcaggcgc | 40320 |
| tccagccgga acagcctggg ccgggccccc agcctgaagc gtaggagccc aagcggggag | 40380 |
| cggaggtccc tgctgtctgg agagggtcag gagagccagg atgaggagga gagttcagaa | 40440 |
| gaggaccggg ccagcccagc aggcagtgat catcgccaca ggggttcctt ggaacgtgag | 40500 |
| gccaagagtt cctttgacct gcctgacacc ctgcaggtgc ccgggcttca tcgaacagcc | 40560 |
| agcggtcgga gctctgcctc tgaacaccaa gactgtaatg gcaagtcggc ttcagggcgt | 40620 |
| ttggcccgca ccctgcgggc tgatgacccc ccactgatg gggatgatgg cgatgatgag | 40680 |
| ggcaacctgg taagattccc atggggccct gtgacccctc accctgggtc ttcagagagg | 40740 |
| gcagccttgg ccaggcagca gtataaggga gttgtctcaa gggatgtcca gcctgtaagc | 40800 |
| tgtcctgtga gcagcctgcc tcattcattc tctctctctc tctctctctc tctctctctc | 40860 |
| tctctctctc tctctctctc tttctctctc tctctctctc tgccaccctg cagagcctca | 40920 |
| agccctggtc cttgtgtcct gggctgtgct ccgctgtcct tggtggatat gaatggtttc | 40980 |
| aggcagatgt gtatgaatct ttcatggccc tcccctgtg actcaggaag acccatcact | 41040 |

```
catctttcta aaatgatgcc tcccttcccc tcctgtcccc ctttctcatc tgaacctcat   41100
caccagcctt gacttacagc atgtcctcag ccacttattc ctcccccacc tcctccacca   41160 cccccttttgc cctgaagatg agcacaagga cgggaacaca ggatgcaggg ttagcacagg   41220
cgcagggtcc ccgtctcctc tgcccaggtg tatttgagca gacagctgtg atgagtacaa   41280
tgtttgatta ttgatgcagt ttccaaaccc agcagggaga aagggaaga aaggcaggga   41340 gctgggctgg aggctggatg ggaagaatac agagaagggt agagacaaga ggctggggat   41400
gcagggcagg agggtggaga tgaaggagga gagatgcgga ggggttggca tgtagggagc   41460
caagaggtgg ccttaaaggt aaaggaagag ggtagagggc tggtcctgag cttgcgaagg   41520
atgctgctca ggaaaaaaca gactttgatg gctcaggggg cctggttcac taactcggca   41580
gtgttccttt catagagcaa agggggaacgc ttacgagcct gggtccgagc ccggctccct   41640
gcctgttgcc gagagcgaga ttcctggtct gcctatatct tccctcccca gtcaaggtct   41700
gttatggtgc tgtctgggca tgctggcaat ggggtcctgg tgcaagggag tagggggtagt   41760 ctgcgggagc ctctccttcc cagcctttac ctctatccct ggggcaggtt tcgtctcctg   41820
tgtcaccgga tcatcaccca caagatgttt gaccatgtgg tcctcgtcat catcttcctc   41880
aactgtatca ccatcgctat ggagcgcccc aaaattgacc cccacagcgc tgtgagtcat   41940
cagaatataa acacttctgt tgagttctgc taagtgccag gttcctcctg ggttagcact   42000
cgggtcaagc aaaggaggtg agaaggctca aactgtctcc agtctgtgca aggtcacaca   42060
tcacagacaa ggcaaaggga caaaccagag atccttaggg ccttctggac cccatctcta   42120
agatgcctcc tgtgtcctct cctgcctcag tttcccatct actgacataa cagcctagct   42180
gggtactcca ttaccctcat agctacatat atattcttct gagtcttcct gagatgaggt   42240
gacacctaag attgatcctg tgtgggggct ggacagtact gttttccctg aatctggcca   42300
ggagtctcag tgtcactgtg actagtgcat tgccagggtc tctctctctc tctctctctc   42360
tctctctctc tctctcacac acacacacac acacacacac acacacagtg actggtacat   42420
tgccagggtc tgtctctctc tatctctcta tttctctatc tctctatctc tctgtctctt   42480
tgtctctgtc tctctctaac acacatagtg actggtacat tactagggtc tctctctctc   42540
tctctaacac atacagtgac tggtacattg ccagggtctc tctctctctc tctctctctc   42600
tctctctaac acacacaggc acatgtactc atacatatac caagggtaat gcagaactgg   42660
gtggagggac tgctcgttgc tccttgagat cctaccaagt cacaaacaac taggctttag   42720
ggggccctag gaagttagga ggtaagttgg tcactgctgc ttggctgtga atctttagt   42780 atgagaacag cataggccaa aagtttaga attagataat attacttagt attagatatt   42840
ttcccaaggg cctcagttct ttggatggac ccaactgatt ctaggtgctg tctctcccag   42900
cctgacatca gagcccctct tactgataac aattcagatt ctaggcggat ggcagaggtg   42960
gccctgtttc ccctcttggc actctatacc aattgcttgg aggtgtcaga ggtccccccct   43020 ctttgctttt tccattatta tttggatttc agagttgctg gggcttccat tttccattag   43080
ggtgagctcc agacaggcca agagaagttg gagaaagcct gacagttgga gaggcctacc   43140
taccaaaact tggtgggtgg gtgagaggta gtgctgggga cctccttcct gggctggttg   43200 ccctgtgac tacctgctgt ccaccccaca caccctgaca ttgtctctcc accttcccac   43260
tcaggttctc tgtctcccac tttgtccctc catgctcctt tcccccaccc ccgacacaca   43320
cacacacaca cacacacaca cacacacgtt caatactgct ggcacacctc aagctctctt   43380
```

```
ccctctgccc ccaggaatga cctcagccca taagtaccag ggcattgggt caccaatact    43440
cagcataagt atggtacctg aggtggcaca gactgtcccc atgtccctca gcctgcctac    43500
tgcaccattt ctggggctca cagcagggag gtgagggagc tgggtagacc acaggcaggt    43560
tggggatcaa gttaaatcct gctccagttt caaggaagaa atcaaggaac tgggactca     43620 gacagcagca tgtcccctct acaacacaca gaagaggttc ttctcttcag ggccagggca    43680
aaactttcca agtgaggcct gagatggcac tgtgagtggg gggctgggga ggggcaggga    43740
acaacaacct gttctgtgtc agatatctga agctgttttg acgtcatgca gaacaggtct    43800
ggtcatgcaa ataggcctcc ttcccaccat ctctctctct ctctctctct ctctctctct    43860
ctctctctct ctcaggaacg catcttcctg accctctcca actacatctt cacggcagtc    43920
ttcctggctg aaatgacagt gaaggtaaag ggcaggaggg ggtggggttg ggggggggaa    43980
gcactgacct ccgatggggg aggggggatg gggaaagtgg aactgccagg gtagaaggca    44040
agcagggctg gggactgctg ggagagcgac tagtgccgcc tctgccaacc actgtggtgg    44100
tggtccccag gtggtggcac tgggctggtg ctttggggag caggcctacc tgcgcagcag    44160
ctggaacgtg ctggacggct tgctggtgct catctctgtc atcgacatcc tggtgtccat    44220
ggtctctgac agcggcacca agattctcgg catgctgagg gtgctgcggc tgctgcggac    44280
cctacgtcca ctcaggtgaa ccacacacac atacacatac cttaacaacc aatacccca    44340 caagggtatt gtgcaccta ccttgtgcac cgtacctcct ggctatgacc tcatagggta     44400
attctgtgat ctgctccaga caacactgaa gctcctgccc ctggttattt ccttccaaat    44460
tacacagcca ctgcctgctc cgttccgtac acccctttcc agtgtgagat gctttcccgt    44520
tcagccctgc tgtgactagc tctgttggga gcccaatata atagctcata gggcccttgt    44580
ggcctccagc tgaagctctc ccatagagtc ccctcagggt gatgttcttg ccctccctgt    44640
gagtgacaca tcctcctact gtctttcctc accttctgca cccctcaggg atcacccatt    44700
gctataacac ttctcctagc aggggacagg tcttctccag tcaggcagtc ccagcctcct    44760
aactcagaat ttctcccgag tgaggatgat accaaaataa tagagctgtt tctcggtctg    44820
taatgatcca tctccttctt gcttgttct ccctgcatgc ccctactact gtctcccggt      44880
tgtcaccacc cccaccctgt cacactgtgt ccctgggtga tgcctccctt gtgtcgagcc    44940
ctctccactc caagcctgat caggaaatac acttgatagc ctgagagtgg aggcggaact    45000
gtgagacctg caagtgcctg tttggagact acagagcagt gggggggggg ggggagtcct    45060
ctcggtgggg gctctgtgaa aaggggactt ttccatagca tgtggtggaa gaacagcaag    45120
ctaaggtggt gggggagggg tttagcaggg caaaggctat gggcgtgtct gagtgctcac    45180
catctgcccg tctgctgtct gtctgctctc cagggtcatc agcccgggcc aggggctgaa    45240
gctggtggta gagactctga tgtcatccct caaacccatt ggcaacattg tggtcatctg    45300
ctgtgccttc ttcatcattt ttggaattct tggggtgcag gtgtgtgggg gaggggttgg    45360
tgttagctgg gggtgtctga gtctcccctc ccatcttgtt ctcctctctt atgctcctgc    45420
caccattgtt ccaaatgaaa ataaacagga ccctttccct ccagggctta ggcttcagac    45480
ccccgtgcct gattggtgtt ttacagaaac ctggaaacct tttggggggcc ggggggcggg    45540 ggggggtga ctcttctcga agggacccaa ttgcacaggc ccatcaggtc cattggtaac     45600
tgcagcttgt tgtccctaca ccatgatgta cttaaatcac acatctcggt ctgctagctc    45660
tggaatctcc tccttctccc tcccctcaag cagggtgggc tgagtgccag gcctgggat     45720 ccagagtcca gacagctggg ccaggttaac agagtgctgg caggcaggcg ggtgcagacc    45780
```

```
ccagacaagg caggaagtgg gggctgccgg ggaaacctgg cttctggccc agagaaggaa    45840
cttggctttg gaggaaaaag agccacagca gcctgcaggg ttcagcagac atctcaaggt    45900
tctggggagc cccttgggcc catcttggtc ttctagtgtc ccccactcca gcttcagggt    45960
agacagctgc tgctgggca gtgtgggaac tcctgggtgg ttgctgctac tctctccctc    46020
cttcctcctc ctgcttccag aatgcccact atgccctggg gagggctgt tccctggttt    46080 cctagaaatt ctctagcctc aaagaccagg ctacattggc caaagctgtg cagagcctct    46140
gccccaccct catcccacat gtggcctggt gcccacccct tcccccacct cccttggctt    46200
gggagagtga gccattgttg aatccagtcc catgggttta ggtttgtcct aaatggttcc    46260
ctcatccctg tccccaatcc tcctgtcctt cagatcccct ctcttccacc cccagcagtc    46320
atggcctggg ctatcctaaa ctttctagac aggcccatat ttaagaactt ttctgccaac    46380
tatggcctta gtgagtgatt aatggcctct gagcctcagt tttcctttct ataacgtggg    46440
gcttaaaatc tatatgcctc atagttacca tgagcggtaa atgcctagct tagggtggcc    46500
ctagaagcat ccatcggaac cactcaggct ccttgttaaa ggactgtgga gccgactcta    46560
gcacatcatc agatctagga agtcgggtgg gctaaaggag actgctctca ggtgatgttt    46620
ttggatttct cttcccccac atctggagct tcgctgacta tgttcatggt agaaggggag    46680
tggccaactc cctccttcca ccttgttctt cctctctggg aacaggaaga gggtacttat    46740
aggggagttc ctgtcagggt ttctggctga taccagaggc gagcatccca gacacccaag    46800
gtgtgctata tccctagact cagagcttgg gtggaattgg gagccctggg cttactctct    46860
gtctcccaca tgtgtgtgct cagctcttca aagggaagtt cttcgtgtgt cagggtgagg    46920
acaccaggaa catcactaac aagtccgact gtgctgaggc cagttaccgg tgggtccggc    46980
acaagtacaa ctttgacaac ctgggccagg tgagtggcag gtttgggatg gggaggagct    47040
taaagatggg accacacatc catcctgagt aatgtggtcc aagagagctg gaggtgggca    47100
accacagaga ctggccttct gctggctcac tgtcaccgtg tcccagagct agtgtaccta    47160
tactccccag tgaacagacc acagaggcct gtagctctct aaagatgaag gaatggagga    47220
tcacagaaag gggggtgggg gctggcccag ggccacagcg ccacacagtg ccacacagta    47280
gagtagagca catgtgaggt tgggagcagg gggctttgga tatgaaccct gtcgctatca    47340
gtgtcagttc agtgacgttg ggcagctgag ctgcaggggc ctctattttc tcatccggag    47400
aataggttca tgctaccgtc tccttggagt ttgcacatgt ataatgcatg aaatatgtat    47460
ttgcttacat ggtgaggctt cgtgtttttc ttctcggttt gtggaaatgg atatgtagat    47520
gatgaaatag ctgagctgaa gcaatataga ctggtgcact ttcttgccta ccattcatgg    47580
ggacttgagg acttcaattc ctattattgc aaaagaaaaa aaaagtagct ggttttgct    47640 ggtttgtttt gatttctaga ctcctagggc cttaggatct tcccacccta gctttagtcg    47700
tctttcctag catctgacca acatggggtc ctgagacaga gtgttccctg gggacctagc    47760
gtagggaccc caagttgttg acaggaggtc tgatgatgga atgtggtggg tagtttggcc    47820
acacatgcta ggtttcaaac atctgttatc tcctctcgtc tcctaccca ccccacccc    47880 taggctctga tgtccctgtt tgtgctggcc tccaaggatg gctgggttga catcatgtat    47940
gatggactgg atgctgtggg agtggaccag caggtaaggt gatgagaagg gccatgtctg    48000
ggttcaggtc actcagcctg ggctggttac cacgtgtaac caggcaagca tgggtcacaa    48060
taacatgctg cagcttattt gtaggcctgc agtaagtttt taaaaatgac ttttttttc    48120
```

```
tttcaaatg atgggcgaac agttaaaaac tggcacgaaa agtctgaggg cctgggaaca    48180
ctgggctccc attccttcag ggtaggagtc agccagaaca aagaaacagc ttctagacag    48240
agaatagcca ttcttgcctg atgccagctc attccagctc atcccagctg ctagcctgtc    48300
agatccccgg ggctgtttaa tttcatacca gtgcagctga ggtgggcagc acctttaggt    48360
ggttccccac caggctgatg tgacccgtg gtcttcctgc tcccccaacc agcccatcat    48420
gaaccacaac ccttggatgc tgctctactt catctccttc ctcctcatcg tggccttctt    48480
cgtcctgaac atgtttgtgg gcgtggtggt ggagaacttc cataagtgca ggcagcacca    48540
ggaggaggag gaggcgcggc ggcgggagga gaagcgacta aagaggctgg agaaaaagag    48600
aaggagtaag gagaagcaga tggccggtcg gtagtctttc cacctctctc tgggtcgtgc    48660
ttgaccatgg ccttgcgact gcaggggttt aggagctggg gcccggggc tgggagaagt    48720
gctcctgccc tccccccatc tcctttcctc aatagcatgt ccgcctttag agcctgcatg    48780
aagcagacca ggttagcccc cgtggggaag gagctgcccc ccaggaggct ccctaggtct    48840
cgacctcata ctccccagag gataccaggt agaaattgac acgcatctca gcatccctgg    48900
aaggagggaa aacaacctga cctgacgtca cacctcccag tactggtgtg ttcagtgacc    48960
tagggagtag tctaggtgct aactcagatc aacccaggtt gtactttaac ctctgtaact    49020
tgctcagagg ccatagctgc tcagccaggg gtcaggtgaa cctacaaaga aacaatcatc    49080
aagactgaac tttaggacca ctcccttct gcaacaaaac gacctggctc cctgatggtt    49140
gatggttttc ttgttgaaga agaaaagaag agagagagag agagagagag agagagagag    49200
agagagagag agagagagaa aatgaccccca ggtgtggtag cacaagtctg catatgaaag    49260
cagaaacagc aggattgcag gtttaaagct atcctggact acataatgag ttttaggcca    49320
gcttgggcta ataaacagtg agaccccccc ccccccccc ccccccccg tctcaagcca    49380
aaacccaaac agagaaaggc ctttggaaag atttacgctc tcaggaaagc tcaataatca    49440
ctctgtggcc caagaccct ccaggtcctc tgtgctccca gcatctcttg cacacagtgc    49500
gtgcggcttc atgcctctca ccttcatgct ttgccaggga caggctgaga cacacgggga    49560
agccacagag ctgggaagac aggagagcag cgcagtagtc gctttgtttc tggcatgtgt    49620
gcaggtgtgt gtgcacctgg ctcccgctcg ctccctccct ccctccctcg ctcgctcggg    49680
ggtttctgtc tgtctggtgc tctctgtcat ctctgcgcct ctctcagtca cagcccacgt    49740
ccctccacgt gcctgtctgt gtgggtttca aagcctccgt gtgtctccct gtgtctctcc    49800
ctgtttggtc tgtgggtttc cctcctctcc acccgctcac aaaccgtctg cctcccgtcg    49860
atcggatgtg ggccatgctc tgagtttccc ccttggtgtg tggaaatgtg agtaccacca    49920
aatgagttgg gggggctcct tctctccctt ggctgcatct cccagttgcc tgtggcaggt    49980
gcttggagga tggggagagt gcggaggagt cacagacagg atgagagtgg gactgggcca    50040
gagctgctcc aggaggatgt ggaggggac tctggcccccc aggtggccat gagcaggtgc    50100
agcttccccg cctctcacaa gcacccatta ccctccatag gctccgcctc ttcccagctc    50160
tgggttgggg tctggtcttg gcttctctta gcttgtacag ctgagcaggt accctgtccc    50220
cagggccacg ctcccacttc tgctccaccc acccataccc cttgtagtga gctgtctcaa    50280
caaggcatct gcacgtgcaa tttttttttgg caggaggcac tgaggcccct gccggaccag    50340
ctggctcctc ttctggggtc tgtagctatt caggtgcagc tgaagccaca gcaggggtag    50400
gaatggacat ctgttctgat gacagtctgc ctgtctctct tccagtacct tcctaccccc    50460
tgtgaccctg gcgagttggc tgaaacattt gtcatctttg ggtgcctgag tctgggcttg    50520
```

```
ggcattgaga accagatgct aatgctcagc acaccccatg tgtaggcaga gtgagggttg    50580
gagctgaggg ggagcgagct gctgaggggc cctgcccagc gcacctggtc cggtcaatga    50640
ccaatgtcgt gtttcgttct tttagatcta atgttggacg atgtaattgc ttccggcagc    50700
tcagccagcg ctgcgtcagg tactgcgtct ggggtgtggg ttcatgagtg tgggaacatg    50760
ctctttgctc cctctccatg gctcattggt tttatcctct aggggtgaag ggctgagggt    50820
ccttggggcc cccgagaagg cagggcctga agtgttgagt ctgcgtcgca cccctaatcc    50880
ccataggtcc atgataagtt ggatggaggt gaggtgggct tgggcccttg ctcaacagt     50940 tcttgtagga cctgggtctt ctacaaaggg gcttctgctg tcttggcacc gcctccctgt    51000
tcccctgtct ctcaccattt gattcagctg caaatctcct tgccttctct agtatgaagg    51060
gaagtctttg atccaaggga aaggatgaga ggagcagcaa ggggaaggat ttgttttaac    51120
aatgtagcga tgaataattg aaccaactca ttaatagtca agtcatcacg gtggccgcat    51180
catcactaca aacagcggaa cagcagaaat tgggaattga aagactgagt tagctacaag    51240
cttccccccc caaaaagcca gaggcttgag aacaagttga gtccttacct cccaaaactg    51300
tgtcttggga agacttccct gtgcctgccc ctcaccccat gcctgcctca ctctgtctcc    51360
tagtcctctt atattgttcc ccagatggag attgagaggc tcaaagtcta tggcagggct    51420
gtggggcccc atcccatccc cctgacatct ccacctggtg gttcccaggc tgtttattcc    51480
aggatccccc tcctggcctc ctcctgcagt ttggaagact tgaagtggcg gcatgtggag    51540
aagggctgtg ctgccctatt ttttttttt taactaatca aagacacatt taattgctga    51600
tcagtgcttc tgagctgcag aaggtcacac tctaactgat ggctgaaggg aaagtatgtt    51660
gccatttgta tatggggtct tcacatgagc acgtgtatac gtgtatactt tcttttaagc    51720
cttgagaaat tgtattaaga atgaaaggtc ttccactcag ctgctttctc tgctgcggag    51780 ggtgggggg ttcagcctgg gaacctctga ctgaaccatt cctccctgcc taggccccat    51840
cctggtgggg gatggcctgc ctggtctgtg agggctcaga gaccacctca aggggcgctc    51900
tgagccttga cagattctca tcttctgcca tggtcctgag ctatggtatt tgaccttcag    51960
tagcatctct ctggggtctc aggagtctct ggctaggttg tgtctctgtt gctaggatct    52020
ccgtgtctct gtgtcagact gttttccaag tttctgacac ggtaggggat gagaggatgg    52080
tgggagaaag ttgtcttcag cttagccctt ctgagttatt gaacagcagg ttcaaatgga    52140
gactgaagaa gacgcatgct cacctttgcc cctaaccact acccaaacac gtggctagcc    52200
cgcccgaggc tcctccactc agggcactgt ctctttaatc agcacatacg tgtaggcaca    52260
gccaccaagg cacaccatac ctacgcctca gcacacaccg gccatctcac tctgtacttt    52320
tccccaggga ccctggcctg ctcctgctgg cacccgtact atttattctc ttaggttgta    52380
acagtgaccc agactctaga tggtccccaa aacctcttat atccctcctc tcagagcctg    52440
gggttcttca aggtctatac cagagcttgc tttactcttg tgagtaagac ttatgcggag    52500
agacaggaca agacatcctg ggactcatcc ttaaggtctc ccacaggggt cttggtcctg    52560
aatttctaat aatctgaatt tcccagatgc tagggtaccc gtgtgctagt ctcccttcca    52620
cggtgacagc caagtctctc atctgggttt tctaggagtc aaatgtgtaa ccccccactt    52680
cctgctaaca tgtcttcatc caccttctg tagccaagag gagttatcac ccaggcaagg    52740
ggaaatgaaa agggaaaagt tggattagca agtgacactg ggcctaaacg cttaggtctg    52800
aagggagaga ttgggactgc taggtgacaa gaccagtcct gtgacacttg acctccagca    52860
```

-continued

```
tcagcttcct gtcctcagcc agctctgacc tccatctcca ctaaccccct cttttccc    52920
tcccaccagg ccaggaggat ccctggcagc tcggcttttg ctgtggggcc ctgtacccca   52980
gctaaaagcc tatttcctac cattttctct tttgcaaact gtctgccctg ctgtgccctt   53040
gggctctctg tgacctctac taactcactg tgcctgttgc tgtcacccac agctcctcca   53100
gctctcctca ttggcccctg gtctcccta ggggccctgg ggcctttccc ccactgtctc    53160
cctctgaact ctactctacc caaggcagtt gataactcgt agaaaggaag ccgggtgatc   53220
aggagggagg ctggagtctt gctgtctcat tctggtgctg ggtcacaggt ttgctgggtc   53280
tctctgaatg gtggagaggc tgccggcaga caagcggctc tagttggttt ggtgctcttt   53340
ggacttgtgt ttctaacgga gggtttcctt gatgcctgcc gatctgggct gggggctgca   53400
gtcagaaggg tatttgggac ctggagctat aacagatgc cctgtcccag ccgtgactcc    53460
ccctctcctc tgagttgcct ggagggtccc tggctgaatg cggccccacc accatcaccc   53520
agactcccga agcaaggctg gaaggcagag ttgttgttgg tgataactct atatggccct   53580
gatgtgccta caatagtcag gttgggtggg ataagagggg ttggggg tgg ggagggtcaa   53640
ggggacttct cccttccagc ctcccctcaa cattgtctca actaataacg gggctaataa   53700
ggagcagctt cttctaacct aattgtattc aaacatttta gttaattctc cattcatatt   53760
ttagcataat gggatcgggt gttctcgaca tttatggaga ttaatgcaga gaaagagttc   53820
cggctgctga ggcaaaacag ggcgactagc gccctctggt tctcatggta ctgaaggaag   53880
gaaggaaaga aggaaggaag aggccttggc tagcctagcc actccccacc atcgggtgtg   53940
gatgacctgt gggctcatgg catcccttgc ctctggcctc tcctctcccc atattcttgg   54000
gtgtcaggaa ggccacctga gcaaacaaag ccacacttgg ctggcccact ctgagaacaa   54060
agagatgacc tcaggcacct ctgagatgca cctgtgccct ggttatccac acctcaaggc   54120
cgatgtggag aggggtcagg tgggcttgca gatttgtctc gaagccaaac ctgccacttc   54180
tgggcactct tcttcctttg cttttggtg gggactcacc ccccaggcca gtccttgcct    54240
cagtttacct ctctgtgaag gaatcctctg catgggaaaa gatagttgta tttgagctgg   54300
cctggaccca aagcttttctg ccaccccctgg gccagttggt tcctggcatg gtattcagag   54360
gctataggcc tccctggcta gcttctgcca agacctccta agaggggaag ggctgtctgg   54420
gacctgaggc tgcccatgct ttccctccgt gtatctctct gtgagaccag tctgttggca   54480
tatttccaga tagcgtatcc ctcaccctgg cctggccctt accccagcac ctaaaaggag   54540
ggtcccctga aatctgcccc cagatttctc ttgcctgctt ggcaggatta ccttctggtg   54600
ctgtgacctt tctaagtggt cagctaacta caagaaaaac actatgccta tgacagatct   54660
cagacagctc ttccagccca gcctgcagtg tcaggcagcc ccaatacccca gggtaggctg   54720
ggtactcatt agaaactggg tgattctgtg ggtgctgcct tcctagcttg agtctgggac   54780
agggcagagg cctgagcctc cgcctctacc ctccccacat gaaactgtgg gaagtctggg   54840
gcactgtcct ctgtagactc tgtggtaggt cagcaggcag ccaagatgtc caatttccaa   54900
tctccggtcc tatcacaaat cccagctctg tgtaatccct tcggcggccc tagggctga   54960
gcttggagaa agcattggag ccttcgcctt agtggctgga gctccctctg agcccgatta   55020
gatgggggcgg ggggggggtg tctttcatct tattgatcca ccttgccgct gaacatggaa   55080
tcaaaggtta taaggagctg gtataattta gaggctgccc taggatatgg gctcacccag   55140
tgtctaatgt agaggagggg ctttgcatgt ctctatccca ttccaccctg actgcaggca   55200
gtagagcaga tgcttgacaa gggacagacc aaaacagccg gctcctgcat agggcagtgg   55260
```

```
gtgggggagg gggctggatg ggtgtcggga tgctagtggt gacctggaat gttttagcac   55320
tggtgtagag gctggcagca gggaggggct gtgggggagg ggctgtgggg ggagggttgt   55380
gcctgatgtc tactctactc tctttcctgc ccccaccaga agcccagtgc aaaccctact   55440
actctgacta ctcgcgcttc cggctcctcg tccaccacct gtgtaccagc cactacctgg   55500
acctcttcat cactggtgtc atcgggctga atgtggtcac gatggccatg gaacattacc   55560
agcagcccca ggtgagatca agagatgagg ccagcagcct tgagaccttc ccaggccgaa   55620
gtaaagatag cctctgggtg tcagacaagt gttgggggct ctacgtgggt cctcatactt   55680
gcggcagtct tcttagaggt gggtgtcacc tttgttttat acaggaggat actaagtctc   55740
ggtaggttag tttgctcaac caatatcaca cagctaggaa ctggggactg agcacatttt   55800
tattgagcat ctagtctgtg tggctctggg tcttggaagg tgaagaagac agactgatgt   55860
ttgtctgtcc ttcaagactc agattctagg acattctcag tccccagact catctgtttc   55920 cagtcaccccc tctcaaatac cttctctgtc agtctctcca tctgagcaag gaggaggttg   55980
aactgataat ggaccagcct cttttccagtc ttagtgttct gtgccttctg gcacattctc   56040
acgggtgtct caaggagaaa ttagatgcca ggtttgaata gtcatgggac agtggccagt   56100
ggtcagccat catggtagga aaggggggaaa acagggctcc ctcagcatca ccttacttcc   56160
cagctctggg aggtactgtg atggagggggt ggggcaggct tcagccttgg ggctacggaa   56220
accctgcatc tggcccccac ccctaccaga tcctggacga ggctctgaag atctgcaact   56280
acatctttac cgtcatcttt gtcttggagt cagtattcaa acttgtggcc ttcggcttcc   56340
gccggttctt ccaggacagg taacagcaga gagagagaga gagagagaga gagagagaga   56400
gagagagaga gagagagaga gagagagaga gagagagaga gagaggtctg ggagagtgga   56460
gagtaagtaa agatgtatct ccaggggggaa atatccagaa ggcttttgaa actgaagatc   56520
tatcttaacc atcctagagc tgatggtgat gatggtccca gagccagggt ttaagggatg   56580
ggagggattt gaggtttgac aaggcaaagc ttagagggct ttagcatcga gaaatcaact   56640
gtagcctcgg atggcactaa tgccacagag cttggagctg ggccgcctgt tggattggaa   56700
tcacagtcac ttagtgaccg atgactttgg ggggggggtgt gcctcagttc cctcatctgt   56760
gagaagaaag ctaacactgt ccatgtcaga gttgtaatat ggatatacag ctcttaaaac   56820
agctctctgc tcaaagtaaa cgtagaaaca tcgaaagcca agaccgatga gaccaggtgc   56880
cgtggtcgga gtctctggtg cagcaaggct cagacaggag gagagtttga gttcagtttg   56940
agaaacatag caaaacacca tatggggtgg ggcggggagg cagggataat gatgaacaat   57000
ggaaagcaca ggcccttccc agatctaatt ttctgtgcca ccatggcacc ctcccccata   57060
ctccctcccc gcctcagaga gctgtgttcc cgatttttcca ggtggaacca gctgacctg   57120 gctattgtgc ttctgtccat catgggcatc acgctggaag agattgaggt caatgcttca   57180
ctgcccatca accccaccat catccgtatc atgagggtgc tccgcattgc tcgaggtagg   57240
tccagcgctt gtacctgcct tccccagacg gagatggaaa gagttggtta tgcggatggc   57300
tctgggtttc caggggtttt ctcctagcct ctgcattaaa ggcttgtcta gcataagtgg   57360 gctgggggtat gggtggacca tcccaccagc tccagcccag cctggctctc ccagctatgt   57420 gatggggggac cccgggggggt ggggggggaac cagctcatga cactgtcctg ttctgcagtt   57480
ctgaagctgt tgaagatggc tgtgggcatg cgggcactgc tggacacggt gatgcaggcc   57540
ctgccccagg tagctgggag gtggggtggg cagaagggaa gggtcctcct ggggaggagg   57600
```

-continued

```
aggtgccctc caaaagggca gggcctcag ggaagccggc tggagagcca gcagcgtctt   57660
ttccgtttct tttcctcttc tccaggtggg gaacctggga cttctcttca tgctattatt   57720
tttcatcttt gcagctctgg gcgtggagct ctttggagac ctgggtgagt tgaggtttgg   57780
ggatggtgga ggagccaggg atggagatca agagggatca taagactaac ttggttttcc   57840
cctttcccct ctttccccc agagtgtgat gagacacacc cttgtgaggg cttgggccgg    57900
catgccacct ttaggaactt tggtatggcc tttctgaccc tcttccgagt ctccactggt   57960
gacaactgga atggtattat gaaggtgaga acctgggaac cccttgccag agctgctgga   58020
ataacaggga ggacacccaa cctctgatgt aagagtctag gagaggatgt tttagccatg    58080
aataaaagca taccccttg ttacccatgt cagaacacgc tggattctct ctctccccgg    58140
gacatgctct gattcactca tacctcacag caccaggact ctgatgttca tgcttaccca   58200
gggccttctc cctccgcact ctgctatccc atgaccactc atcggctgcc ctcctcaccc   58260
tcatgcctct gccctcaaca cctcccacag gacaccctcc gggactgtga ccaggagtcc   58320
acctgctaca acaccgtcat ctcacccatc tacttcgtgt ccttcgtgct gacggcccag   58380
tttgtgctgg tcaacgtggt catagccgtg ctgatgaagc acctggaaga gagcaacaaa   58440
gaggccaagg aggaggcgga gttggaggcg gagctggagc tagagatgaa gacactcagc   58500
ccgcagcccc actccccgct gggcagcccc ttcctctggc ctggggtgga aggtgtcaat   58560
agccctgaca gccctaagcc tggggctcca cacaccacgg cccacattgg agcagcctct   58620
tcaggcttct cccttgagca ccccacggtg agcaacagcg tcccttctaa agggccacgg   58680
gacaggagag gggtagggag ggcaaacagc agctcagtgg ggtcatacag gagcccagca   58740
gggcaggggc ttctccatct tcctgcccct cttacctcga cgttgaagga gctagctgcc   58800
aagtgccct cccagaatga ctgcccatat tctctgtata tggccgaccg ccctctagca    58860
gtgcggtggc agtcttacta gctcctctag cctggtgtgg cttccccgtc taggctccta   58920
ggttcaaggc taagttctct gtttccttct tgtttctttt tcacccttac ccgattgtca   58980
aacctctttc ctccatgctc ttaccttcca tctccctacc cttccttgt ctctttatct    59040
ctctctcct ctcccttttg gactctgact attctcatcc cccacctctc cttcctcctg    59100
cacctccccc attctcctct ctcatctctc tgttgctctg tgtgtgtgtg tgtgtatgtg   59160
tgtgtgtgtg tttgtgtgtg tgcgtcacat gggctccact tctattcttt caacccttt    59220
ccaacaatcc cctggccctg atacttctca ttgttacccc tctgatccct gctcccttga   59280
ctctcccggc tccccttttg gctggtcct cccaggacag acagctgttt gacaccatct    59340
ccctgctgat ccagggctcc ctggagggg agctgaagct gatggacgag ctggcaggcc    59400
caggggcca gccctctgcc ttcccttccg ccccagccc gggcgactcc gacccacagg    59460
ttattgtacc ctgtcacgtg ctccttcctc tgaccctgcc gagttgtgcc atgctgtgct   59520
gtgcttctgg ggtggctggg ggtgtgtggc ttgcccactg agtatctaga aaagagagg    59580
cctgtagagc cacataattg cacactgcac ctggcaggag acagtgggga gggtagtcca   59640
ggctctggaa agtagggaaa tcatcctatc aagggagaga gaggggatg gaggaggggc    59700
tggaacagag cagagatggg acagtgggac ttgggggta aagaaggcta ggtatcaggt    59760
ccagataaga agatctgcag aggttagtgc aagtggccat ggaaccctta gaggtacctg   59820
ttttagctag tctgattctt ctgtagtgtc cagttaccta tccacactcc tctagtggct   59880
ttttgagtac aaagtccact ggatgtgatg agggctgtca taggcagttt tctatcctga   59940
gggaatagaa gtgaattctg gggcataaat gtgaagcagg gcttggtttc ctcaccagat   60000
```

```
gcaattcctt cccggagcac ctagggtact cctccttctg ggcacaccac acgcagctta   60060
ccctgagctg ttgctttctt ggttcctcca gccctgctct cctcccattg gctcaatact   60120
ccctcaatct cccaccccca ctccaggtca ggagctgggt gtggactaca tctgaagcct   60180
agtgacacac cacctgatgg gagaaggggt aggctcacag gttcctaggc agtctttagc   60240
ctggtaggca atcgacagtg attttcacat ggtaaggacc cgtgcctctt gttagaatcc   60300
agtctcagac ctggcactga cctagaaagg gaatgtagct agtcttcccc cttctgcccc   60360
cccccattct aagctaagcc cataggaaaa gtggagggag gggggatagg ataggacact   60420
gattagaaca gcccactcac ccaaacacca ctcaccccac cctcgatatc ttgcaggtgc   60480
tgaagctcct aggtgagcca gctagatgat gtggtgacca gagtgtgccc ccttcacact   60540
ggctgggaga gcacctcctt aaggcccacg ttggagaggg ggaagcaggt tgcagtcagg   60600
cggaggaggg cccatgaggg gagaagccag aatctggggg caagccaagt cctgctaggc   60660
ttttggaagc gaagagaata ggcagaaaac agccgtcaga ctggtggcat tgtccccagc   60720 gtgcccccc ccatcccccg ctgccatgct gctctgtctg cagagaggag acagggcttt    60780
gctggccttt cttctttta ttttgtttgt ttggtatcat ctttatgaga gtagaagccc     60840
tctcctccgc tctctccccg ggtgctggta gtgtgggagg gggctgctaa gatgcctggg   60900
gtatctttag aatgtgtttc tgcgtctctt ggtctctctg ctttgccagt gtttgctctg   60960
tctctttggt gcctgctgca gactctctga tcagcacagg gggttgaagt gggagagggg   61020
aggggccgtg ggtatattgg gcaaggggcg gggagtgaaa tggaatgcct tcttccccgc   61080
tttgtggaaa agggggaagtg ggggctgcga gtgtgcccag tgtgtgtcct ggtttctcac  61140
gcctgctcat ctctctcctg tctagatccc tctagctgag atggaggctc tgtctctgac   61200
gtcagagatt gtgtctgaac cgtcctgctc tctagctctg acggatgact ctttgcctga   61260
tgacactcac acactcttac ttagtgccct ggagagcaat gtacatgcac acatcccttg   61320
ctgctccccc agcctgggtt cggctggctg cagggctcca ggtcttcctc ccactctgtg  61380
cccaggtcct gcccagaggc gttcacttgt gggcacaaag tgccccagcc tttgctggca   61440 tgaattttt ccttgtaccc cctgcgggta ataaggaat tagataagat aaaaaccaag    61500
accctgctca gaggggtcac atgagcagcc gtggtgacag ggttattcca ggaatgatag   61560
cccaaaacag aagtagcttg ggagtcagct tctgtgtttg gagccctgta ccagccaacc   61620
ctccctccct gctccctcct cctgcctctc tctcatgaga ctcactagtg tcctgggtga   61680
gacccatatc tttgctgtca ccaccatgcc tttcccctg gggaactgtt cctgtttcct    61740
tttgctgtcc ctgtgtgtct ttgtgtcctg tcctcaacaa gctcctgggg ctttggtact   61800
ttgaccttcc tacctttcct cagtttcccc ctgcccctc tcccacgaca gtgagcagcc    61860
cccctcctct cacccattgc ctactggtga gagctgggtc agctgaggca ggatcttgat   61920
caaagtctgg gaggggctct agaggatgtg ccagttgga aggagtaggt cctgggattg    61980
agaatagaag ggaaagactc aggctctact cagccttgcc atcttccact tgctgggact   62040
gagaccagct gagcccatgg gcggggaggg gcttttcagc ctccttgaga cagagtagcc   62100
tagcgaaaag gattctaaag agggagagag actctttggg atctagcctt ggtttcttct   62160
tctggggtcc tgggctgatc atttcctttc tttaaaacag gtttcccaga cccactccca   62220
cctcagtctg tccctgagg gagtactgag ttcccagtgc ccaggacttg ctacccacct    62280
ccaccctcta gagtctctgt gtgattaaag tagatccgca gaatacgatg ggacatctcc   62340
```

```
cttgtgttta cctgttattt aacctgcatg gatctagctc aggcctgtcc cctgttgatc    62400
cctggggtaa cttccagact ctctgagagg atcacatgca gttctggggg ctgctctctt    62460
ttttctcccc tcctggtcct ccaccatccc cagcccagag gctcacgggt gattctgtgg    62520
gcatgctctc agggtggggc cttccactc cttcctccct gtacgtagag actcattgta    62580
tgtcttccta tttccttcca tgctcatgcc cattaccttg gcctaggagg gtgtggaggt    62640
gggtgtgggt aggtgtatgt gggaggagat tgtgggtctg gcgggagagg gcttagttcc    62700
tgctgtctag ctttccctca gctaccaaac cccatctgca tgctcttcac cccatcctct    62760
catcctcttg cagatggtac ctcacactga ggaggggcca gtcccctag gaccagacct    62820 gctgactgtg aggaagtctg gtgtcagccg gacacactct ctgcccaatg acagctacat    62880
gtgccgcaat gggagcactg ccgagagatc cctaggacac aggggctggg ggctccccaa    62940
agcccagtca ggtaccaagt ctggggtgaa acagcttagc tcacacgagg agagacgacc    63000
ttgcctaaga ccaacaaaaa gcagtgtctc ttattttgaa gaaaccctaa gctaaaggga    63060
aatacccaga ctagaggagg tagctctcat cctagggcag tgatgggtaa aggctctgat    63120
ggggaggagg acccgaagga aagcatcaaa cactatctct actcaacccct cctgtccct    63180 tccccacagg ctccatcttg tctgttcact cccaaccagc agacaccagc tgcatcctac    63240
agcttcccaa agatgcacac tatctgctcc agcctcatgg ggctcccacc tggggcgcca    63300
tccctaaact accccacct ggccgctccc ctctggctca gaggcctctc aggcgccagg    63360
taagcaagtg tgaagggctg gacctaggtc ctggggtgag actctccaat tggaattcct    63420
gtgctgtcgg taatggccag agtcaacact tttattcttc cagccaatga gagagcagct    63480
ctaggtacta ggaacacggt attgggtaaa agagaagtag ttgggagtta ccaccaccac    63540 caccacccc ccacctcatg aacacacctt gtttcactga ggaggcctag gggccaaggt    63600
acagttgttg ccatggcaac caacatccat tggaggtggt acccaggtat caaggctccc    63660
aatcccaggt ccagagtttc cacactttgg gctaaactga aggacgtaag gcagggttta    63720
cgtgtcttta cttctggcca agcctgggat ccaccatcca tgaaccagag agtgacttat    63780
agagccagat gatgcttgtg tgccttgtgt tgatgtctgt gtctcctgat cacagatata    63840
ggaatatctg tcagcatcat gctcgtgggg gtcaggcatg gtccctcttc ccacacccac    63900
tcccctagca gcttcctgct gctaggcact gggatacagt tcctgctctc tgagctcagt    63960
aaggacagag acacacatgc tatcagatca cagcagtcac aggttagagc cccatggtgc    64020
ttgtgtatta tagcagggag ccccgaggag acaagggtta gttttacttg aagtggattg    64080
gcaggtactc atcacagaaa acccatgttc agcagagcaa gggatgcttg ccgttgggaa    64140
gggaattcaa ggccgaggga atcgttgcct tgctctttct ccctgaaggc tagaggcaca    64200
aaggggccag attgggaagc agaactggcg tgagttcttt ctggcttccc agagcccaaa    64260
gactgcagag agttcctcct gcaggatgat ttggggaagt agagcaggga ggacagaaga    64320
aaggtttggt ggttgaaggg gaggtgtggt ccacagagct cagagggctc atcaccccca    64380
ataagagaag ctaatagggt ggtcctgcag cttttgtgggg gggttaggga cagccagcat    64440
gacagaaagg ataaaggatg atccgagttg gaaaggaaat ctctggtctg agccctgctt    64500
ccactcccta caggcagcaa taaggactga ctccctggac gtgcagggcc tgggtagccg    64560
ggaagacctg ttgtcagagg tgagtgggcc ctcctgccct ctgacccgct cctcatcctt    64620
ctggggcggg tcgagcatcc aggtgcagca gcgctccggc agccagagca aagtctccaa    64680
gcacatccgc ctgccagccc cttgcccagg cctggaaccc agctgggcca aggaccctca    64740
```

```
agagaccaga agcagcttag agctggacac ggagctgagc tggatttcag gagacctcct    64800
gcccagcagt caggaagaac ccctgtcccc acgggacttg aaaaaatgct acagtgtaga    64860
ggcccagagc tgccggcgca ggcctgggtc ctggctagac gaacagagga gacactccat    64920
cgctgtcagc tgcctggaca gcggctccca gccccgccta tgtccaagcc cctcaagcct    64980
cgggggccaa cctcttgggg gccctgggag ccggcctaag aaaaaactca gcccacccag    65040
tatctctata gaccccccgg agagccaggg ccctcggccc ccatgcagtc ctggcgtctg    65100
cctcaggagg agggcgccgg ccagtgactc gaaggatccc tcggcctcca gccccttga    65160 cagcacggct gcctcaccct ccccaaagaa agatgcgctg agtctctctg gtttgtcttc    65220
tgacccaaca gacctggatc cctgagtcct acccactctg tccccatcac ctttctccac    65280
tgggtgcaga tcctagctcc gcctcctggg cagtccttct gaaagtccc atgtaagcag    65340 caaaggggcg taagtagcca cgaggcacct cgcatgcctt cttcagtggc tgagggatga    65400
caagcaggac ttcctgagag tcagtctgaa gagaacacag ccctggagcc ccccggcctc    65460
cgggaagaag gagaaggaga tgcccagtgt ggccaaggct ctcgacacca ggagctgttg    65520
ggagaaagca atacgtttgt gcagaatctc tatgtatatt ctattttatt aaattaattg    65580
aatctagtat atgctggatg tacgacattt tgtgactgaa gagacttggt tccttcttct    65640
tttatgtgtc tcagaatatt tttgaggcga aagcgtctgt ctcttggcta ttttaaccta    65700
aaataaccag tctagttcta tcccctcttc ttgtaaagca caagccgggg gccgtgagtg    65760
tattacaacc caacggcggc ccatcttcaa cggaaagcga gaaccatttt ggaaactgtc    65820
atgtaactta ttttctcctt taacctcgtc atcgttttct gtaggggaaa aaaagagaa    65880 aaagagaaaa aaaatgaga ttttacaaat gaaatggaac cttttttatat atatacatac    65940 atatctatat atctatatat ctatataaaa taaagtaatt ttccaaaata aaagttaa    65999

<210> SEQ ID NO 4
<211> LENGTH: 75
<212> TYPE: DNA
<213> ORGANISM: Artificial Sequence
<220> FEATURE:
<223> OTHER INFORMATION: Synthetic nucleic acid (Cav3.1-shRNA)

<400> SEQUENCE: 4
cggaattccg ggaagatcgt agatagcaaa ttcaagagat ttgctatcta cgatcttctt    60
tttgatatct agaca                                                     75

<210> SEQ ID NO 5
<211> LENGTH: 23
<212> TYPE: DNA
<213> ORGANISM: Artificial Sequence
<220> FEATURE:
<223> OTHER INFORMATION: Synthetic nucleic acid (primer SprF1)

<400> SEQUENCE: 5
aagtggtgct ggcagccgcc gat                                            23

<210> SEQ ID NO 6
<211> LENGTH: 24
<212> TYPE: DNA
<213> ORGANISM: Artificial Sequence
<220> FEATURE:
<223> OTHER INFORMATION: Synthetic nucleic acid (primer NeoP3)

<400> SEQUENCE: 6
```

```
cggtgctgtc catctgcacg agac                                          24

<210> SEQ ID NO 7
<211> LENGTH: 20
<212> TYPE: DNA
<213> ORGANISM: Artificial Sequence
<220> FEATURE:
<223> OTHER INFORMATION: Synthetic nucleic acid (primer srex2F)

<400> SEQUENCE: 7
cctccatgct ctgtttgact                                               20

<210> SEQ ID NO 8
<211> LENGTH: 19
<212> TYPE: DNA
<213> ORGANISM: Artificial Sequence
<220> FEATURE:
<223> OTHER INFORMATION: Synthetic nucleic acid (primer srex2R)

<400> SEQUENCE: 8
gttcccctcc ttgcctagc                                                19
```